(12) United States Patent
Podoleanu et al.

(10) Patent No.: US 6,769,769 B2
(45) Date of Patent: Aug. 3, 2004

(54) OPTICAL MAPPING APPARATUS WITH ADJUSTABLE DEPTH RESOLUTION AND MULTIPLE FUNCTIONALITY

(75) Inventors: Adrian Gh. Podoleanu, Canterbury (GB); David A. Jackson, Canterbury (GB); John A. Rogers, Canterbury (GB); George M. Dobre, London (GB); Radu G. Cucu, Canterbury (GB)

(73) Assignee: OTI Ophthalmic Technologies Inc., Downsview (CA)

( * ) Notice: Subject to any disclaimer, the term of this patent is extended or adjusted under 35 U.S.C. 154(b) by 0 days.

(21) Appl. No.: 10/259,671

(22) Filed: Sep. 30, 2002

(65) Prior Publication Data

US 2004/0036838 A1 Feb. 26, 2004

(30) Foreign Application Priority Data

Jun. 28, 2002 (CA) .............................. 2390072

(51) Int. Cl.[7] .............................. A61B 3/10
(52) U.S. Cl. ....................... 351/221; 356/497
(58) Field of Search ................. 351/205, 216, 351/221; 600/478; 356/477, 479, 455, 456, 497, 474, 932, 450, 453, 491, 301, 300, 72

(56) References Cited

U.S. PATENT DOCUMENTS

| | | |
|---|---|---|
| 4,589,773 A | 5/1986 | Ido et al. |
| 5,321,501 A | 6/1994 | Swanson et al. |
| 5,459,570 A | 10/1995 | Swanson et al. |
| 5,469,261 A | 11/1995 | Hellmuth et al. |
| 5,491,524 A | 2/1996 | Hellmuth et al. |
| 5,493,109 A | 2/1996 | Wei et al. |
| 5,537,162 A | 7/1996 | Hellmuth et al. |
| 5,975,697 A | 11/1999 | Podoleanu et al. |
| 6,057,920 A | 5/2000 | Fercher et al. |
| 6,172,752 B1 | 1/2001 | Haruna et al. |
| 6,201,608 B1 | 3/2001 | Mandella et al. |
| 6,615,072 B1 * | 9/2003 | Izatt et al. .................. 600/478 |
| 6,618,152 B2 * | 9/2003 | Toida ......................... 356/479 |

OTHER PUBLICATIONS

"Simultaneou en–face imaging of two layers in the human retina by low–coherence reflectometry"; Podoleanu et al.; Optical Society of America; 1997.

"Optical Coherence Tomography"; Fercher; Journal of Biomedical Optics; Apr. 1996, vol. 1 No. 2.

"Transversal and Longitudinal Images from the Retina of the Living Eye Using Low Coherence Reflectometry"; Podoleanu et al.; Journal of Biomedical Optics; Jan. 1998, vol. 3 No. 1.

"En–face coherence imaging using galvanometer scanner modulation"; Podoleanu et al., Optical Society of America; 1998.

"Coherence imaging by use of a Newton rings sampling function"; Podoleanu et al.; Optical Society of America; 1995.

"Optical Cohernce Tomography"; Huang et al.; Science, vol. 254.

* cited by examiner

Primary Examiner—George Manuel
(74) Attorney, Agent, or Firm—Marks & Clerk

(57) ABSTRACT

The present invention relates to a multiple channel optical mapping apparatus which can deliver one or simultaneously at least two images of different depth resolutions or sequentially, images with different depth resolutions, or a combination of these images, or a single image with adjustable depth resolution. The multiple channels could be either multiple confocal channel and one or two optical coherence tomography channel, or two optical coherence tomography channels, or two confocal channels. The channels, either OCT or confocal can operate on the same wavelength or on different wavelengths. The apparatus can display both transversal as well as longitudinal images in an object, particularly the eye.

83 Claims, 35 Drawing Sheets

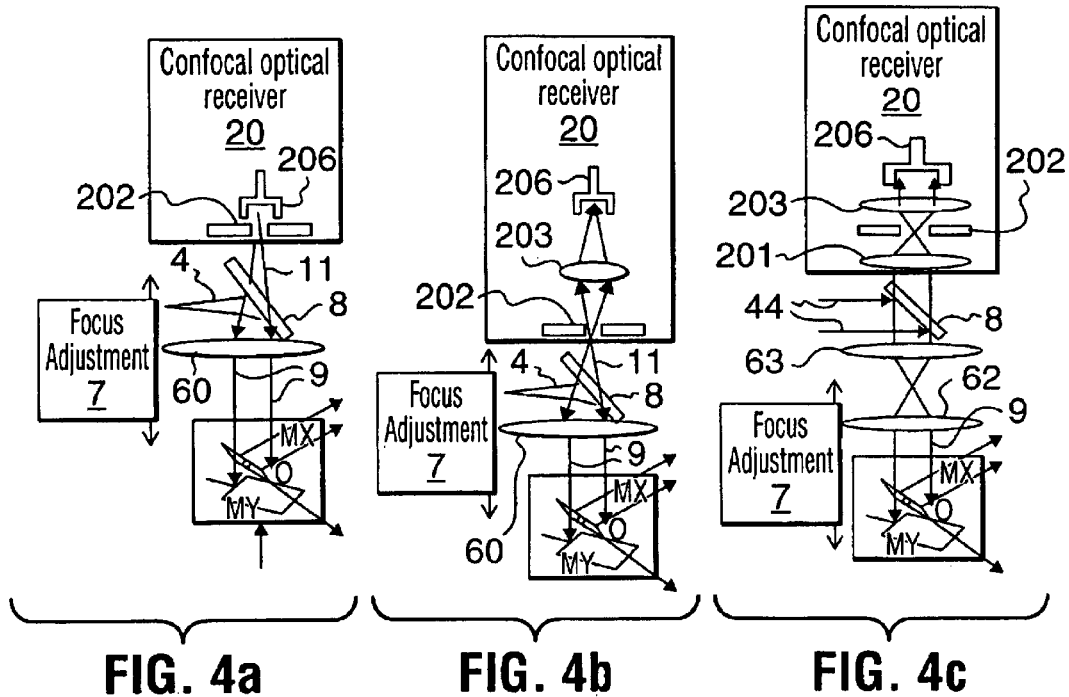
FIG. 4a   FIG. 4b   FIG. 4c
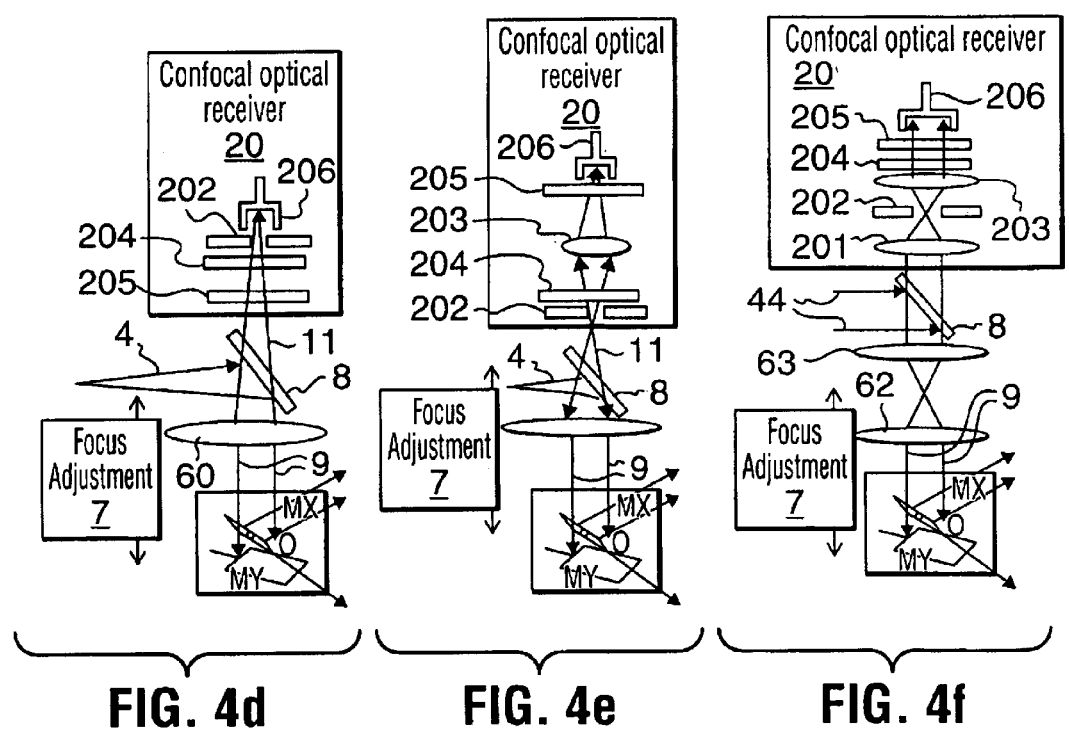
FIG. 4d   FIG. 4e   FIG. 4f

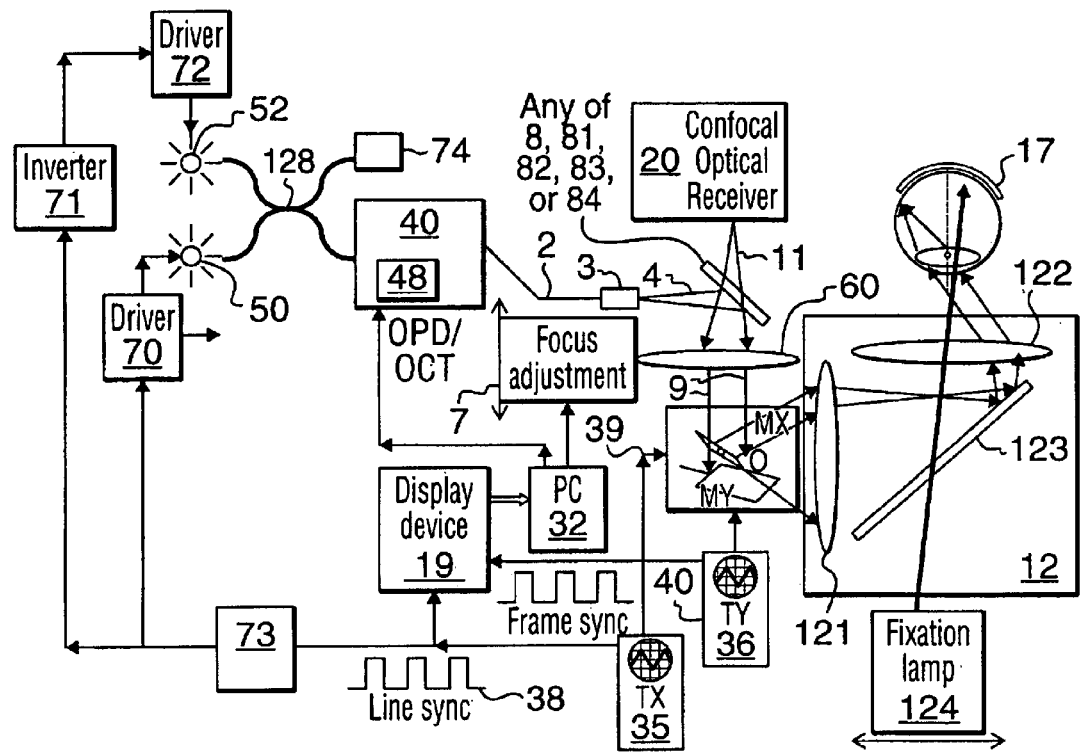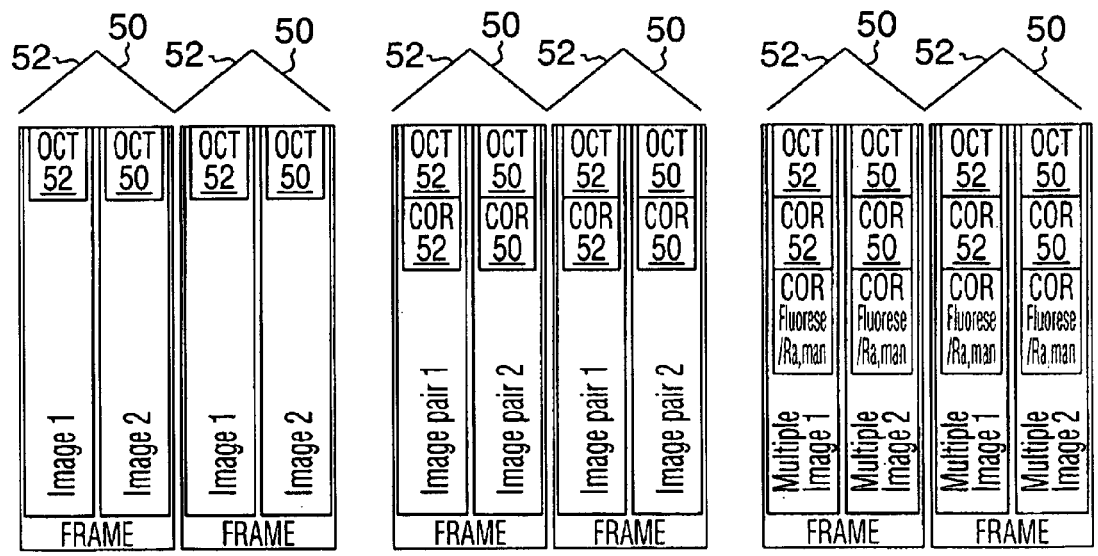
FIG. 9a

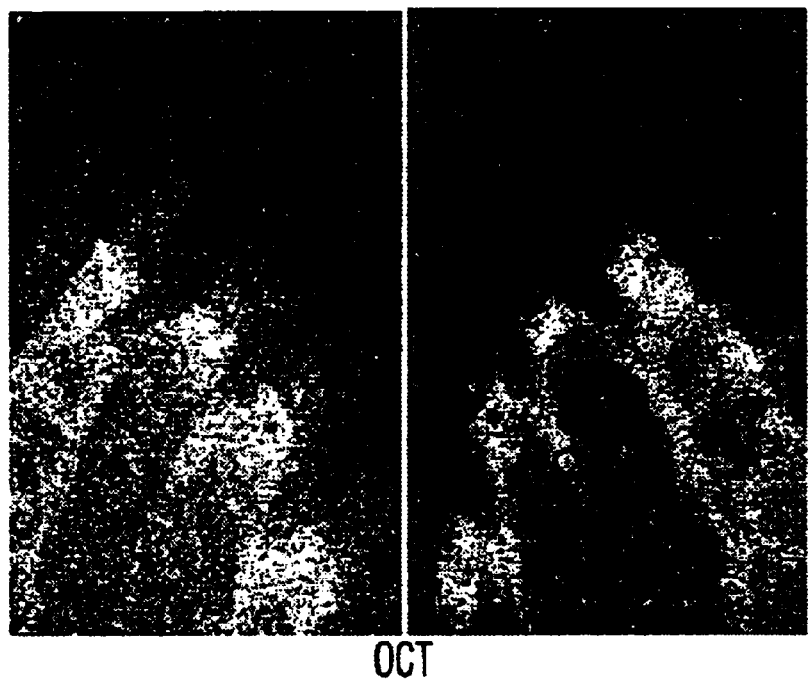
OCT
FIG. 10a  FIG. 10b
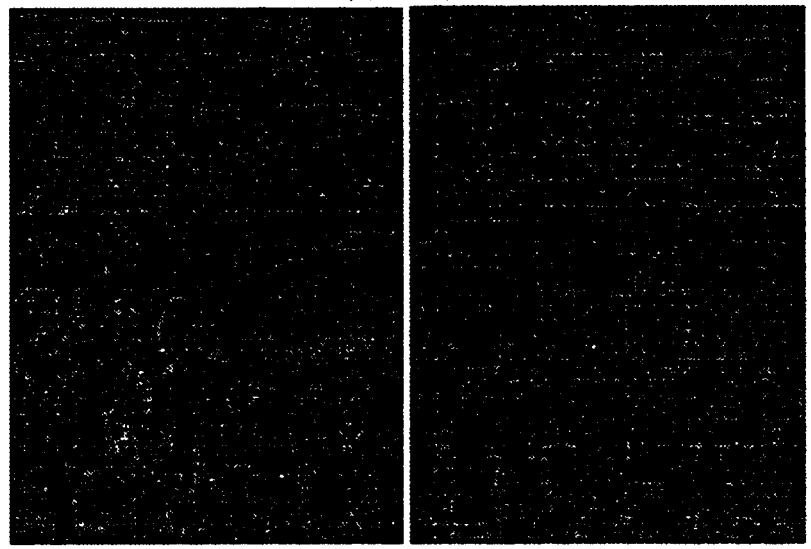
Confocal
positive ramp, 200 μm source
negative ramp, 20 μm source
FIG. 10c  FIG. 10d

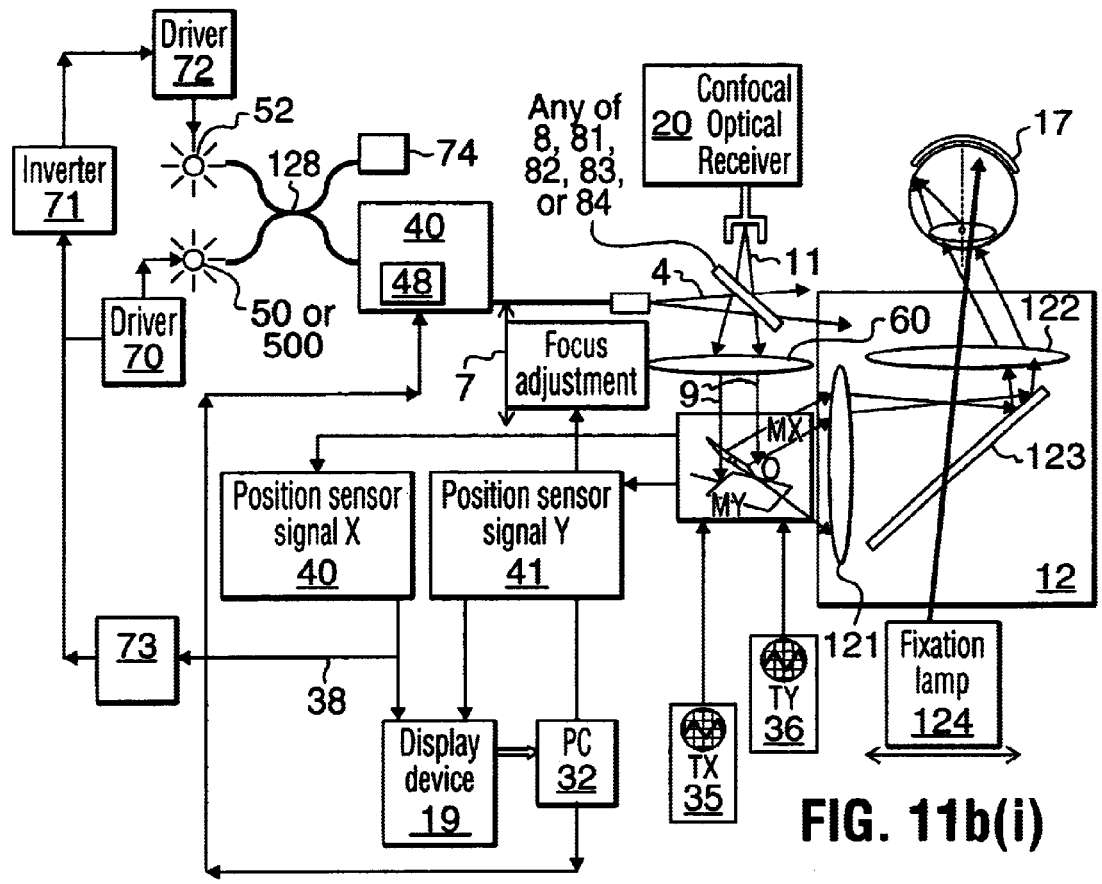
FIG. 11b(i)
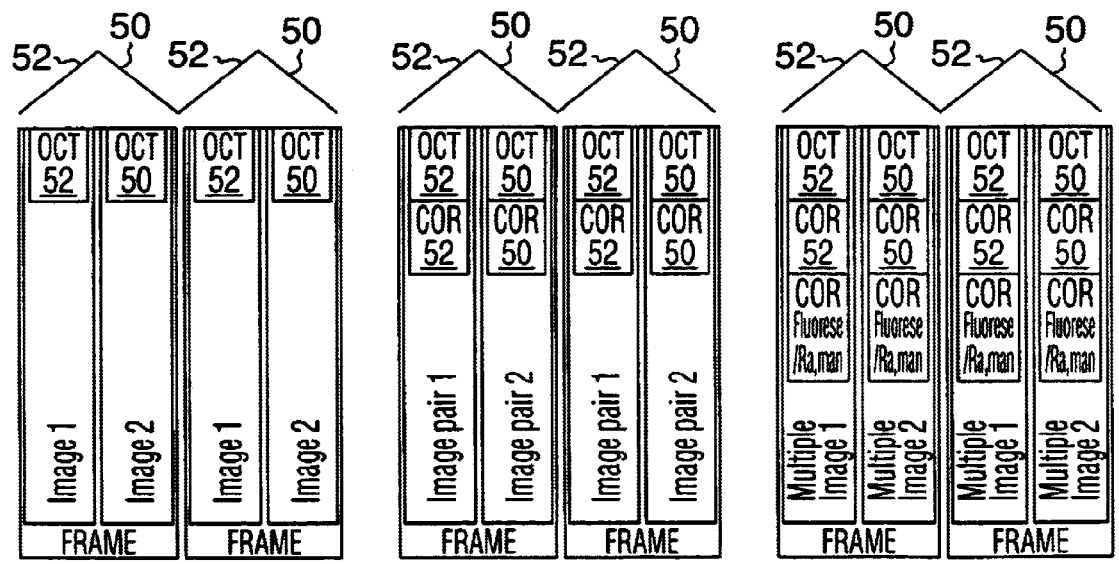
FIG. 11b(ii)

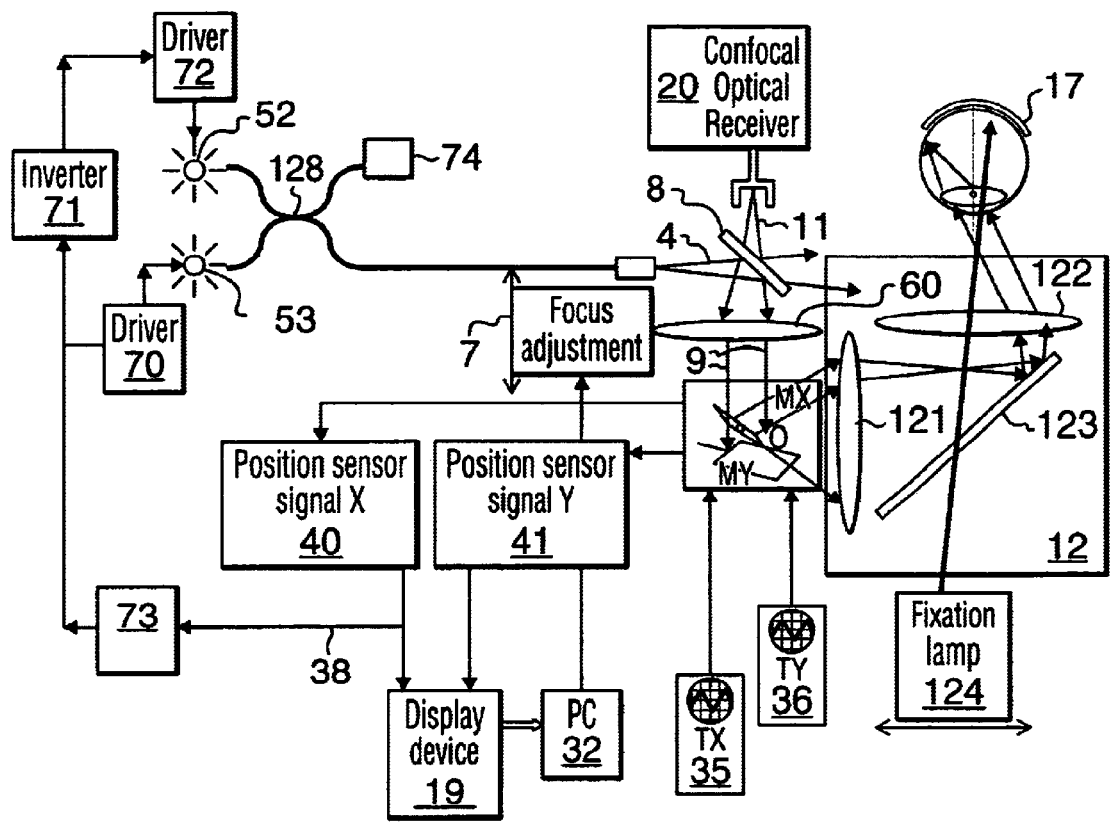
FIG. 11c (i)
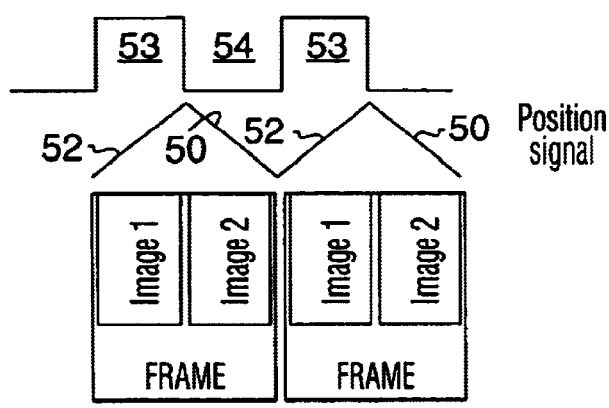
FIG. 11c (ii)

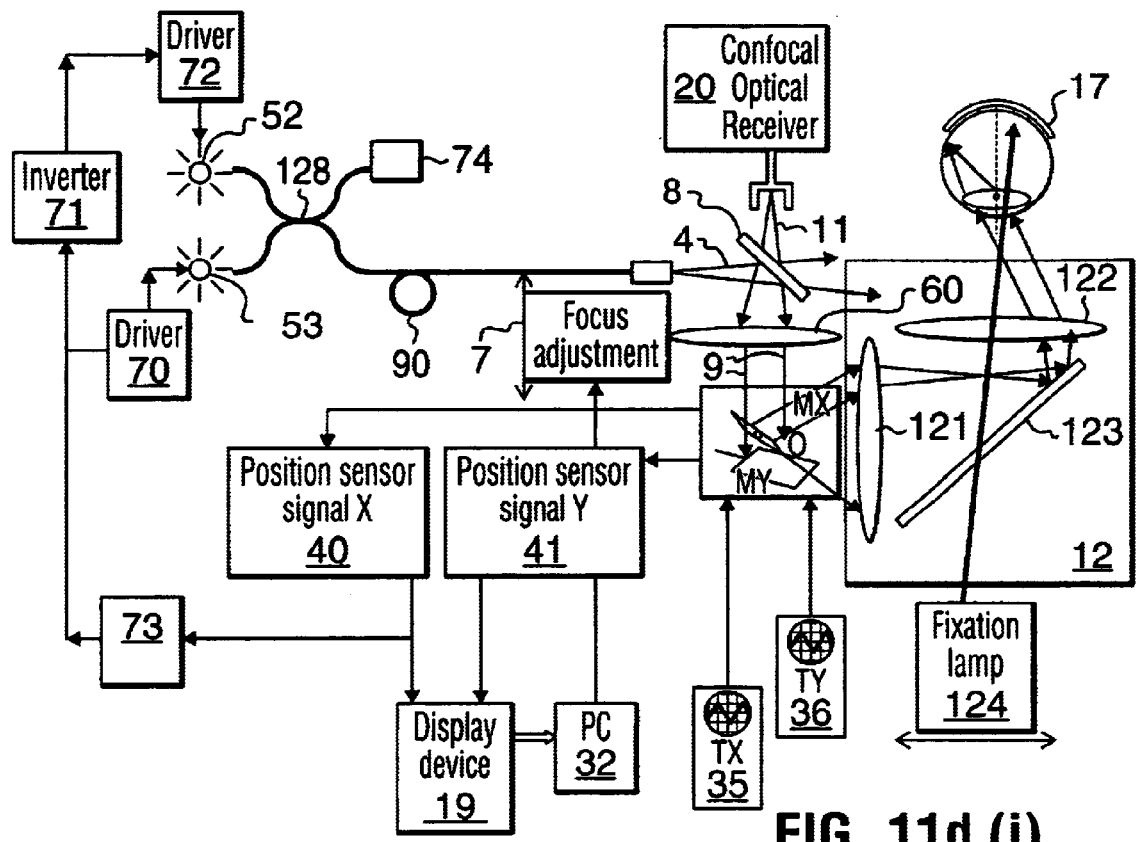
FIG. 11d (i)
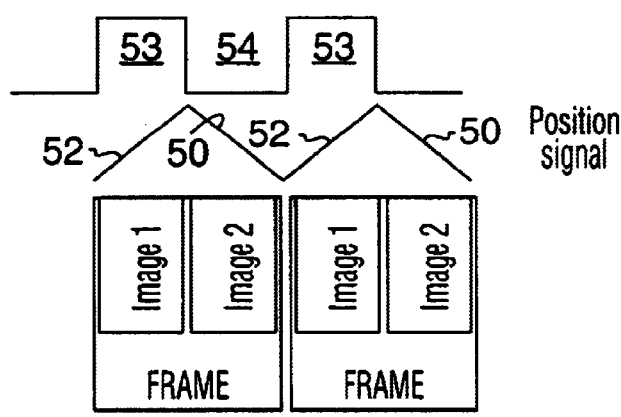
FIG. 11d (ii)

| Beam-splitter | Regime source 126 controlled by K1 | Regime operation when using a single COR 20 | | Regime operation when using the CE block 200 | |
|---|---|---|---|---|---|
| 83<br>cold or hot mirror or edge filter, cut-off between the wavelength of the low coherence source, 50 (500) and the fluorescence or Raman | Pos. 2, switched via 38, 71 and 75 | Quasi-simultaneous OCT and fluorescence or Raman would be disturbed by the excitation source if left on during the acquisition of the OCT signal | | Possible additional CORs on the OCT wavelength, possible additional CORs on bands due to sources 120 | |
| 82<br>band-pass for the configuration R-OCT/T-C(E) as shown above or a notch filter for the configuration T-OCT/R-C(E), in both cases tuned on the fluorescence or Raman wavelength | Pos. 2, switched via 38, 71 and 75 | Quasi-simultaneous OCT and fluorescence or Raman would be disturbed by the excitation source if left on during the acquisition of the OCT | | Additional COR on the OCT wavelength, sources 120 not possible to be used. | |
| 83<br>cold or hot mirror or edge filter, cut-off between the wavelength of the low coherence source, 50 (500) and the fluorescence or Raman | Pos. 1, 75 on, CW | Quasi-simultaneous OCT and fluorescence or Raman, OCT not disturbed by the excitation source | | Possible additional CORs on the OCT wavelength, possible additional CORs on bands due to sources 120 | |
| 82<br>band-pass for the configuration R-OCT/T-C(E) as shown above or a notch filter for the configuration T-OCT/R-C(E), in both cases tuned on the fluorescence or Raman wavelength | Pos. 1, 75 on, CW | OCT and fluorescence on sufficiently distant away wavelengths | | Additional COR on the OCT wavelength, sources 120 not possible to be used. | |

FIG. 12a (ii)

| Beam-splitter position | Regime source 50 (500) controlled by K2 | Regime source 126 controlled by K1 | Regime operation when using a single COR 20 | | Regime operation when using the CE block 20 |
|---|---|---|---|---|---|
| 83 cold or hot mirror or edge filter, cut-off between the low coherence wavelength of the low coherence source, 50 (500) and the fluorescence or Raman | Switched via 38, Pos. 2 | Switched via 38, 71 and 75 pos. 2 | Triple imaging regime, quasi-simultaneous OCT and fluorescence plus confocal residual image on the low coherence wavelength, when the OCT is disturbed by the excitation source of the fluorescence | | Possible additional COR on the OCT wavelength, possible additional CORs on bands due to sources 120 |
| 82 band-pass for the configuration R-OCT/T-C(E) as shown above or a notch filter for the configuration T-OCT/R-C(E), in both cases tuned on the fluorescence or Raman wavelength | Switched via 38, Pos. 2 | Switched via 38, 71 and 75 pos. 2 | Triple imaging regime, quasi-simultaneous OCT and fluorescence plus confocal residual image on the low coherence wavelength, when the OCT is disturbed by the excitation source of the fluorescence | | Additional tuned COR on the OCT wavelength, sources 120 not possible to be used. |
| 83 cold or hot mirror or edge filter, cut-off between the low coherence wavelength of the low coherence source, 50 (500) and the fluorescence or Raman | Switched via 38, Pos. 2 | Pos. 1, 75 on, CW | Triple imaging regime, quasi-simultaneous OCT and fluorescence plus confocal residual image on the low coherence wavelength, OCT not disturbed by the excitation source | | Possible additional CORs on the OCT wavelength, possible additional CORs on bands due to sources 120 |

FIG. 12b (ii)

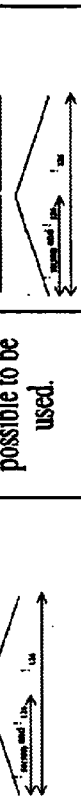
FIG. 12b (iii)

OPTICAL MAPPING APPARATUS WITH ADJUSTABLE DEPTH RESOLUTION AND MULTIPLE FUNCTIONALITY

FIELD OF THE INVENTION

The present invention relates to a dual channel optical mapping apparatus and to methods which can be used to supply images from essentially transparent objects or tissue using different depth resolutions, or, sequentially, images with adjustable depth resolution at the same or at different wavelengths, as required to observe fluorescence or Raman radiation emitted by the object. The two channels of the dual channel apparatus could be either a confocal channel and an optical coherence tomography channel, two optical coherence tomography channels, or two confocal channels.

BACKGROUND OF THE INVENTION

In the description which follows, reference is made primarily to the eye as the object. This has to be understood as merely a way to help the description and not as a restriction of the application of the present invention. As such, where the term "eye" is used, a more general transparent and scattering object or organ may be sought instead.

High depth resolution imaging of the eye fundus can be achieved by optical coherence tomography (OCT) as shown in the paper "Optical coherence tomography" by D. Huang, E. A. Swanson, C. P. Lin, J. S. Schuman, W. G. Stinson, W. Chang, M. R. Hee. T. Flotte, K. Gregory, C. A. Puliafito and J. G. Fujimoto, Science 254, (1991), pp. 1178 and in the paper "Optical coherence tomography" by A. F. Fercher, in J. Biomed. Opt., 1(2), (1996), pp. 157–173. OCT has the potential of achieving much better depth resolution, as the limit in this case is not set by the eye, but by the coherence length of the source. For example, optical sources, such as superluminiscent diodes and mode-locked lasers are now available with coherence lengths below 20 $\mu$m.

An OCT apparatus is now commercially available (e.g. from Humphery), which produces longitudinal images only, i.e. images in the planes (x,z) or (y,z), where the z axis is perpendicular to the patient's face and x and y axes are in the plane of the patient's face. Examples of such apparatus for longitudinal imaging are described in U.S. Pat. Nos. 5,493,109, 5,537,162, 5,491,524, 5,469,261, 5,321,501 and 5,459,570.

OCT has also been reported as being capable of providing en-face (or transversal) images, as reported in "Coherence Imaging by Use of a Newton Rings Sampling Function" by A. Gh. Podoleanu, G. M. Dobre, D. J. Webb, D. A. Jackson, published in Opt. Lett., Vol. 21, No. 21, (1996), pp. 1789–1791, "Simultaneous En-face Imaging of Two Layers in Human Retina" Opt. Letters, by A. Gh. Podoleanu, G. M. Dobre, D. J. Webb, D. A. Jackson, published in Opt. Lett., 1997, vol.22, No. 13, pp. pp. 1039–1041 and "En-face Coherence Imaging Using Galvanometer Scanner Modulation" by A. Gh. Podolenu, G. M. Dobre, D. A. Jackson, Opt. Lett. 23, pp. 147–149, 1998. When applied to the eye, however, the en-face OCT images look fragmented, as demonstrated in "Transversal and Longitudinal Images from the Retina of the living Eye Using Low Coherence Reflectometry", by A. Gh. Podoleanu, Mauritius Seeger, George M. Dobre, David J. Webb, David A. Jackson and F. Fitzke, published in the Journal of Biomedical Optics, 3(1), pp. 12–20, 1998. These papers also demonstrate that, owing to the low coherence length, the OCT transversal images show only fragments of the retina and are difficult to interpret.

To improve the usefulness of en-face OCT images, a dual presentation of images was proposed as described in U.S. Pat. No. 5,975,697. Two en-face images are produced and displayed simultaneously; one of which is an OCT image and the other is a confocal image (similar to the image produced by a scanning laser ophthalmoscope (SLO)). The dual presentation allows the fragments sampled by the OCT of the fundus to be uniquely placed in correspondence with fundus images displayed by the confocal channel. The confocal channel, however, has a much larger depth resolution and the images look continuous, offering good guidance of the part of the eye investigated.

The dual display is generally essential not only for guidance, but for subsequent alignment and processing of the stack of en-face images prior to reconstruction of the 3D volume investigated. In addition, it enables the same location in the eye to be accessed easier on subsequent examinations. However, a practical problem of the dual channel imaging instruments is that focusing has to be adjusted simultaneously for both channels. No provisions were presented in U.S. Pat. No. 5,975,697 with respect to this feature.

Another problem with the prior art technique is that the confocal channel taps some of the possibly already weak return signal from the tissue, which results in a lower signal to noise ratio in the OCT channel. For instance, when 10% of the signal is tapped, the loss in the OCT channel can be more than 19%. Therefore, it would be desirable, especially when the target returns a weak signal, to eliminate confocal tapping and return all of the signal to the OCT channel. On the other hand, there are situations when the presentation of an OCT image is not needed and depth analysis using the confocal channel only may be required. Unfortunately, however, the beam-splitter ratio in U.S. Pat. No. 5,975,697 is fixed and therefore, such versatility cannot be achieved.

Another problem is that when this technique is used for OCT of skin or teeth, longer wavelengths are recommended for providing better penetration depth. However, the gain of photocathodes and avalanche photodetectors at longer optical wavelengths is much poorer than that for visible light or, for example, the 800 nm band which is preferred for the retina. Therefore, at longer wavelengths, poorer performance of the confocal channel of the dual instrument as presented in U.S. Pat. No. 5,975,697 is expected. Another problem with the dual channel imaging instrument as described in U.S. Pat. No. 5,975,697 is that the wavelengths of the two channels are the same. The system as such cannot be used to generate a confocal image at a different wavelength from that used in the OCT channel. This prevents the utilisation of the system in fluorescence and autofluorescence imaging, or for Raman studies.

In U.S. Pat. No. 5,459,570, the beam-splitter shared by the confocal and the OCT channel is used in transmission. It is known that the dispersion of the optical material used in beam-splitters, if left uncompensated, leads to deterioration of the depth resolution in the OCT channel. An on-axis fixation lamp is also required for the investigation of the fovea. This requires other beam-splitters to be introduced in the system, which adds further dispersion to the OCT channel.

A still further problem with en-face scanning using galvanometer scanners is that the fly-back of the galvanometer scanner is finite and consequently, more than 20% of the period time of the ramp signal driving the galvanometer scanners, at kHz rates, may be wasted.

In terms of transverse resolution, this feature depends on how well the focus is matched to the coherence position (wherein tracking of the focusing and zero optical path difference are referred to as dynamic focus). Dynamic focus was described in PCT patent publication No. WO 92/19930, but only in principle. Possible optical configurations to simultaneously scan the depth and the position of the focus in the depth are described in U.S. Pat. No. 4,589,773 and in U.S. Pat. No. 6,057,920. These solutions however, require mechanical synchronism of elements or adjustment of ratios of focal lenses. The prior art method works only when the index of refraction of the tissue is known. If the tissue consists of layers of different index of refraction, different adjustments are required. The methods described are devised especially for longitudinal OCT, where B-scan images are generated by fast scanning along the depth coordinate with a slower scanning along a transverse coordinate. As such, the method needs to be fast, and operational at the depth scanning rate of, for example, a rate on the order of 100–1000 Hz. Once different solutions have been devised as described in U.S. Pat. No. 6,057,920, it is very difficult to reconfigure the technique for different values of the refractive index or to apply corrections for multiple layers of different index of refraction.

Another mechanical configuration is disclosed in U.S. Pat. No. 6,201,608, however this method is not applicable for use with the eye.

U.S. Pat. No. 6,172,752B1 discloses a low coherence interferometer where the thickness and the index of refraction of a transparent plate can be determined by measuring the displacement of the plate, or of the lens in the front of the plate in the object arm and of the mirror in the reference arm. The method uses these displacements and the numerical aperture of the beam entering the sample. However, when imaging different layers in the scattering tissue, the index of refraction is unknown and the method is not applicable as no tracking mechanism of the two displacements is described. Additionally, when imaging tissue and the eye, the interface optics complicates the equation which relates the two displacements to be tracked, and additionally, the patients have different eye lengths (i.e. the numerical aperture is not known and the method again is not applicable).

Thus, a need exists for better procedures of implementing dual channel imaging with different depth resolution, which procedures can allow imaging at different wavelengths and allow for focusing adjustment to be tracked in both channels while being compatible with dynamic focus in order to maintain both channels in focus. In particular, better procedures having improved efficiency and which make better use of scanning devices and of the sensitivity of photodetectors, and which can allow for versatile operation of the two channels to cover a large range of possible imaging regimes with the same hardware, are desirable. Accordingly, the present invention provides for improvements over at least one of the problems of the prior art as stated hereinabove, or as described hereinbelow.

SUMMARY OF THE INVENTION

As a first advantage, the present invention sets out to solve the above discussed problems and relates to an apparatus wherein both receiver apertures (e.g. OCT and confocal) are maintained in focus.

In a second advantage, the present invention sets out methods and apparatuses to ensure that the confocal optical receiver operates at the maximum sensitivity.

In a third advantage, the present invention sets out methods and apparatuses which allow:

(i) switching from a dual OCT/confocal regime to a predominantly single channel operation regime of either OCT only, or of a predominantly confocal regime (with only minor sensitivity loss to the OCT channel), wherein by balancing the signals returned from the object to the OCT and confocal channels either: (a) complete extinction of the signal returned from the object towards the confocal channel is possible; or (b) a significant reduction of the signal returned to the OCT channel is possible while maximising the signal returned to the confocal channel;

(ii) or operation in a mode having two confocal channels imaging at two different wavelengths.

In a fourth advantage, the invention sets out methods and apparatuses to quasi-simultaneously produce two images of different depth resolution from the same depth.

In a fifth advantage, the invention sets out methods and apparatuses to quasi-simultaneously produce two images at two different wavelengths, as required for the observation of auto-fluorescence or fluorescence, or Raman in the object under investigation.

In a sixth advantage, the invention sets out methods and apparatuses to generate pairs of images or an image, where the pixel position is determined within the raster (or image display) by the actual coordinates of the transversal scanners, irrespective of the movement direction of the transversal scanners. Alternatively, the invention sets out methods and apparatuses to generate double pairs of images for each direction of movement of the transversal scanners.

In a seventh advantage, the invention sets out methods and apparatuses to process and eventually superimpose the OCT image on to the confocal image, of the same or different wavelength, or to produce, process and eventually superimpose OCT images of different depth resolutions, from the same depth.

In an eighth advantage, the invention sets out methods and apparatuses to track the focus in the OCT and confocal channel with the depth scanned in the OCT channel.

The advantages set out hereinabove, as well as other objects and goals inherent thereto, are at least partially or fully provided by an improved optical mapping apparatus of the present invention, having improved focusing means, a versatile optical splitter shared by the confocal and OCT channel and switched optical sources synchronised with imaging means.

Accordingly, in a first aspect, the present invention provides an optical mapping apparatus which comprises:

an optical coherence tomography (OCT) system built around an in-fiber or a bulk interferometer excited by an optical radiation source;

a confocal optical receiver with or without adjustable depth resolution;

an optical splitter, shared by both the interferometer of the OCT and the confocal optical receiver, to direct some of the light returned from an object situated at the object location to the optical confocal optical receiver, where the OCT channel uses the optical-splitter in reflection and the confocal channel in transmission, —regime called as "Reflection—OCT/Transmission—Confocal", hereinafter "R-OCT/T-C" or optionally wherein the OCT channel uses the optical-splitter in transmission and the confocal channel uses the optical splitter in reflection, —regime called "Transmission OCT/Reflection-Confocal", hereinafter "T-OCT/R-C";

transverse scanning means, preferably consisting of a line scanner and a frame scanner, to effect transverse scanning of an optical output from the optical splitter (as an imaging beam), over a line or a predetermined area in the object;

interface optics for transferring an optical beam from the transverse scanning means to the object and for transferring an optical output beam reflected and scattered from the object back to the optical-splitter through the transverse scanning means, and from the optical-splitter to both the interferometer of the OCT channel and/or the optical confocal optical receiver of the confocal channel, in a ratio determined by the optical splitter and wavelength;

optionally a fixation lamp for sending light from an external source towards the object;

optionally all interface optics-splitter shared by the fixation lamp beam and the imaging beam, wherein the interface optics-splitter can be used either in reflection or transmission by the imaging beam while respectively the fixation lamp beam is transmitted or reflected, respectively;

focusing adjustment means placed between the optical-splitter and the transverse scanning means, to simultaneously maintain the input aperture of the interferometer and the aperture of the confocal optical receiver in focus, while focusing the scanned beam on the object;

optionally means to introduce intensity or phase modulation or intensity modulation and phase modulation in the said OCT interferometer;

analysing means, coupled to the raster scanning means, for demodulating the photodetected signals of the photodetectors in the interferometer and confocal optical receiver;

optionally depth adjustment means for altering the optical path difference in said OCT interferometer, over a predetermined amount for at least one point in the raster in either steps or continuously at a pace synchronised with the focusing adjustment means, according to a synchronising procedure;

displaying means for processing and generating an image created by the interferometer and an image created by the confocal optical receiver for the simultaneous display of the said respective images created by the interferometer and the confocal optical receiver, which images are synchronised with the transverse scanning means;

optionally timing means which control two main operation regimes, namely (i) en-face imaging when the mapping apparatus acquires transverse images in a plane perpendicular on the optic axis (or in the patient face) at constant depth for different depths and (ii) longitudinal imaging when the mapping apparatus acquires longitudinal images containing the optic axis (or perpendicular to the patient face).

In a preferred feature, the optical mapping apparatus is as described hereinabove wherein said confocal optical receiver is part of a block CE, which consists of at least one confocal optical receiver with or without adjustable depth resolution and optionally, at least one excitation source to excite fluorescence or Raman radiation from the object, whole the aperture of the block CE is optically conjugate to the apertures of the confocal optical receiver and of the excitation source; and wherein:

said optical splitter, shared by both the interferometer of the OCT and the block CE, directs some of the light returned from an object situated at an object location adjacent to the optical mapping apparatus, wherein, the OCT channel uses the optical-splitter in reflection and the block CE in transmission (R-OCT/T-CE), or wherein the OCT channel uses the optical-splitter in transmission and the CE block uses the optical splitter in reflection (R-OCT/R-CE);

said interface optics transfers an optical beam from the transverse scanning means to the object, and an optical output beam reflected and scattered from the object back to the optical-splitter through the transverse scanning means, and, from the optical-splitter to the interferometer of the OCT channel and to the block CE in a selected ratio, which ratio is determined by the optical splitter used and the wavelength of the radiation backscattered or emitted by the object; and said focusing adjustment means is placed between the optical-splitter and the transverse scanning means, to simultaneously maintain the input aperture of the interferometer and the aperture of the CE block in focus, while focusing the scanned beam on the object.

Further, the optical mapping apparatus is preferably one wherein said optical radiation source is made out of two optical sources of different wavelengths which are combined by a fiber directional single mode coupler or a bulk beam-splitter;

said depth adjustment means alters the focus, over a predetermined amount for at least one point in a raster in either steps or continuously at a pace synchronised with the focusing adjustment, according to a synchronising procedure;

said displaying means for generating and processing the images created by the confocal optical receivers, is synchronised with the transverse scanning means, wherein a line in the image corresponds to the line scanner movement and the advance of said line to the completion of the area scanned corresponds to the movement of the frame scanner; and said timing means controls the 3D scanning operation regime, when the mapping apparatus acquires en-face images in a plane perpendicular on the optic axis (or in the patient face) at different focusing depths.

In a further preferred feature, the transverse scanning means comprises a line scanner and a frame scanner, and still further, wherein a line in an object corresponds to the line scanner movement and the advance of the line to the completion of the area scanned corresponds to the movement of frame scanner. Still more preferably, the analysing means is coupled to the transverse scanning means.

The optical radiation source is preferably a low coherence source, or a source with adjustable coherence length.

Further, it is preferred that the depth adjustment means and the focusing adjustment means use synchronised PC controlling means, with independent initial position, velocity and acceleration and deceleration, which can be controlled continuously or in a stepwise manner.

Further, in one preferred embodiment, the present invention provides an optical mapping apparatus which comprises:

an optical coherence tomography (OCT) system built around an in-fiber or a bulk interferometer excited by an optical radiation source;

transverse scanning means consisting from a line scanner and a frame scanner to effect transverse scanning of the object using an optical output from the optical splitter (as an imaging beam), over a line or a predetermined area in the object;

interface optics for transferring an optical beam from the transverse scanning means to the object, and for transferring an optical output beam reflected and scattered from the object back to the OCT system;

optionally a fixation lamp for sending light from an external source towards the object;

optionally, an interface optics-splitter shared by the optional fixation lamp beam and the imaging beam, wherein the interface optics-splitter can be used either in reflection or transmission by the imaging beam, while the fixation lamp beam is transmitted or reflected, respectively;

focusing adjustment means placed between the output of the OCT system and the transverse scanning means, to maintain the input aperture of the interferometer in focus, while focusing the scanned beam on the object;

optionally means to introduce intensity or phase modulation or intensity modulation and phase modulation in the OCT interferometer;

analysing means, coupled to the transverse scanning means, for demodulating the photodetected signals of the photodetectors in the interferometer;

depth adjustment means for altering the optical path difference in said OCT interferometer over a predetermined amount for at least one point in the transverse scanning means in either steps or continuously at a pace synchronised with the focusing adjustment means, according to a synchronising procedure;

displaying means for generating and processing the image created by the interferometer synchronised with the transverse scanning means, where the line in the image corresponds to the line scanner movement and the advance of the line to the completion of the area scanned corresponds to the movement of the frame scanner;

optionally timing means which control two main operation regimes, namely (i) en-face imaging when the mapping apparatus acquires transverse images in a perpendicular plane at constant depth and (ii) longitudinal imaging when the mapping apparatus acquires longitudinal images in a parallel plane.

In a further aspect, the present invention also provides a method of preparing a dual channel image of an object, which method utilizes an optical mapping apparatus as described hereinabove with respect to the present invention, or as described hereinbelow.

In a still further aspect, the present invention also provides for the use of the apparatus described hereinabove with respect to the present invention.

BRIEF DESCRIPTION OF THE DRAWINGS

Other features of the present invention, as well as other objects and advantages attendant thereto, are set forth in the following description and the accompanying drawings in which like reference numerals depict like elements. Accordingly, various embodiments of the optical mapping apparatus of the present invention will now be described by reference to the following drawings wherein:

FIG. 4 shows in diagrammatic form, different implementations of the confocal optical receiver as part of an optical mapping apparatus with adjustable depth resolution;

FIG. 9a shows in diagrammatic form, another embodiment of the optical mapping apparatus with adjustable depth resolution according to the invention, with a quasi-simultaneous display of two images of different depth resolution, obtained by using two sources on the same or close wavelengths but with different coherence lengths;

FIG. 10 shows images collected from skin with the apparatus embodiment described in FIG. 9a, namely where two pairs of images are displayed which have been generated with sources of different coherence length;

FIG. 11b shows in diagrammatic form, another embodiment of the optical mapping apparatus with adjustable depth resolution according to the invention where the image coordinate is controlled by position sensitive detectors of the angular deviation of the transverse scanners to quasi-simultaneously display two images with different depth resolution while using two sources on the same or close wavelengths but with different coherence lengths or two sources of different wavelengths, at least one of low coherence;

FIG. 11c shows in diagrammatic form, a different embodiment of the optical mapping apparatus according to the invention where the image coordinate is controlled by position sensitive detectors of the angular deviation of the transverse scanners to quasi-simultaneously display two confocal images while using two sources of different wavelength;

FIG. 11d shows the embodiment of the optical mapping apparatus in FIG. 11c using a polarisation sensitive optical-splitter;

DETAILED DESCRIPTION OF THE PREFERRED EMBODIMENTS

Figure 1:
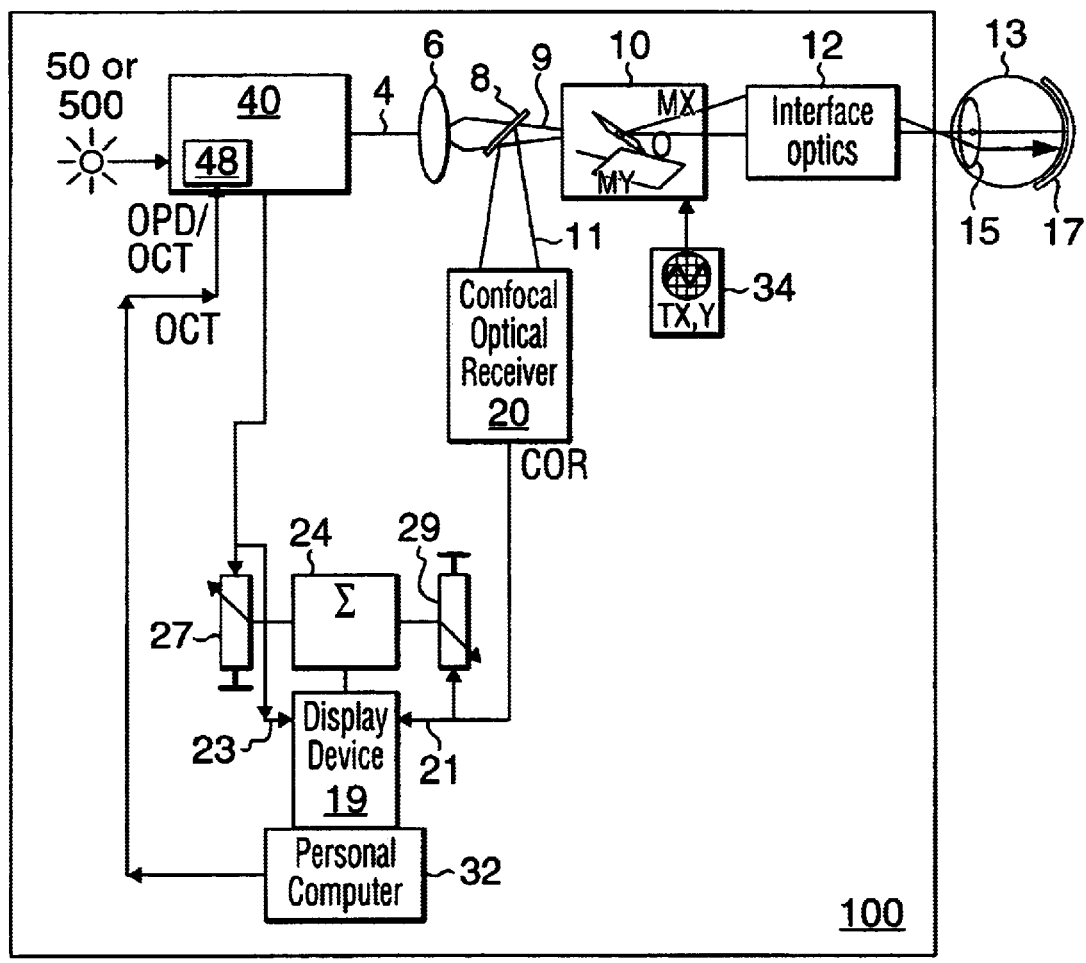
FIG. 1 is prior art and shows, in diagrammatic form, the main elements of an optical mapping apparatus with adjustable depth resolution and two channels (namely OCT and confocal), which has been previously described in U.S. Pat. No. 5,975,697.

Various features of the present invention, as well as other objects and advantages attendant thereto, are set forth in the following description and the accompanying drawings in which like reference numerals depict like elements.

Where optical fibers are used, this is only as an example and it should be noted that a bulk implementation is equally feasible, in which case the respective elements in the examples using fiber version components, are to be replaced by optical paths and the couplers by plate beamsplitters.

An OCT device involves and makes use of techniques known in the art and as described in U.S. Pat. Nos. 5,459,570, 5,321,501, 5,491,524, 5,493,109, 5,365,335, 5,268,738, and 5,644,642. These devices can be constructed in bulk or optical fiber, and have means for transversally scanning the target, means for longitudinal scanning of the reference path length, means for phase modulation, means for controlling the polarization stage as bulk or fiber polarizer controllers, and have means for compensating for dispersion.

FIG. 1 diagrammatically shows the main elements of an optical mapping apparatus with adjustable depth resolution, according to U.S. Pat. No. 5,975,697. The apparatus 100 comprises an OCT interferometer 40 excited by a source which can be either low coherence, designated as 50, or with adjustable coherence length, designated as 500. In the context of the invention, a source with low coherence is a broadband source, whose coherence length is much less than the penetration depth of the radiation used in the object studied. Examples of such sources include superluminiscent diodes, tungsten lamps, Kerr-lens mode-locked lasers, laser diodes below threshold and diverse combinations of the above. For instance, at the level of the technology today, the coherence length of such sources cover the range of 1–500 $\mu$m. In contrast, in the context of the invention, a high coherence source has a coherence length much larger than the penetration depth of the radiation used in the object studied. Examples of such sources include lasers, with coherence length larger than 1 cm.

An OCT sample beam 4 is outputted from OCT interferometer 40, using a single mode fibre if the OCT interferometer is in fibre, or if it is in bulk, 4 is a free space optical output beam. The OCT sample beam output 4 is focused by an optical element 6, such as a refractive or reflective optical element, split by an optical-splitter 8 into a beam 9 which is then deflected by a 2D scanner head 10 to scan transversally, via interface optics 12, an object 13. In FIG. 1 the object is the retina 17 of an eye 13, the beam being focused by the eye lens 15 onto the object.

Scanner head 10 is a scanning assembly means known in the art and includes, for example, galvanometer scanners, polygon mirrors, resonant scanners, acousto-optic modulators, rotating or vibrating prisms etc. The scanner head 10 is under the control of triangle, sawtooth or DC voltages produced by a generator 34. Combinations of scanners from the list above can be used for the head 10. One scanner usually works fast and the signal collected during its movement is displayed on the line in the raster, termed as the line scanner, while the other scanner, is typically termed as frame scanner. For instance, a polygon mirror can be used as the line scanner and a galvanometer scanner can be used as the frame scanner.

The path 4 and path 9, along with the scanning head 10 and interface optics 12 define an object path, returning the object signal. The scanning head 10 can be divided in two parts, namely the line scanner and the frame scanner, separated by optical elements like lenses and/or mirrors in configurations known in the SLO art and confocal microscopy or general raster scanning systems, in which case the scanner 10 and interface optics 12 are interleaved to each other, in one block, and only for convenience are they represented here separately. The scanner mirrors, Mx and My, which refer to either galvanometer scanners or polygon mirrors have high reflectivity at the wavelength used, or if acousto-optic modulators are used, their transmission at the wavelength used is high. By means known in the art, the two scanners have orthogonal axes or scan the ray in perpendicular planes, producing a raster in the plane (X,Y), oriented perpendicular on the optic axis of the system. Circular scan, ($\rho,\theta$) of the ray can also be obtained by sinusoidally scanning the ray using the two scanners in orthogonal directions at the same frequency with a phase difference of $\pi/2$, where $\rho$ is determined by the amplitude of the angular deviation, measured in a plane perpendicular on the optic axis of the system from the point hit by the ray when the scanners are not driven, and $\theta$ is a polar angle in this plane.

The object signal interferes with the reference signal when the optical path difference (OPD) between the reference path and object path is less than the coherence length of the source 50. This explains the selection in depth of the OCT. Points along the object beam in the volume of the object will contribute to the signal only from within the coherence length of the source in the volume of the object.

The light returned by the object, reflected and scattered, is partly collected via the focusing element 6 back into the path 4 and partly, transmitted as a beam 11, which is collected by a confocal optical receiver (COR) 20. A signal delivered by the OCT, 23, and a second signal delivered by the COR at its output, 21, are weighted respectively by potentiometers 27 and 29 at the inputs of a summator 24. The resultant signal is then displayed and recorded by means of a suitable display device 19, such as a frame grabber, a storage oscilloscope or a suitable printer. The device 19 is under the control of computer 32.

The resultant images can be displayed in linear or logarithmic scale on grey or false colour coded format. When the OCT and COR images are to be displayed separately, a special device 19 with dual display capabilities is required, such as a dual channel variable scan frame grabber. The depth in the OCT channel is scanned by changing the optical path in the object or reference beam of the interferometer, 40, using depth scanning means, 48, controlled by computer 32 in a PC controlled translation stage or, alternatively, controlled by galvanometer scanners in configurations of lenses as described in U.S. Pat. No. 5,975,697 or by any other means to controllably move a mirror or groups of mirrors, or prisms, by any means known in the art., or alternatively, by using galvanometer scanners and gratings as described in U.S. Pat. No. 6,111,645.

Figure 2A:
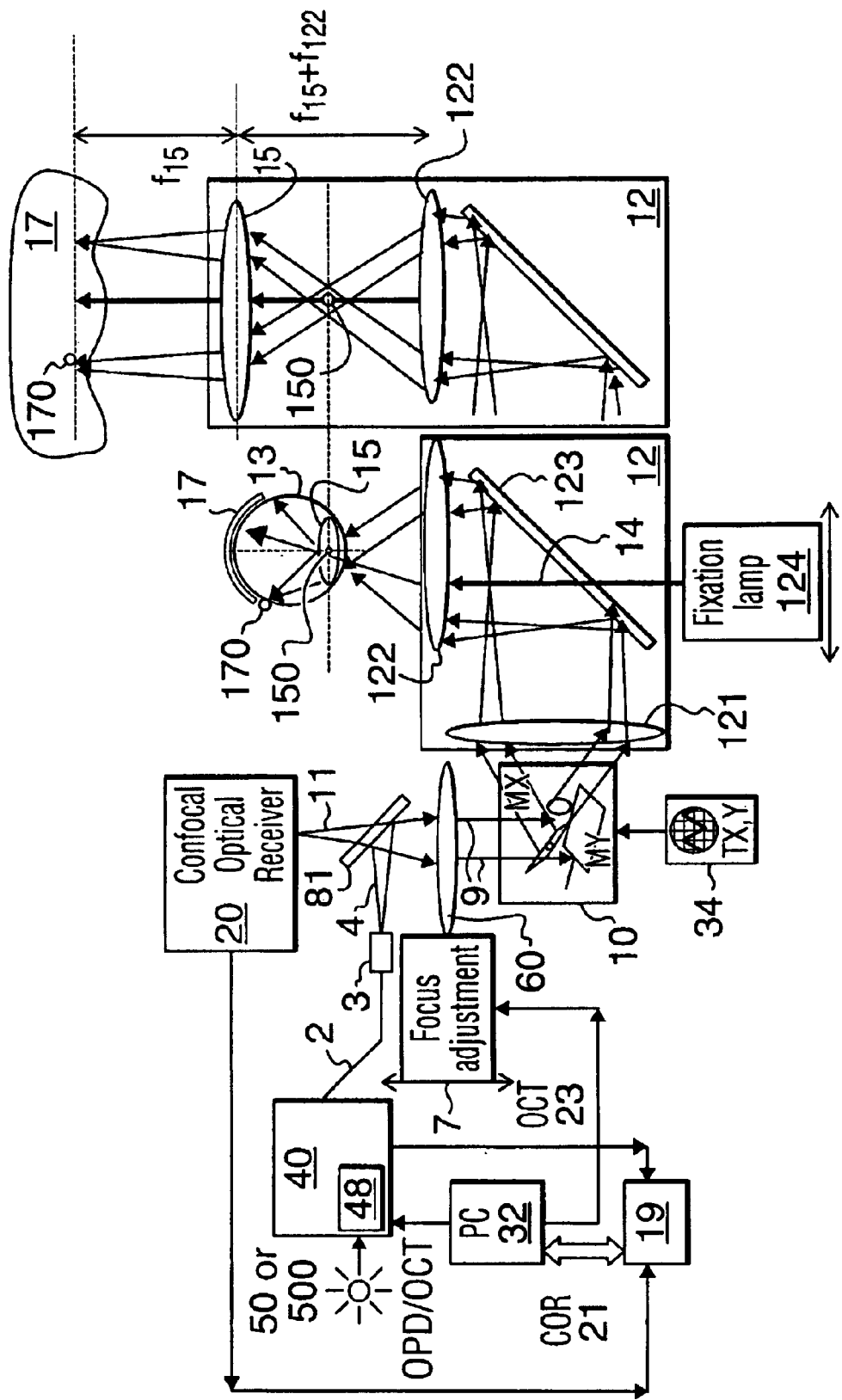
FIG. 2a shows, in diagrammatic form, a first embodiment of the focusing configuration which allows simultaneous focus adjustment to maintain both receiver apertures (OCT and confocal) in focus, when focusing the beam on the retina in an eye, as well as a variation showing an alteration of the interface optics to focus the beam on the skin.

FIG. 2a shows, in diagrammatic form, the main elements of a dual channel OCT/confocal apparatus according to the invention where both receiver apertures, namely OCT and confocal, are maintained in focus. FIG. 2a to 2d refer to a particular case where the beam out of the OCT, expands out of a fiber 2, or a bulk spatial filter, and the numerical aperture is then accommodated by a lens or a spherical mirror behind the optical splitter. For this goal, the adjusting focusing element. i.e. the lens 6 in FIG. 1, is now placed after the optical-splitter 8, and is re-numbered as lens 60. The fiber end tip, 3, and the confocal optical receiver aperture (usually considered the pinhole 202 (see FIG. 4)) of the confocal optical receiver 20 are at equal distances from optical-splitter, 8 and in the focus of the lens 60. By mowing the lens, 60, to adjust the focus, the beam 9 can be made divergent or convergent. When the object is the retina, for the case of an emmetropic eye, the beam 9 is collimated. Irrespective of the case, emmetropic or ammetropic, both the fiber tip, 3 and the confocal optical receiver aperture, 20, are conjugate to the focus inside the object, point 170, which in the case illustrated in FIG. 2a, is either the retina, 17, of a human eye, 13 (or inside the skill, 17, as shown in the lateral inset discussed hereinbelow). The wavefronts of beams 4 and 11 maintain the same radius of curvature while lens 60 is moved using focusing mechanism, 7, and thus, in this way, the focus in both channels is adjusted. For an emmetropic eye, the beam is collimated after the lens 60 with the beam collimated again after the interface optics 12. The fan of rays converges in the point 150, where when the object is the retina, the eye pupil is positioned and is focused by the eye lens, 15.

Lateral to the eye 17 depicted in FIG. 2a, the inset in FIG. 2a shows another, second possibility, wherein the apparatus is used to scan flat objects or tissue such as skin. In this example, the interface optics uses a third lens, 15, away from the point where the fan converges, 150 by the focal length of the lens 15, with the surface scanned at the same focal length of the lens 15, $f_{15}$. As known, and it will be more obvious as presented hereinbelow with respect to FIGS. 14 and 15 in connection with the explanation of the dynamic focus as described in the present invention, when the rays penetrate an object of an index of refraction n>1, the focus advances deeper inside the object.

The focusing adjustment element, 7, may be controlled from the computer, 32, to maintain the focusing in synchronism with the optical path difference adjustment (OPD) in the OCT channel 40 (control line OPD/OCT), which acts on the depth scanning means, 48.

Also shown in FIG. 2a is a hot mirror, 123, placed between lenses 121 and 122 of the interface optics, 12. The hot mirror 123 works in reflection for the apparatus imaging beam, 9, and in transmission for the beam, 14, of fixation lamp, 124. In this way, dispersion is minimised in the OCT, as both the optical-splitter, 8, and beam-splitter 123, are used in reflection.

Figure 2B:
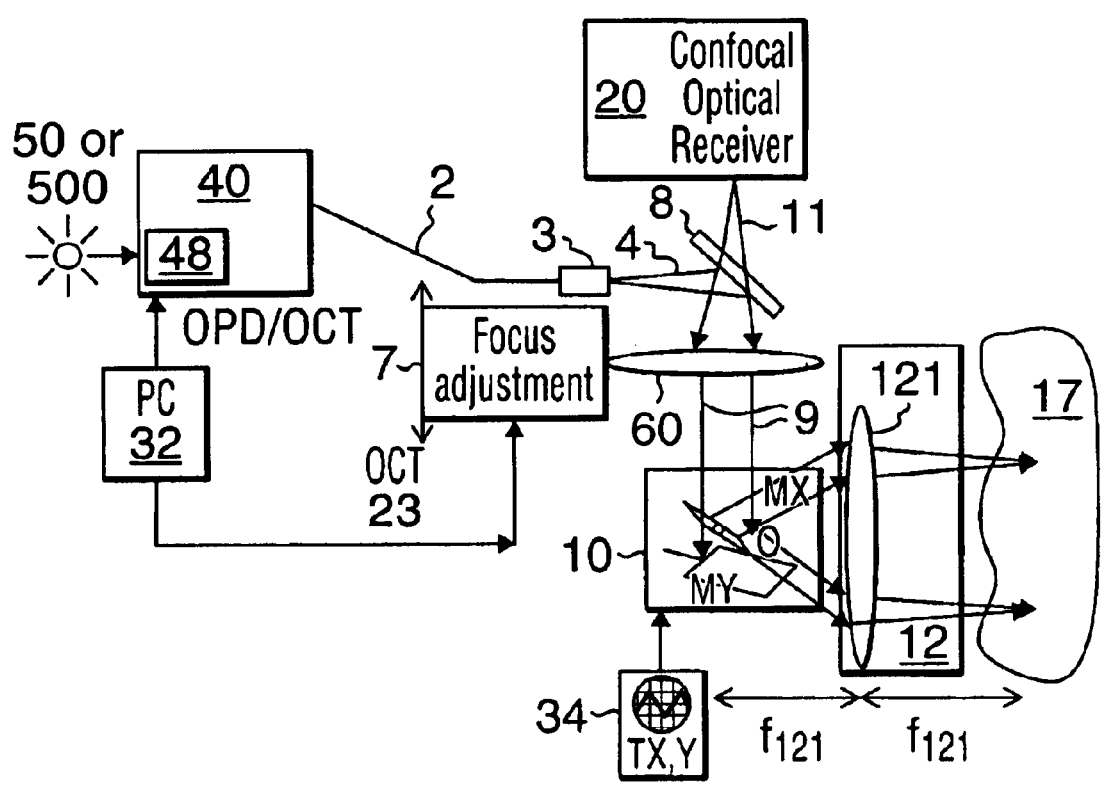
FIG. 2b shows, in diagrammatic form, another version of the first embodiment of the focusing configuration allowing simultaneous focus adjustment to maintain both receiver apertures (OCT and confocal) in focus, with simpler interface optics when focusing the beam on skin.

FIG. 2b shows an embodiment of the focusing adjustment in FIG. 2a coupled to interface optics 12 with only one lens, used merely to focus the object beam on the skin.

Figure 2C:
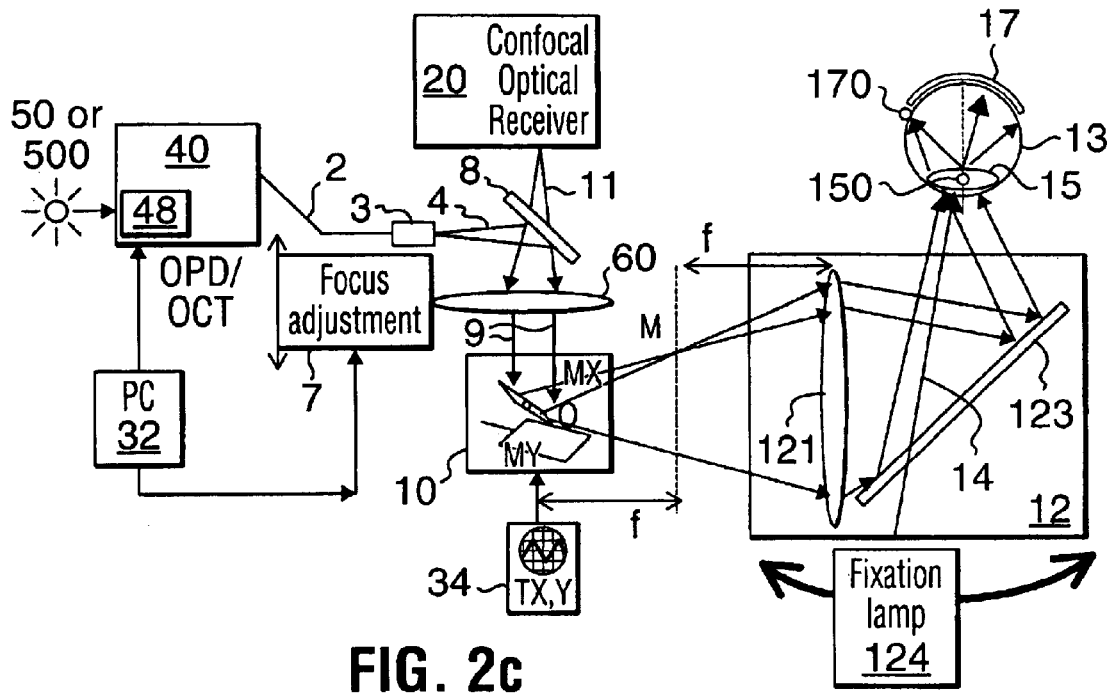
FIG. 2c shows, in diagrammatic form, another version of the first embodiment of the focusing configuration allowing simultaneous focus adjustment to maintain both receiver apertures (OCT and confocal) in focus, and to accommodate a different configuration of interlace optics, when focusing the beam on the retina in an eye.

FIG. 2c shows another version of the focusing adjustment plus interface optics, where the interface optics uses a single lens, 121, with the transverse scanning means and the pupil, point 150, conjugate in respect of the lens 121, in which case, the lens 60 is used to focus the light in the front of the lens 121, at a distance equal to its focal length f. Ideally, the distances between lens 121 to transverse scanning means 10, and between lens 121 to point 150, are $2f_{121}$. The OCT fibre aperture and the confocal optical receiver aperture are conjugate to the point 170. For focus adjustment, when the lens 60 is moved by the block 7, the point 170 moves outside the plane at $f_{121}$ in the front of the lens 121, and the focus point, 170, in the object 17 is axially shifted accordingly to accommodate a different focusing power of the eye lens, 15. Again, irrespective of the case, far sighted or near sighted eye, both the fiber tip, 3 and the confocal optical receiver aperture, 20, are conjugate to the focus inside the retina. The wavefronts of the beams 4 and 11 maintain the same radius of curvature while adjusting the focus by moving lens 60.

Figure 2D:
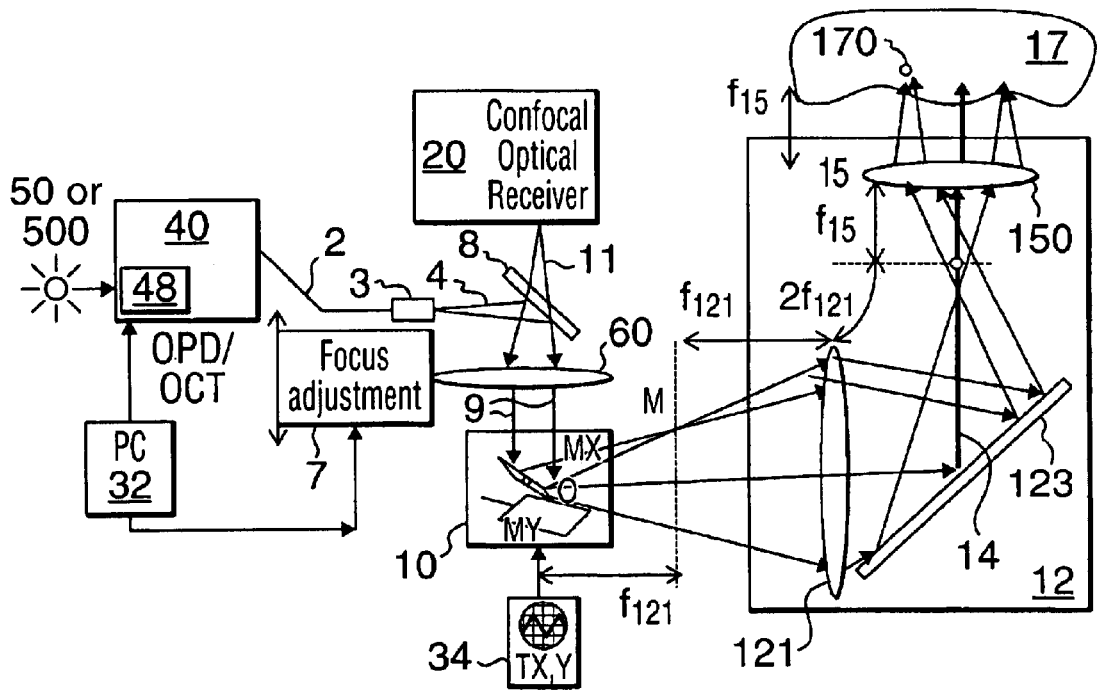
FIG. 2d shows, in diagrammatic form, another version of the first embodiment of the focusing configuration allowing simultaneous focus adjustment to maintain both receiver apertures (OCT and confocal) in focus while accommodating the configuration of interface optics in FIG. 2c to focus the beam on skin.

FIG. 2d shows an embodiment of the focusing adjustment in FIG. 2c, coupled to an interface optics with two lenses, 121 and 15, which are used to focus light on the skill.

It is obvious to those skilled in the art that the lenses 121 and 122, and eventually 15, of the interface optics 12 in FIGS. 2a, b, c, d can be replaced by mirrors, in which case all the elements traversed by the beam, 9, of the apparatus are used in reflection, improving the dispersion performance of the OCT channel even further.

The optical splitter, 8 in FIG. 2 can be implemented in different ways as shown in later figures and can include, for example, a large band beam-splitter, as a variably deposited beam-splitter or as a beam-splitter with controlled reflectivity, 81, or as a band-pass (when the apparatus according to the invention uses a R-OCT/T-C configuration) or notch optical filter (when the apparatus uses a T-OCT/R-C configuration), 82, or as a spectrally selective element such as a cold mirror, or a hot mirror, or an edge filter, 83, or a combination of the above, 84, or a polarisation sensitive beam-splitter, 85, or a holed rotating disk, 86. This will become more evident in the explanation of the different embodiments which follows.

It should be obvious for those skilled in the art that although the embodiments in FIGS. 2a–d show optical mapping apparatuses according to the invention in regime R-OCT/T-C, that configurations in regime T-OCT/R-C are equally feasible.

Figure 3:
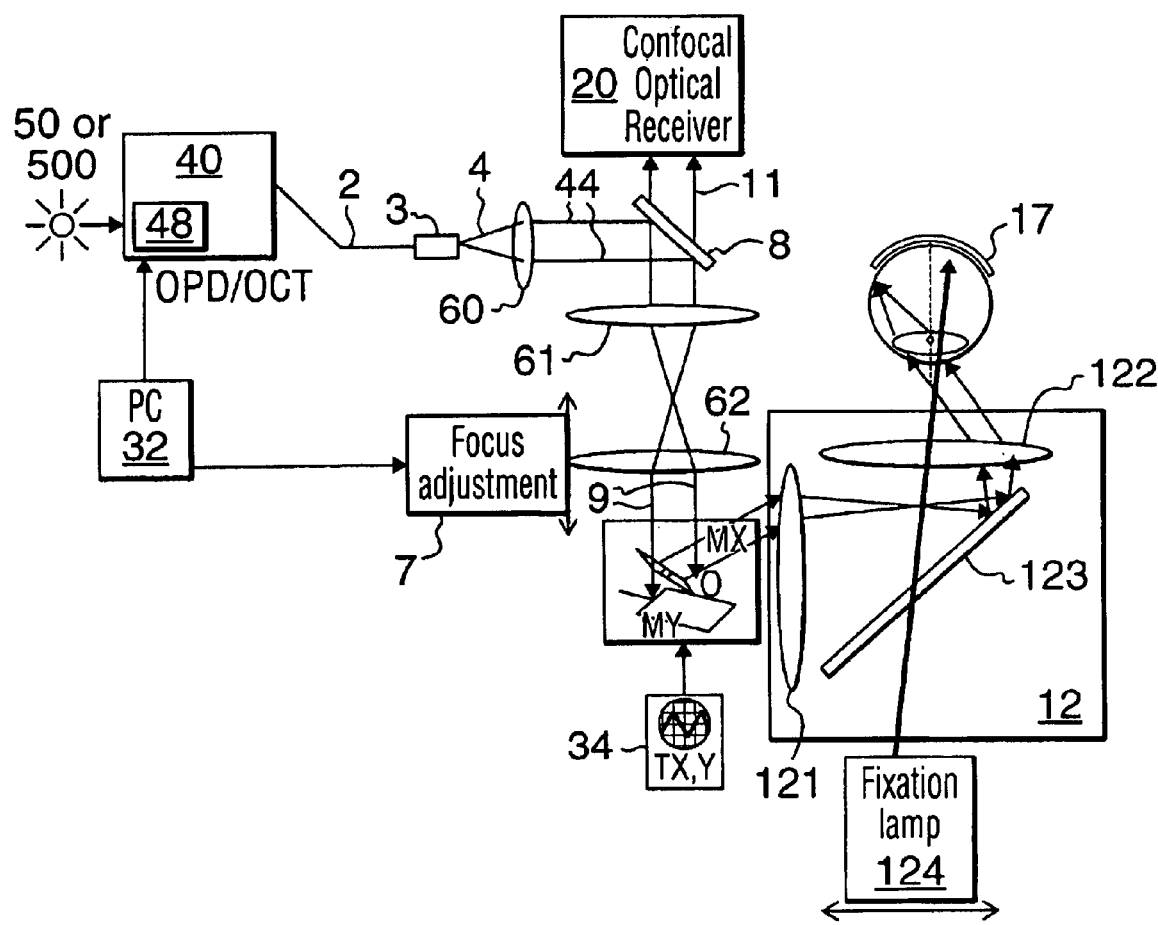
FIG. 3 shows, in diagrammatic form, another embodiment of the main elements of the focusing adjustment to maintain both receiver apertures (OCT and confocal) in focus wherein both beams towards and from the optical-splitter, which are shared by the confocal and the OCT channel, are collimated.

FIG. 3 describes another system of focusing according to the present invention to insure that the confocal and the OCT channel focus at the same depth in the object. FIG. 3 refers to a particular case where the beam 4 out of the OCT, fiber aperture or bulk spatial filter is collimated by the lens 6 and the beam towards the confocal optical receiver is also collimated. A beam expander is used after the optical-splitter 8, which beam expander is implemented with two lenses, 61 and 62, where the one of the lenses, 62, is movable in relation to the other lens axially, by means of an adjustable element, 7. In this case, the distance from the optical-splitter 8 to the fibre tip, 3, and to the confocal optical receiver, 20, is not critical any more, as was the case in FIGS. 2a–d, as the beam transmitted, 44 and the beam from the confocal optical receiver, 11 are collimated. In this case, the OCT and the confocal channel have supplementary independent focusing adjustments. It is also possible for beams 44 and 11 to be slightly uncollimated, in which case the first element of the focus adjustment, lens 61 in FIG. 3 can be used for compensation. It is obvious that when the interface optics, 12, uses only one lens, 121, as shown in FIGS. 2c and 2d, the beam after the lens 62 converges in the front of the lens 121, at its focal length, as explained in connection to FIGS. 2c and 2d. It is also obvious that either of the lenses 61, or 62 can be moved axially by the focus adjustment block, 7.

It should be obvious for those skilled in the art that the regime R-OCT/T-C implemented in FIG. 3 is for illustration only and a similar focusing configuration equally works with an embodiment in configuration T-OCT/R-C.

To avoid noise in the OCT, the fiber end reflections have to be minimised, as described in the paper "Unbalanced versus balanced operation in an OCT system", published in the Appl. Opt., (2000), Vol. 39, No. 1, pp. 173–182 by A. Gh.

Podoleanu, therefore the fiber end in FIGS. 2 and 3 are cleaved at an angle and eventually anti-reflection coated. The support of the fiber end 3 allows a counter tilt to compensate for the surface end orientation. For instance, the fiber end 3 could be the inclined facet of an adaptor FC/APC or an ST/APC, which adaptors are known by those skilled in art of fibre optics, or the fiber end could be a bare fibre cleaved at an angle.

It should be obvious for those skilled in the art that lens 60 in FIGS. 2a–d and lenses 61 and 62 in FIG. 3 could be groups of lenses, convergent and, or divergent, as well as different combination of mirrors, or combination of mirrors and lenses or groups of lenses or mirrors which could be used to accomplish the same objective.

FIG. 4 shows different possible implementations of the confocal optical receiver. FIGS. 4a, 4b, 4d and 4e show set-ups compatible with FIGS. 2a–d while FIGS. 4c and 4f show set-ups compatible with the configuration in FIG. 3. The element 206 stands for a photodetector, which could be an avalanche photodiode or a photomultiplier, either directly illuminated or placed at the end of a fiber pigtail, as described in the U.S. Pat. No. 5,975,697, in which case the aperture of the confocal optical receiver is the fiber input and the pinhole 202 may be eliminated, or the depth of focus of the confocal optical receiver is the result of the combined effect of a pinhole 202 in front of the fiber and of the fiber aperture. The pinhole 202 could be fixed or adjustable to allow the control of the depth resolution in the confocal channel. No lens is used in FIG. 4a and the beam is focused on a pinhole tightly placed above photodetector, 206. In other embodiments, one or two lenses 201 and 203 are used according to prior art disclosed in confocal microscopy. The lens 201 focuses the light into the pinhole 202, and a second lens, 203, focuses or spreads the light onto the photodetector surface, 206, of the confocal optical receiver, 20. Spectral selection is required in some embodiments, in which case a pass band filter, 204 and a notch filter, 205 are used. It is obvious for those skilled in the art that the order of the elements 204 and 205, whether before or after the lenses, or whether before or after the pinhole 202 is not essential.

All surfaces of different elements in FIG. 4, including the photodetector facet, the fiber input surface and the other spectral selective elements are tilted to avoid reflections back into the OCT system, and the lenses are anti-reflective coated for the wavelength of the source used in the OCT channel.

Figure 5A:
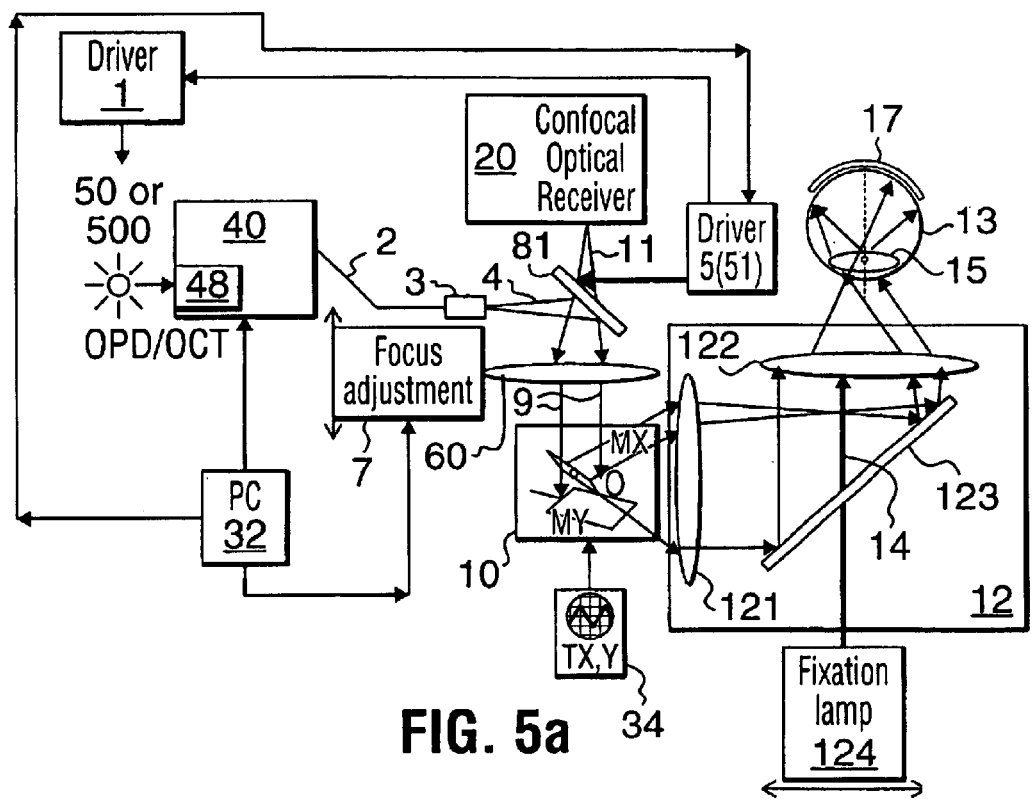
FIG. 5a shows, in diagrammatic form, an embodiment of the optical mapping apparatus with adjustable depth resolution according to the invention wherein the percentages of light returned from the tissue towards the two channels (OCT and confocal) can be adjusted.

FIG. 5a shows another implementation, wherein in order to balance the amount of light diverted to the confocal optical receiver, 20, the optical-splitter, 81, may be different from the simple beam-splitter, 8, described in U.S. Pat. No. 5,975,697. The beam-splitter, 81, may have a gradual or a step deposition with height, which allows the reflectivity, η and transmission 1-η to vary with height, or with a lateral coordinate, allowing the returned irradiance to the confocal optical receiver, 20, to be varied from very low to very high values, as an example, from η=1% to 98% of $P_{object}$ O, where $P_{object}$ is the power delivered to the object and O is the reflectivity of the object. A driver 5, shifts the beam-splitter 81 vertically, or laterally, generally along the gradient of the deposition axis to adjust the percentage of light reflected and transmitted. When doing so, the driver 5 may also act on the driver 1, of the optical source, 50 or 500, to increase the power when the optical-splitter is positioned for low values of reflectivity, in order to maintain the same power to the object, where a lossless interface optics was considered for simplicity. For instance, when η=0.5, the OCT and the confocal channel receive each half of the power returned. In comparison with the case when η=1 and no light is returned to the confocal channel, the power at the output, 3, is double to the case η=0.5 if the same power on the target was maintained. For those skilled in the art, it is evident that the mount of the beam-splitter 81 can be equipped with a micro-motor when the optical-splitter 81 is gradually deposited or can have two or more stable positions when the optical-splitter has step depositions. The driver 5 can be implemented by means known in the art, such as an electromechanical circuit to control a micro-motor for fine displacement along the gradient of the deposition axis, or a manual knob on the front panel of the instrument which is mechanically tied up to the mount of the beam-splitter.

As another alternative, the optical-splitter 81 may be a splitter with transmission and reflectivity controllable by an external field, for instance such as an electro-optic or a magneto-optic or a liquid crystal plate, which under the control of an electric field, or of a magnetic field or both, can have the reflectivity and transmission altered according to computer control, 32. In this case, the driver 51 applies suitable electric fields or magnetic fields or both to the beam-splitter element 81, by means known in the art.

It should also be evident for those skilled in the art that the same configuration of control, using the same optical-splitter, 81, with graded deposition or under external field control, and driver 5 or driver 51, respectively, can be applied to the version of focusing diagram in FIG. 3, in which case the confocal optical receiver as shown in FIG. 4c should be used instead of configurations 4a and 4b.

It should also be obvious for those skilled in the art that the regime R-OCT/T-C implemented in FIG. 5a is for illustration only and a similar configuration equally works with an embodiment in configuration T-OCT/R-C.

Figure 5B:
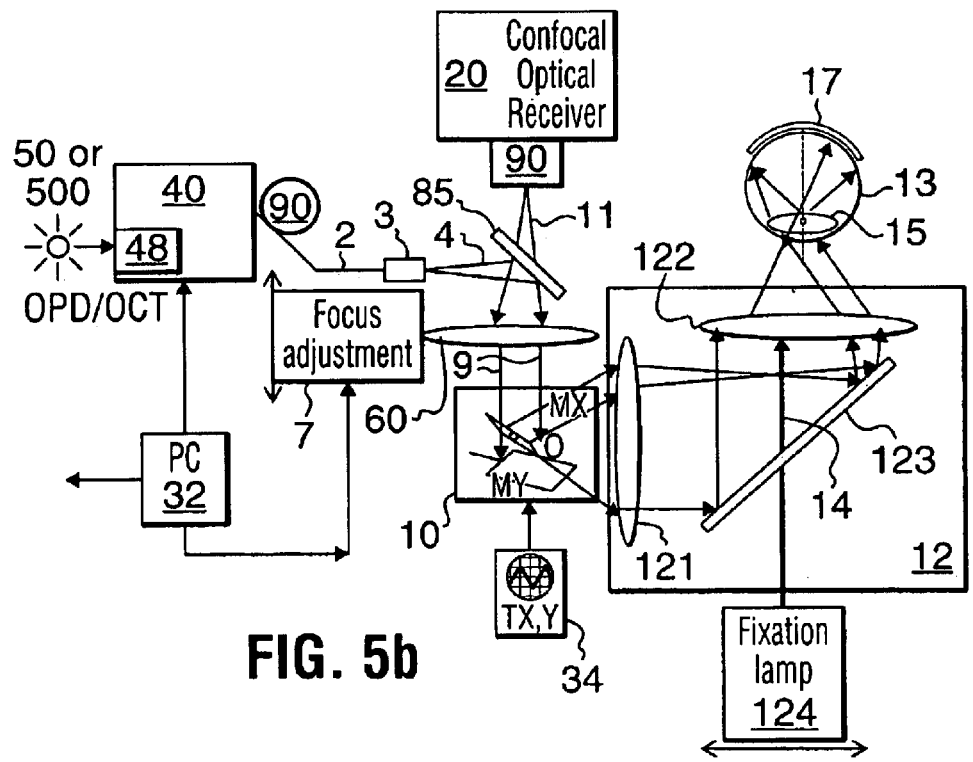
FIG. 5b shows, in diagrammatic form, an embodiment of the optical mapping apparatus with adjustable depth resolution according to the invention wherein the OCT and the confocal channel use polarised light and the optical-splitter is a polarisation sensitive beam-splitter.

FIG. 5b shows, in diagrammatic form, an embodiment of the optical mapping apparatus with adjustable depth resolution according to the invention where the OCT and confocal channel use polarised light and the optical-splitter 85 is a polarisation sensitive beam-splitter. The light out of the OCT system is polarised by the polariser 90, which could be a fiber polariser or a dycroic sheet or other bulk polariser, in a direction that all light passes through the polarisation sensitive optical-splitter 85. The light returned from the object has different polarisation orientations and some of the light will go back to the OCT and the light with rectangular direction to that of the OCT output will go to the confocal optical receiver 20, which may also be equipped with a linear polariser with axis orientation orthogonal to the polarisation direction of the OCT output, for better polarisation selection.

Figure 6A:
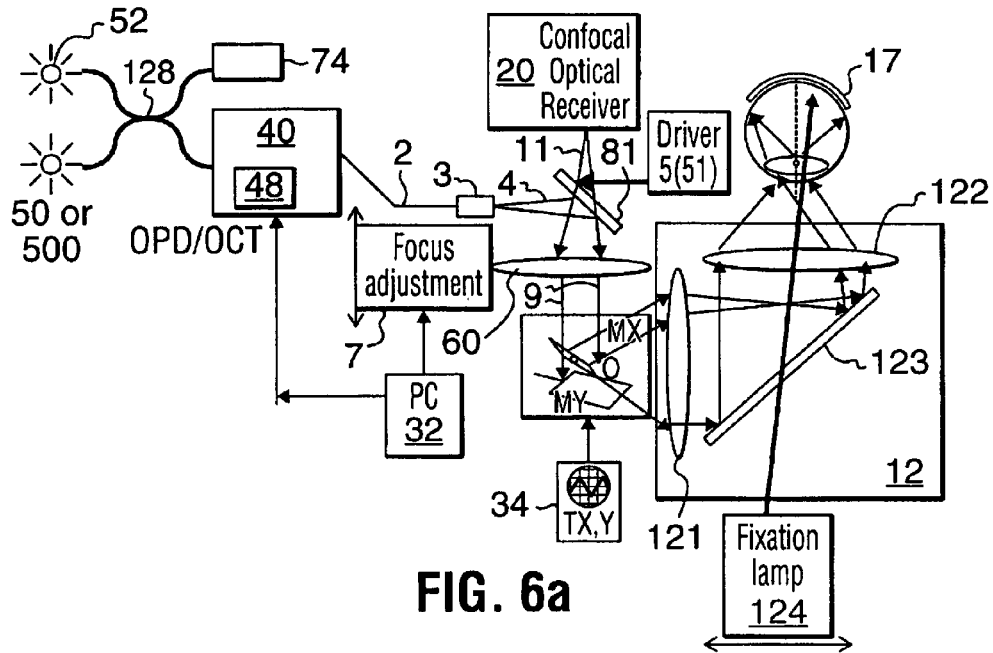
FIG. 6a shows, in diagrammatic form, an embodiment of the optical mapping apparatus with adjustable depth resolution according to the invention, wherein different wavelength sources are used for the OCT channel and for the confocal channel in order to make maximum use of the spectral sensitivity of the photodetector in the confocal channel when a fixed optical-splitter is used.
Figure 6B:
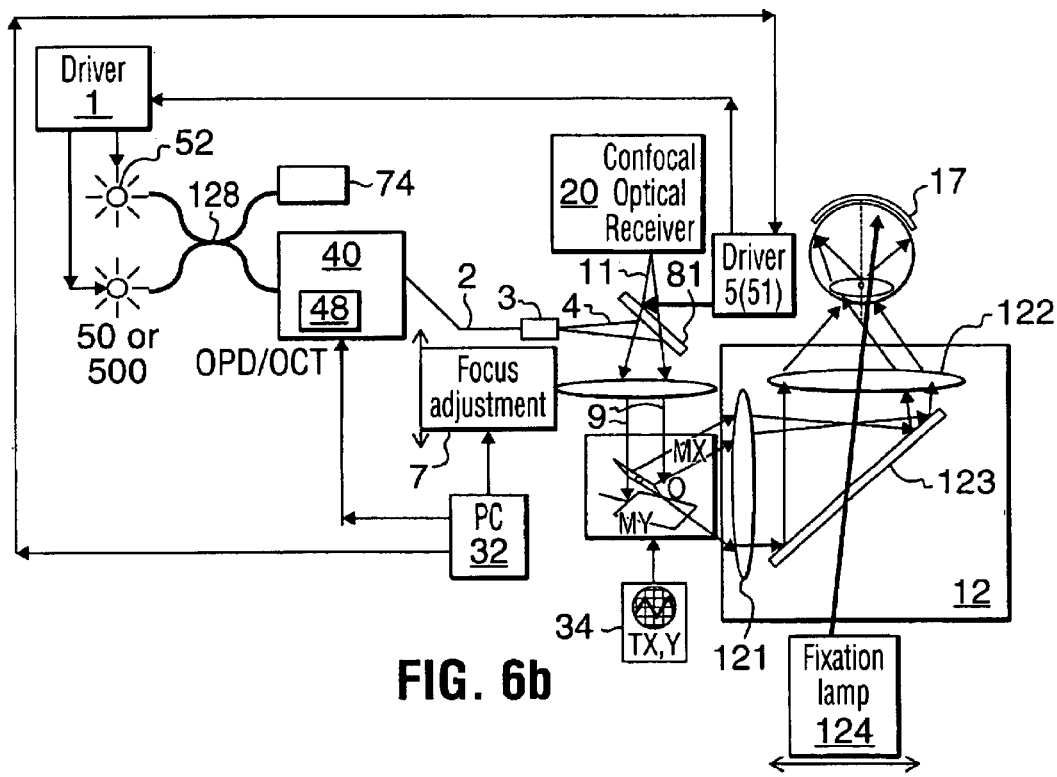
FIG. 6b shows a variation of the embodiment in FIG. 6a, wherein an adjustable ratio optical-splitter is used.

Another alternative for enhancing the confocal channel signal is illustrated in FIGS. 6a and 6b for such cases wherein the OCT channel works in reflection on wavelengths larger than 1200 nm, at which the photodetector in the confocal channel has a very low sensitivity. Silicon photodetectors and photomultipliers have large gains in near infrared and visible which rolls off for wavelengths larger than 900 nm. Therefore, two sources are used in the configurations in FIGS. 6a and 6b, (i) a low coherence source, 50 or a low coherence source with adjustable coherence length, 500 on the infrared wavelength used in the OCT channel and (ii) an optical source of low or high coherence, 52, working in near infrared wavelengths smaller than 900 nm or in visible wavelengths. The power of the two sources will obviously be adjusted up to the level allowed by the safety of the tissue object, 17. The optical-splitter could be either large bandwidth, 8, as shown in FIG. 6a or one with gradual deposition, or an electro-optic, or magneto-optic or liquid crystal, 81, as shown in FIG. 6b. The reflectivity could be adjusted similarly to the case discussed in connection to FIG. 5 above, and at the same time, the power on the two sources could be weighted relatively to make sure that the sum does not exceed the safety level on the object, adjustment and control being implemented via driver 5 as above, and where the driver 1 now controls both sources, 50 (500) and 52. Any configuration of large band confocal optical receiver shown in FIGS. 4a, 4b can be used in FIG. 6a. Also, the confocal optical receiver can be tuned to the wavelength of the optical source 52, in which case any configuration of confocal optical receiver as shown in FIGS. 4d and 4e can be used. If the focusing configuration shown in FIG. 3 is implemented, either the large band configuration of confocal optical receivers shown in FIG. 4c, or the configuration of tuned confocal optical receivers, as in FIG. 4f will be preferably used instead.

The two sources shown in FIGS. 6a and 6b, and later in FIGS. 7a–d, are superposed by the element, 128, which could be a directional coupler or a bulk beam-splitter, or a hot or a cold filter, or a wavelength demultiplexing coupler (WDM) coupler with high or large transmission (such as greater than 70%, more preferably greater than 80%, and most preferably, greater than 90%), for each of the two wavelengths of the two sources. When implemented in fibre, 74 signifies index matching gel for minimised reflection. When implemented in bulk, 74 signifies an opaque tilted screen.

It should be obvious for those skilled in the art that the regime R-OCT/T-C implemented in FIGS. 6a,b is for illustration only and similar configurations equally work with embodiments in configuration T-OCT/R-C.

Figure 7A:
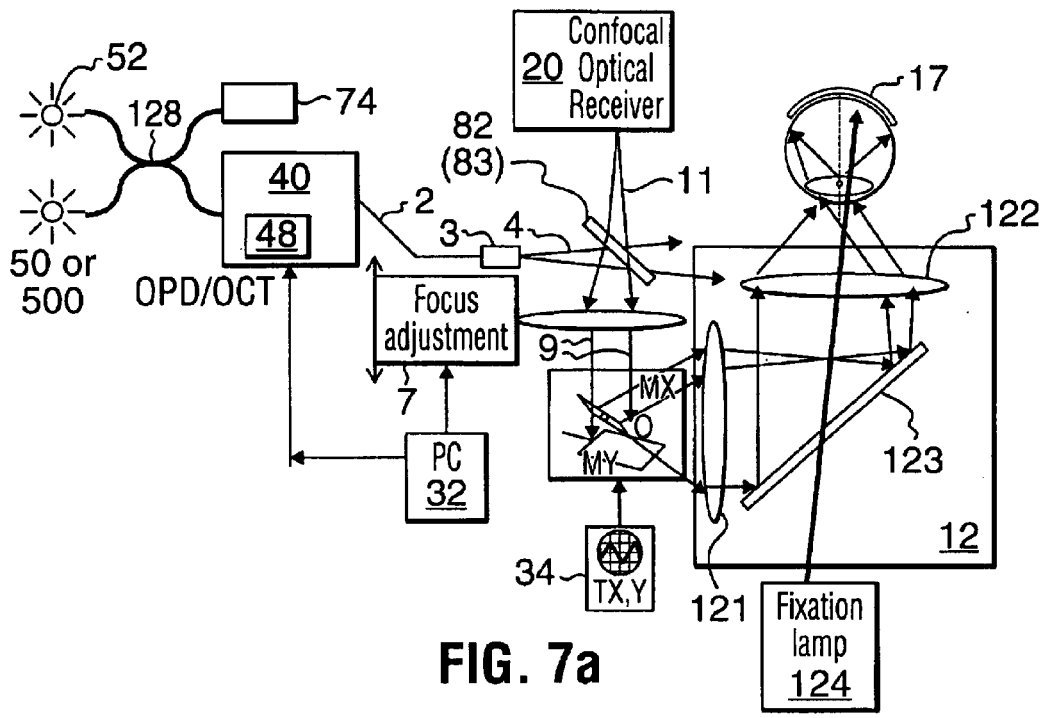
FIG. 7a shows, in diagrammatic form, an embodiment of the optical mapping apparatus according to the invention in configuration R-OCT/T-C where the optical-splitter shared by the OCT channel and the confocal channel is a spectrally selective element such as a band-pass filter, a cold mirror, a hot mirror, or an edge filter, where the OCT and the confocal channel operate on different wavelengths.

The embodiment in FIG. 7a allows confocal and OCT imaging at different wavelengths. Further utility of the confocal channel and for the dual channel optical mapping apparatus as a whole can be obtained if the two wavelengths are different. Using different wavelengths when imaging the tissue, increased contrast can be achieved. This may also allow fluorescence imaging and autofluorescence imaging in the confocal channel with simultaneous OCT imaging. Subsequent high resolution 3D visualisation can be generated using a stack of en-face OCT images of those parts of the tissue which exhibit abnormal autofluorescence or fluorescence or Raman emission. In this case, the fluorescence or Raman emission indicates the parts of the tissue to be subsequently imaged with high resolution and in 3D using the OCT channel. The embodiment in FIG. 7a exhibits low losses in either channel, wherein the optical-splitter is a band-pass filter, 82, on the wavelength of the source, 52, when the two wavelengths, of the two sources, 50 (500) and 52 are sufficiently far apart. Such band-pass filters are known, with transmission of more than 50% at the central wavelength and with a band-pass of 5–10 nm. If the wavelength of the source 52 coincides with the central wavelength of the filter, then the filter operates for this wavelength as a 50/50 beam-splitter. If the wavelength of the OCT source, 50 or 500 is sufficiently outside the pass-band of the filter, then reflectivity in excess of 80% can be obtained, which is useful to transfer efficiently forward and back the OCT signal. For instance, the mapping apparatus can operate with the OCT channel source 50 (or 500) in infrared (780–950 nm) and the confocal channel source 52 in visible for the eye or with the source 50 (500) in infrared (1200–1300 nm) and the confocal source 52 in infrared or visible (500–800 nm) for skin. Equally important, such an embodiment can serve the observation of auto-fluorescence in the eye. To this goal, the filter 82 can be tuned on the auto-fluorescence wavelength and the excitation wavelength, of the source 52, is reflected by the pass-band filter 82 as it is outside its band. Source 52 may emit in blue with the filter 82 tuned on yellow and the wavelength of the source 50 (or 500) in infrared.

If the configuration T-OCT/R-C is used, the optical splitter is a notch filter 82 tuned on the wavelength of the source, 59, or the auto-fluorescence or Raman wavelength. If the wavelength of the OCT source, 50 or 500 is sufficiently outside the notch-band of the filter, then transmission in excess of 80% can be obtained.

Equally, the optical-splitter, 83, could be a hot or a cold mirror, or an edge filter. In this case, the losses for each channel, confocal, beam 11 and OCT, beam 4, are minimal. Such cold and hot filters exist with more than 95% transmission and less than 5% reflectivity in one band and with less than 5% transmission and more than 95% reflectivity in the other band. In this way, both channels use more than 95% of their beam returned from the target. In FIG. 7a, two optical sources are employed, one source on the wavelength used by the OCT channel, a low coherence source, 50 or a low coherence source with adjustable coherence length, 500 and a second source on the wavelength used by the confocal channel, 52, which can be coherent or of low coherence, tuneable or not, preferably a laser, in such a way that the wavelength of each source is either side of the cut-off or edge frequency of the spectral element, 83. The source 52 should be strong enough to compensate for the loss in the element 83, which has a high transmission for the wavelength used by the confocal channel and consequently a low reflectivity for the same wavelength.

When used for skin, the hot mirror 81 may have a cut-off of 1000 nm, with the source 52 on 800 nm and the source 50, or 500 at 1200–1300 nm. The same combination of wavelengths is useful for imaging the cornea, in which case a fixation lamp 124 is also needed. The interface optics splitter, 123, may be a hot mirror with edge at around 700 nm. It may also be possible that the optical-splitter, 83 is a cold mirror, when the OCT works in the blue band and the confocal optical receiver in red or infrared. Any of the confocal optical receiver configurations in FIGS. 4a,b can be used or if the radiation on the wavelength of the OCT channel needs to be further attenuated, the configurations in FIGS. 4d, 4e can be used. If the configuration of focusing in FIG. 3 is implemented, then the confocal optical receiver configurations in FIG. 4c or 4f are to be preferably used instead respectively.

The possible regimes of operation and the possible choices for the confocal optical receiver are summarised in the inset table in FIG. 7a.

Figure 7B:
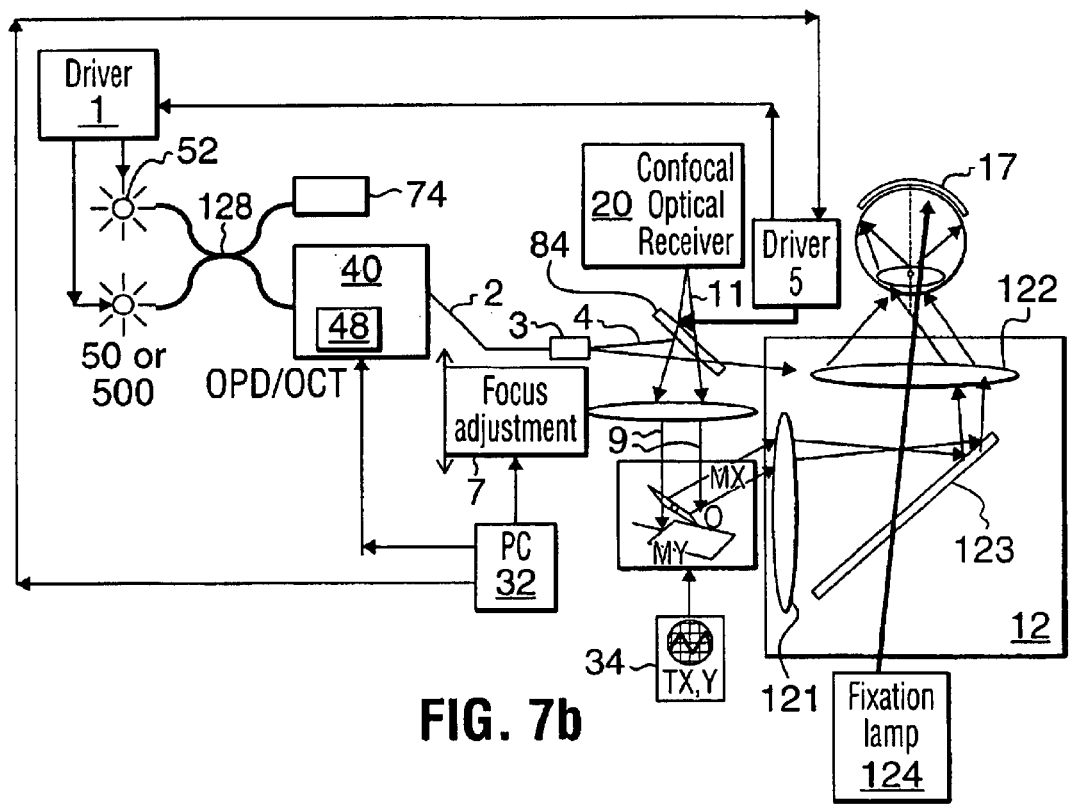
FIG. 7b shows, in diagrammatic form, an embodiment of the optical mapping apparatus according to the invention in configuration R-OCT/T-C where the optical-splitter shared by the OCT channel and the confocal channel is a two part beam-splitter, with one part being a plate beam-splitter and the other part being a spectrally selective element such as a cold mirror, a hot mirror, or an edge filter, where depending on the optical-splitter position, different regimes of operation are possible, such as, for example, where the OCT and the confocal channel operate on the same or on different wavelengths, for auto-fluorescence or fluorescence studies.

Alternatively, optical-splitter, 84, in FIG. 7b is made from different parts assembled along a reflectivity variation axis: (i) a conventional large band beam-splitter continuing with (ii) a spectrally selective element, such as a band-pass or a notch filter 82 or edge filter, cold mirror or hot mirror 83. The driver 5 suitably shifts the optical-splitter 84 along the said reflectivity variation axis to introduce one of the two parts into the beam, similar to the case explained above in connection to FIG. 5. In this case, the optical mapping apparatus can operate in different regimes, as explained in the inset table in FIG. 7b. The apparatus according to the invention can provide images with two different depth resolutions, fine in the OCT and coarse in the confocal, on (i) the same wavelength, of the low coherence source 50 or adjustable coherence length, 500 when the source 52 is switched off; (ii) on different wavelengths, similar to the embodiment in FIG. 6a, wherein in the regimes (i) and (ii), the optical-splitter is in that position, wherein the large band optical-splitter 8 intersects the beam 4, or (iii) on wavelengths similar to the embodiment in FIG. 7a, when the optical-splitter is in that position, where the spectral beamsplitter, 82, intersects the beam 4. Such a beam-splitter can be devised by means known in the art, for instance using for half of the surface a metal large bandwidth deposition and on the other half, a dielectric, multiple layer, optically selective deposition. Normally, the confocal optical receiver configuration in FIGS. 4a and 4b should be used, or that in FIG. 4c if the focusing configuration in FIG. 3 was used.

Figure 7C:
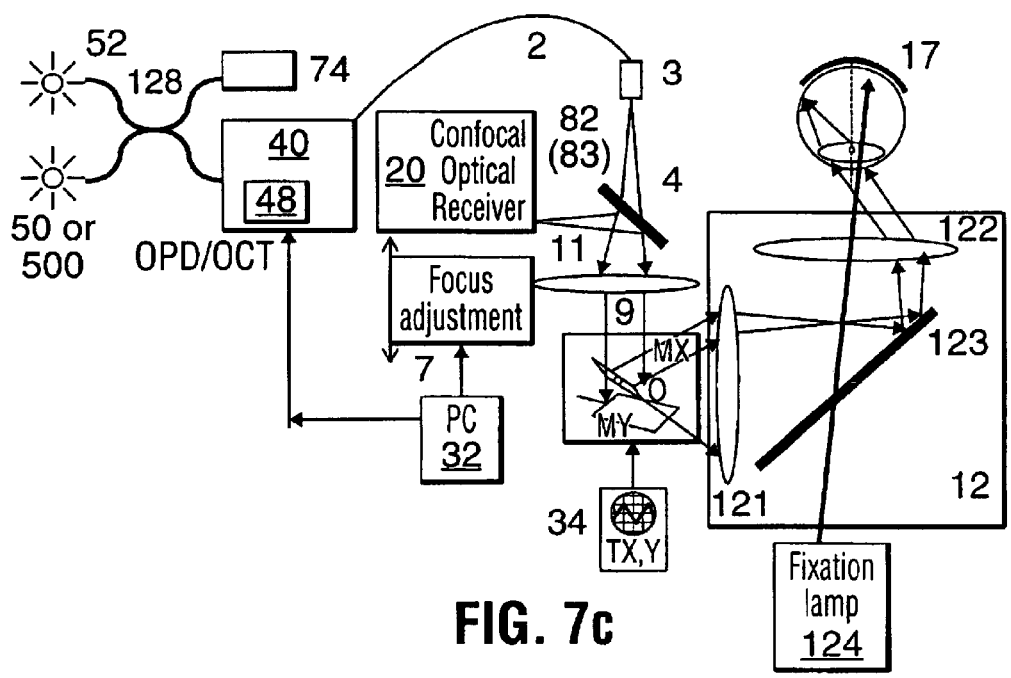
FIG. 7c shows, in diagrammatic form, an embodiment of the optical mapping apparatus with adjustable depth resolution according to the invention, similar to that disclosed in FIG. 7a but in configuration T-OCT/R-C, where the optical-splitter shared by the OCT and the confocal channel is a spectrally selective element such as a notch filter, a cold mirror, a hot mirror, or an edge filter.

FIG. 7c shows, in diagrammatic form, an embodiment of the optical mapping apparatus with adjustable depth resolution according to the invention, similar to that disclosed in FIG. 7a but in a configuration T-OCT/R-C, where the optical-splitter shared by the OCT and the confocal channel is a spectrally selective element such as a notch filter, a cold mirror, a hot mirror, or an edge filter, and where the OCT and the confocal channel operate on different wavelengths.

Figure 7D:
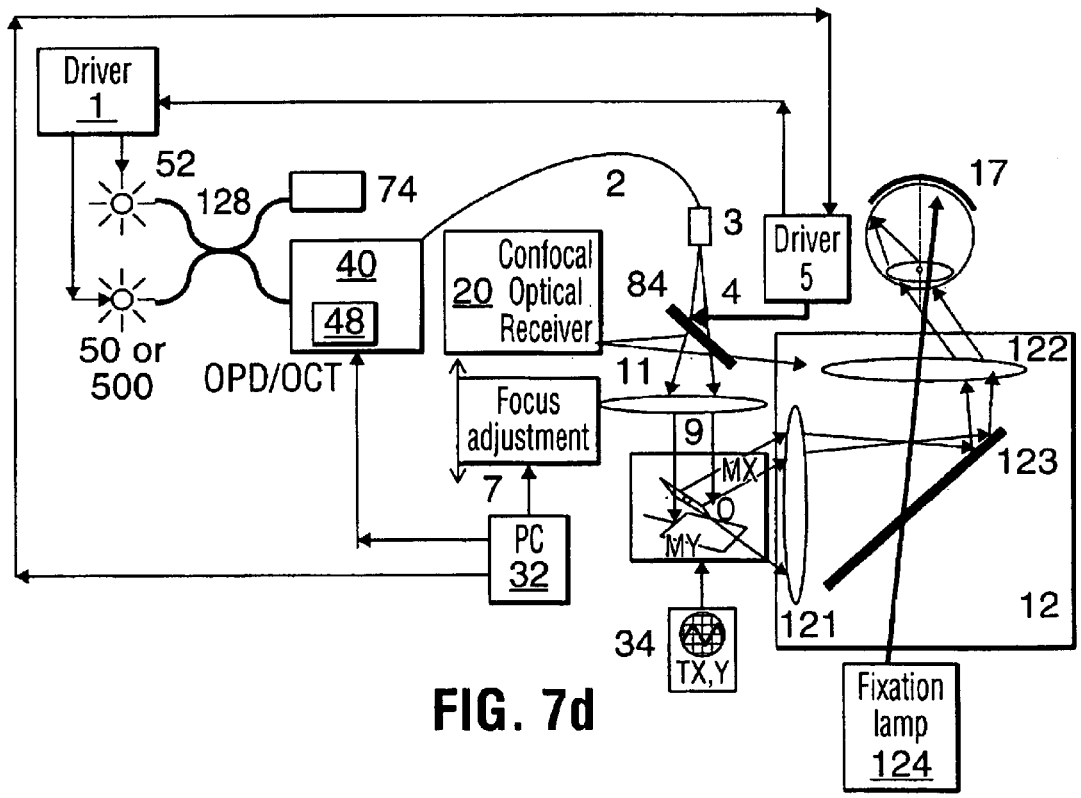
FIG. 7d shows, in diagrammatic form, an embodiment of the optical mapping apparatus according to the invention, similar to that disclosed in FIG. 7b but in configuration T-OCT/R-C, where the optical-splitter shared by the OCT and the confocal channel is a spectrally selective element such as a notch filter, a cold mirror, a hot mirror, or an edge filter.

FIG. 7d shows, in diagrammatic form, an embodiment of the optical mapping apparatus with adjustable depth resolution according to the invention, similar to that disclosed in FIG. 7b but in configuration T-OCT/R-C, where the optical-splitter shared by the OCT and the confocal channel is a spectrally selective element such as a notch filter, a cold mirror, a hot mirror, or an edge filter.

All the elements following the beam-splitter 8 in FIG. 6a, following the beam-splitter 81 in FIG. 6b, following the beam-splitter 82 or 83 in FIGS. 7a and 7c and 84 in FIGS. 7b and 7d need to be large bandwidth, compatible with the two bands used, the output beam 9 containing the wavelengths of both optical sources, 50 (500) and 52.

Figure 8A:
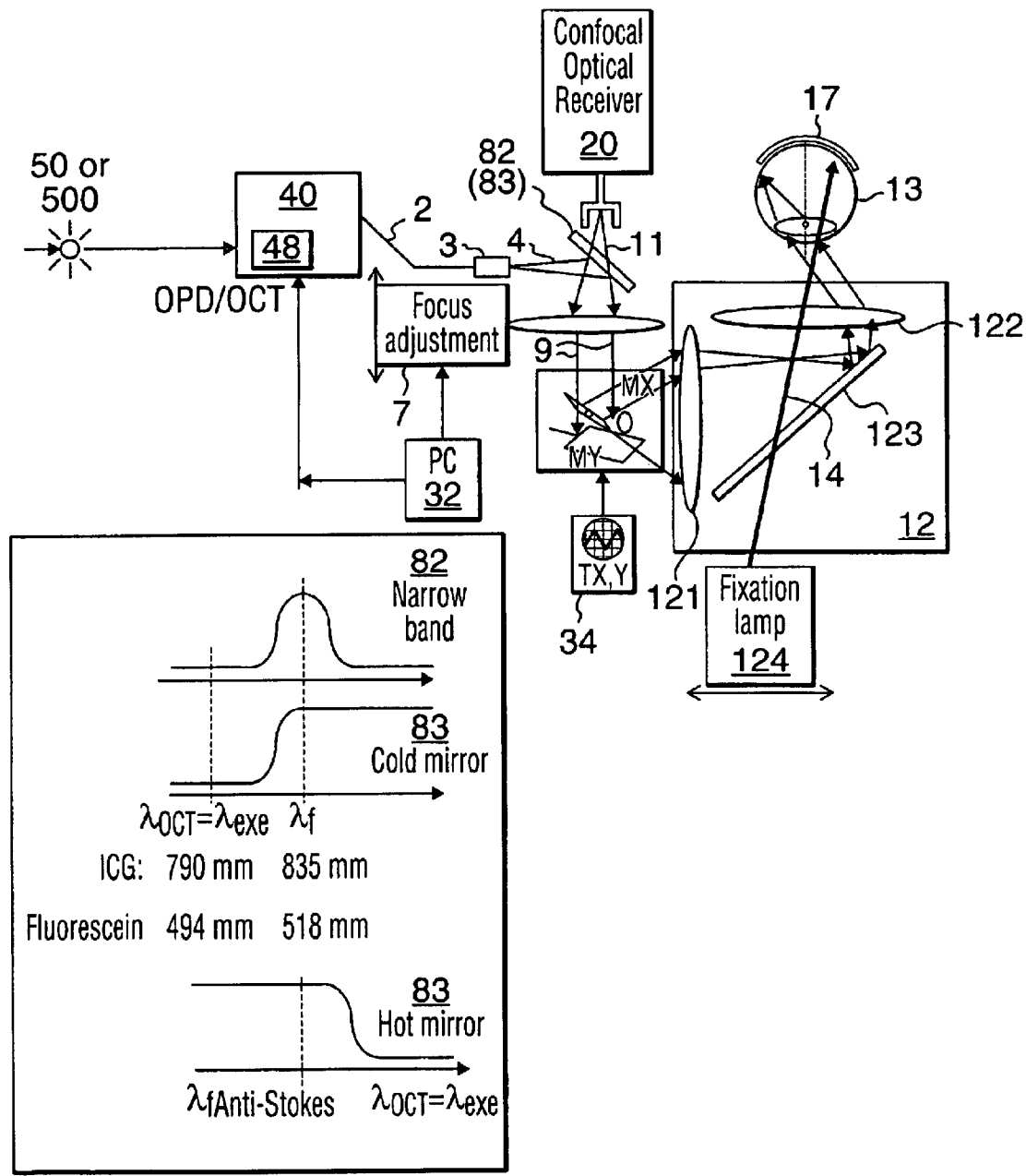
FIG. 8a shows, in diagrammatic form, an embodiment of the optical mapping apparatus with adjustable depth resolution according to the invention in configuration R-OCT/T-C where the optical-splitter shared by the OCT and the confocal channel is a spectrally selective element, such as a band-pass filter, a cold mirror, a hot mirror, or an edge filter, and wherein the confocal channel operates on the wavelength band of the fluorescence or Raman radiation generated by the object under the excitation of the optical source.

FIG. 8a shows in diagrammatic form another embodiment of the present invention, in configuration R-OCT/T-C useful for studies of the fluorescence or Ramana radiation emitted by the object under the excitation of the low coherence source used in the OCT channel. The OCT channel works on the wavelength of the low coherence source, 50, or of the low coherence source with adjustable coherence length, 500 while the confocal optical receiver 20 works on the fluorescence or Raman wavelength emitted by the target, which in FIG. 8a is the retina, 17, of an eye. Preferably, a spectral optical-splitter, is used, a hot, or a cold mirror, or an edge filter 83 or a band-pass filter 82 to separate the two bands, OCT and fluorescence. To eliminate the light of the excitation source, 50 or 500, the confocal optical receiver, 20, uses notch filter 205 and band-pass filter, 204 (shown in FIGS. 4d,e,f) on the fluorescence or Raman wavelength. For instance, when using ICG angiography in the eye, the OCT wavelength should be 790 nm, and the spectral beam-splitter 83 is a cold mirror with an edge at 810 nm, or a narrow band filter tuned on 835 nm and the confocal optical receiver may be equipped with a notch filter 205 on the excitation wavelength 790 nm and with a pass-band filter, 204, on 835 nm. When using fluorescein angiography, the OCT wavelength could be 494 nm and the spectral beam-splitter 83 is a cold mirror with an edge on 506 nm, or a narrow band filter tuned on 518 nm, and the confocal optical receiver equipped with a notch filter 205 on the excitation, 494 nm and with a pass-band filter, 205 on 518 nm. The inset in FIG. 8a shows the relative position of the wavelengths in the system for different optical splitters. Top and middle figures in the inset, are for the ICG and fluorescein implemented using either a cold mirror, 83 or a narrow band filter 82, to process the fluorescence wavelength, $\lambda_f$ and the excitation wavelength, $\lambda_{exc}$=OCT wavelength, $\lambda_{OCT}$. The example at the bottom is for the anti-Stokes radiation, in which case the optical splitter is a hot mirror, 83. It is obvious that a band-pass filter, 82, could be used to select the anti-Stokes radiation as well.

Figure 8B:
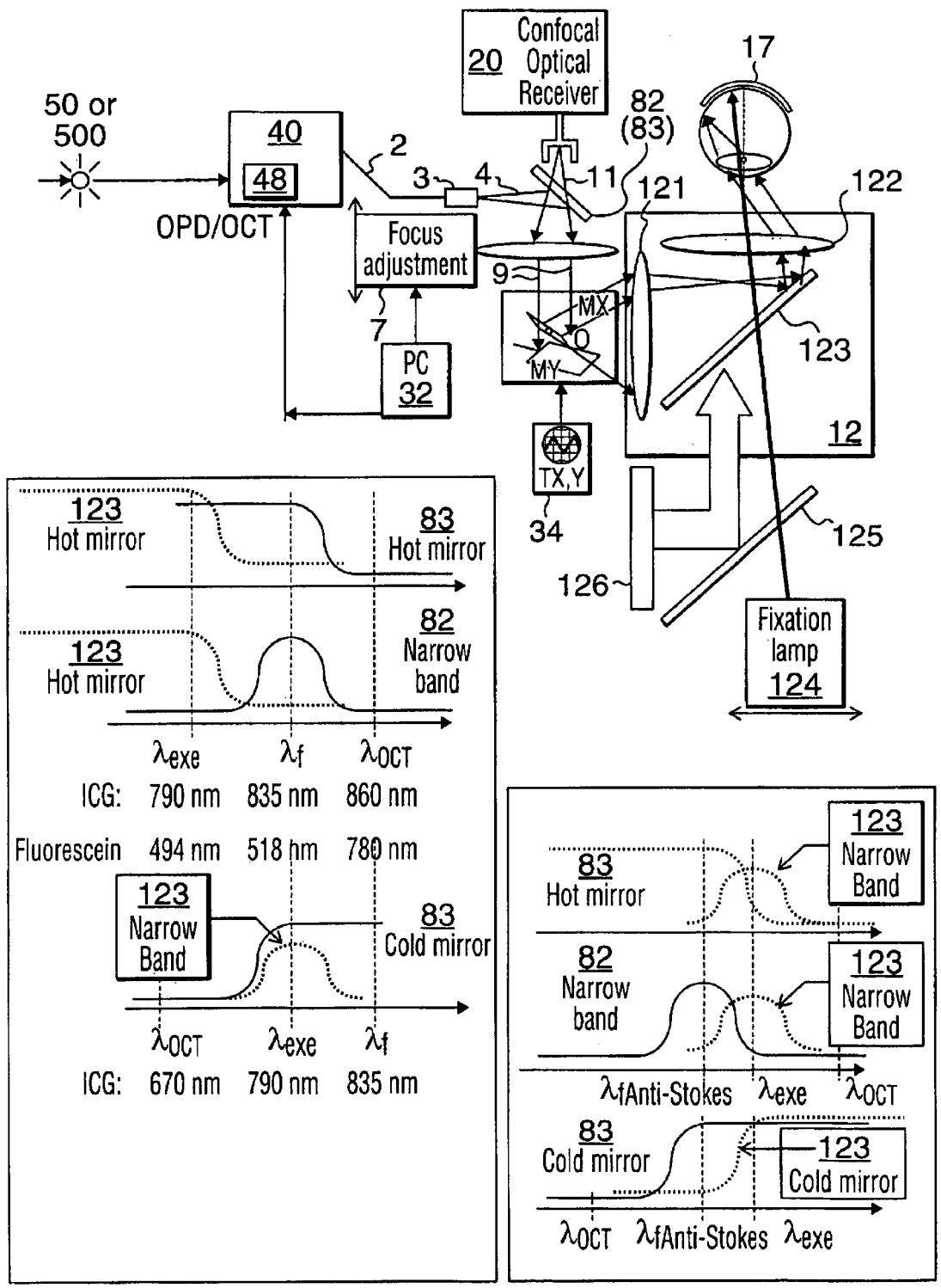
FIG. 8b shows, in diagrammatic form, an embodiment of the optical mapping apparatus with adjustable depth resolution according to the invention, in configuration R-OCT/T-C where the optical-splitter shared by the OCT and the confocal channel is a spectrally selective element such as a band-pass filter, a cold mirror, a hot mirror, or an edge filter, and wherein the confocal channel operates on the wavelength band required for fluorescence or Raman studies of the radiation emanated by the object under the excitation of an external optical source.

FIG. 8b shows in diagrammatic form another embodiment of the present invention in configuration R-OCT/T-C, useful for fluorescence or Raman studies, where an external excitation source, 126, illuminates the object, which in FIG. 8b is the retina, 17, of an eye 13, via beamsplitter 125. The OCT channel works in reflection from the optical splitter on the wavelength of the low coherence source, 50, or of the low coherence source with adjustable coherence length, 500 while the confocal optical receiver 20 works in transmission from the optical splitter on the fluorescence wavelength emitted by the target. Preferably, a spectral optical-splitter, is used, which could be a hot, or a cold mirror, or an edge filter 83 or a band-pass filter 82 to separate the two bands, OCT and fluorescence. To eliminate the light of the excitation source, 126, the confocal optical receiver, 20, uses notch filter 205 and band-pass filter, 204 on the fluorescence wavelength. For instance, when using ICG angiography in the eye, the OCT wavelength should be in an interval 860–960 nm, with the source 126 on 790 nm, and the spectral beam-splitter 83 with an edge at 850 nm, and the confocal optical receiver equipped with a notch filter 205 on the excitation wavelength 790 nm and with a pass-band filter, 204, on 835 nm. When using fluorescein angiography, the OCT wavelength could be in the 800 nm band with the source 126 on 494 nm and the spectral beam-splitter 83 with an edge on 700 nm, and the confocal optical receiver equipped with a notch filter 205 on the excitation, 494 nm and with a pass-band filter, 205 on 518 nm. The left inset in FIG. 8b shows the relative position of the wavelengths in the system for different optical splitters. Top and middle figures in the inset, are for the ICG and fluorescein implemented using either a hot mirror 83 or a narrow band filter 82, to process the fluorescence wavelength, $\lambda_p$, excitation wavelength, $\lambda_{exc}$ and OCT wavelength, $\lambda_{OCT}$ which in these two cases is in infrared. The example at the bottom is for ICG again using a cold mirror, 83 in which case the OCT wavelength, $\lambda_{OCT}$ is in visible. The right inset in FIG. 8b shows the relative position of the wavelengths in the system for different optical splitters when the confocal channel processes Anti-Stokes radiation of anti-Stokes wavelength, $\lambda_{anti-Stokes}$.

Figure 8C:
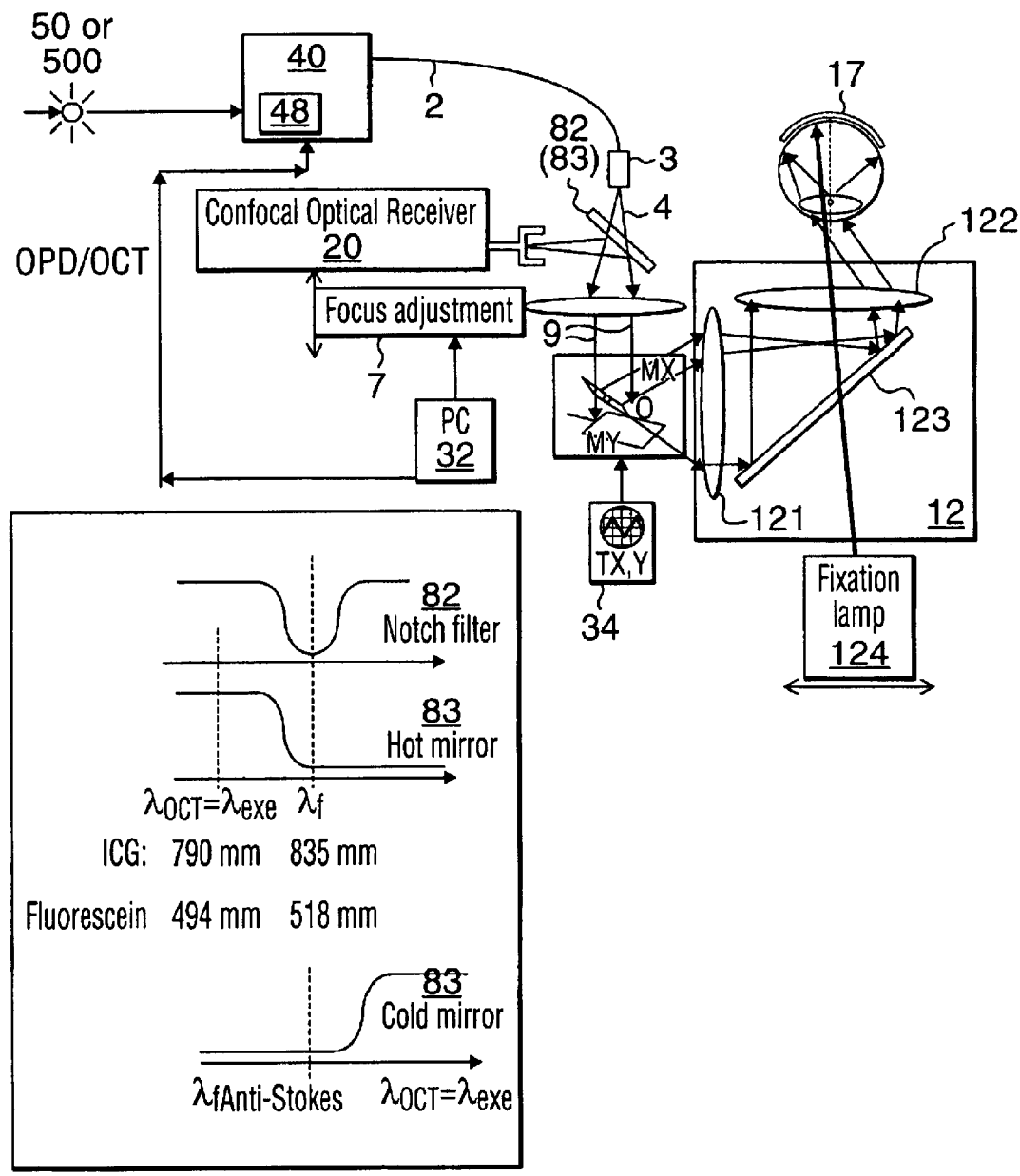
FIG. 8c is a replica of the embodiment of FIG. 8a, where the OCT channel works in transmission and the confocal channel in reflection (regime T-OCT/R-C) and wherein the optical-splitter shared by the OCT and the confocal channel is a spectrally selective element such as a notch filter, a cold mirror, a hot mirror, or an edge filter.

FIG. 8c is a replica of the embodiment of FIG. 8a, where the OCT channel works in transmission and the confocal channel in reflection, regime T-OCT/R-C, where the optical-splitter shared by the OCT and the confocal channel is a spectrally selective element such as a notch filter, a cold mirror, a hot mirror, or an edge filter. The inset in FIG. 8c shows the relative position of the wavelengths in the system for different optical splitters. Top and middle figures in the inset, are for the ICG and fluorescein implemented using either a hot mirror, 83 or a notch filter 82, to process the fluorescence wavelength, $\lambda_f$, excitation wavelength, $\lambda_{exc}$ and OCT wavelength, $\lambda_{OCT}$. The example at the bottom is for anti-Stokes radiation using a cold mirror, 83.

Figure 8D:
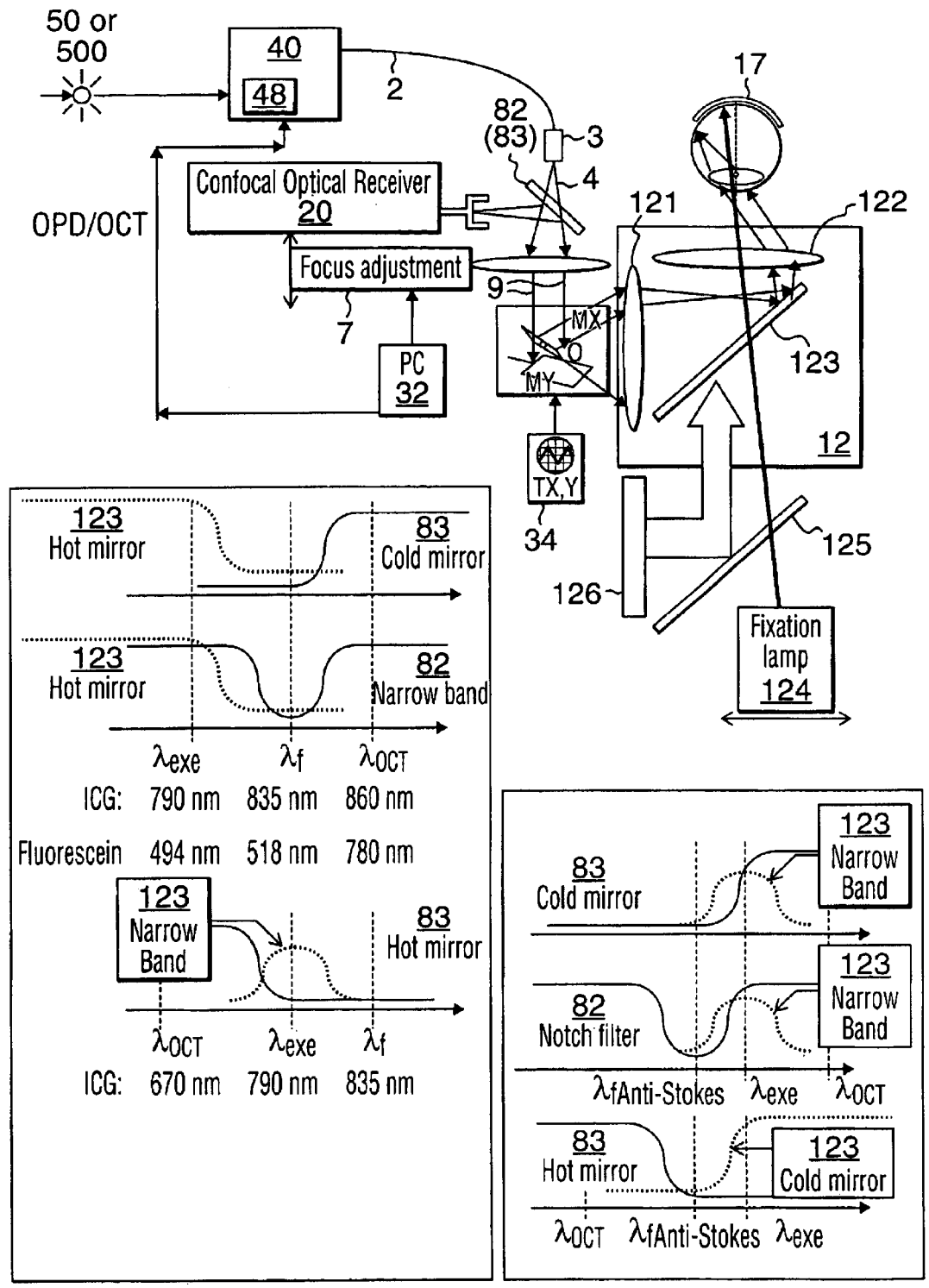
FIG. 8d is a replica of the embodiment of FIG. 8b, where the OCT channel works in transmission and the confocal channel in reflection (regime T-OCT/R-C) where the optical-splitter shared by the OCT and the confocal channel is a spectrally selective element such as a notch filter, a cold mirror, a hot mirror, or an edge filter.

FIG. 8d is a replica of the embodiment of FIG. 8b, where the OCT channel works in transmission and the confocal channel in reflection, regime T-OCT/R-C, where the optical-splitter shared by the OCT and the confocal channel is a spectrally selective element such as a notch filter, a cold mirror, a hot mirror, or an edge filter. The left inset in FIG. 8d shows the relative position of the wavelengths in the system for different optical splitters. Top and middle figures in the left inset, are for the ICG and fluorescein implemented using either a cold mirror, 83 or a notch filter 82, to process the fluorescence wavelength, $\lambda_f$, excitation wavelength, $\lambda_{exc}$ and OCT wavelength, $\lambda_{OCT}$ which in these two cases is in infrared. The example at the bottom is for ICG again using a hot mirror, 83 in which case the OCT wavelength, $\lambda_{OCT}$ is in visible. The right inset in FIG. 8*d* shows the relative position of the wavelengths in the system for different optical splitters when the confocal channel processes anti-Stokes radiation of anti-Stokes wavelength, $\lambda_{anti-Stokes}$.

It should be obvious for those skilled in the art that the interface optics 12 can be coaxial and the fixation lamp and the source 126 can be applied by means known in the art at 90° to the imaging beam 9 via the interface optics splitter working in transmission for the beam 9 and in reflection for the excitation source 126 and the fixation lamp 124. In this case, the spectral characteristics of the interface optics splitter 123 are complementary to the curves in the insets in FIGS. 8*b* and 8*d*, for instance in FIG. 8*b* left, top and middle, 123 should be a cold mirror and in the bottom, 123 a notch filter, etc.

Figure 8E:
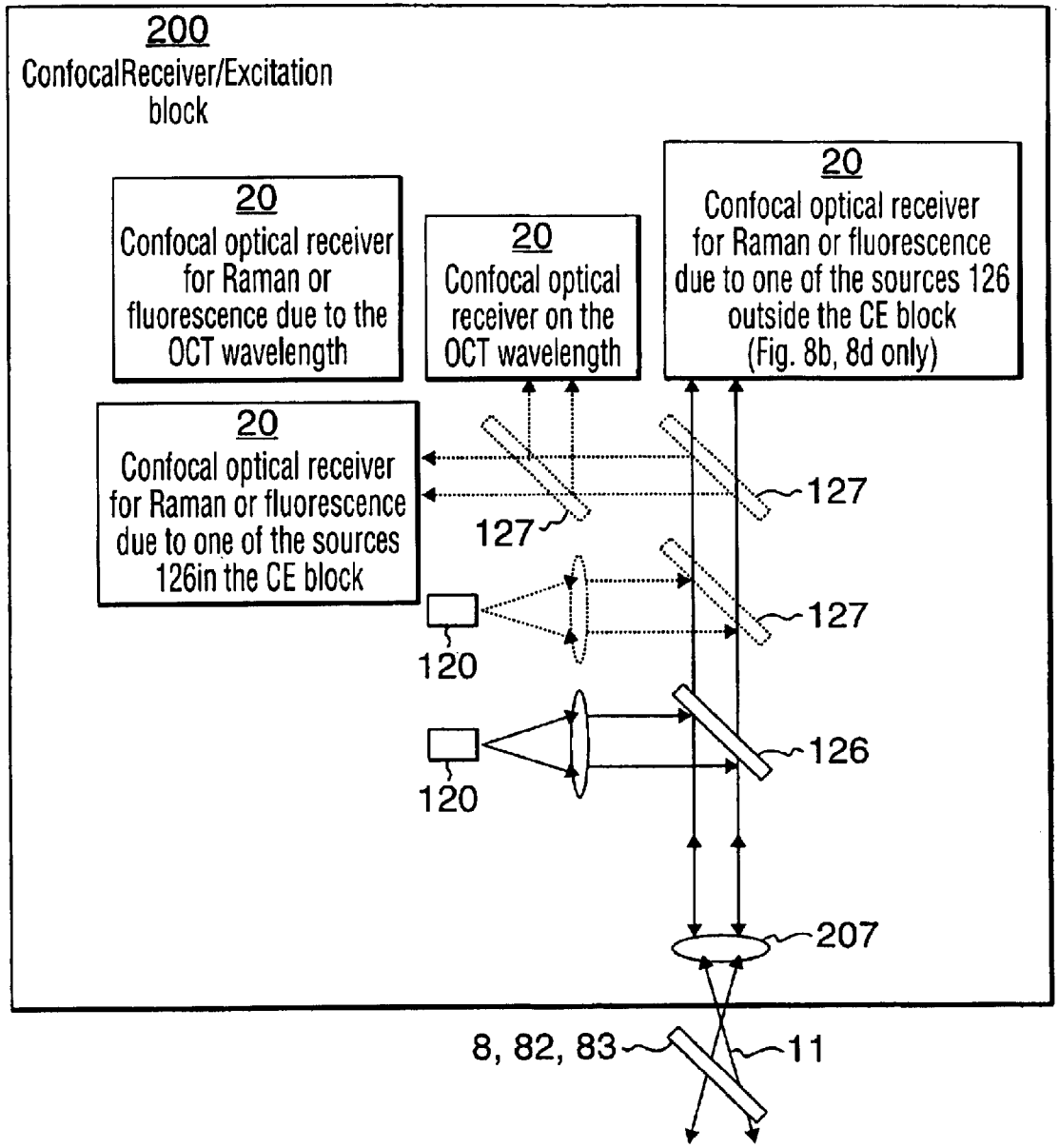
FIG. 8e is a different embodiment of the invention, where excitation sources and confocal optical receivers are placed on the same side of the optical splitter.

FIG. 8*e* is a different embodiment of the invention, useful for fluorescence or Raman studies, where excitation sources, 120 (termed as internal, in opposition to the source 126, which was termed external) and confocal optical receivers, 20, are placed inside a block Confocal receiver/excitation, (CE), 200, which can be placed in the beam 11 in FIGS. 8*a–d*, and replaces the single confocal optical receiver 20. Using similar terminology to that introduced before, when the block CE is used in FIG. 8*a* or 8*b*, the configuration is designated as R-OCT/T-CE, where the optical splitter 8 is used in reflection by the OCT channel and in transmission by the CE block. When the block CE is used in FIG. 8*c* or 8*d*, the configuration is designated as T-OCT/R-CE, where the optical splitter 8 is used in transmission by the OCT channel and in reflection by the CE block. The spectral content, useful for the block CE, and which covers the excitation bands of the sources 126 and the fluorescence/Raman bands emanated by the object, are termed as the CE band from now on. Optical splitters 226 are used to introduce the excitation radiation from sources 120 into the beam 11, to induce fluorescence or Raman emission in the object. The back-scattered signal from the object contains the fluorescence or Raman signal and the back-scattered radiation on the wavelength of the OCT signal. If the band of the fluorescent/Raman radiation on one hand and the band of the OCT radiation on the other hand are sufficiently distant apart, they can be separated in the confocal optical receiver 20 by using configurations as shown in FIGS. 4*d–f*. The configuration for focusing which matches the block 200 in FIG. 8*e*, with convergent beams 11 and 4, is similar to that in FIG. 2, in which case the configuration of confocal receiver in FIG. 4*d*, or 4*e* can be employed, however it should be obvious for those skilled in the art that the configuration shown in FIG. 3 can be used in FIG. 8*e*, in which case the lens 207 is removed and the configuration of confocal receiver in FIG. 4*f* can be employed instead, with spectral filtering elements to favour the band desired and attenuate the OCT wavelength and the excitation wavelength. The optical splitter, 8, can be either a large bandwidth beams-splitter, or a band-pass filter 82 on the CE band with a high reflectivity at the wavelength emitted by the source 50 or 500, or a notch filter 82 centred on the wavelength emitted by the source 50 or 500 with high transmission for the CE band, or a cold mirror, a hot mirror or an edge filter, 83. It is obvious for those skilled in the art and in the light of the previous embodiments that the choice depends on how the OCT 40 and the block 200 share the optical splitter 8, i.e. which one uses the reflected beam and which one uses the transmitted beam and on the relative spectral position of the two bands, the band of the OCT source, 50(500) on one hand and the band of the CF block on the other hand.

For instance, when using fluorescein angiography in the eye, the OCT wavelength should be 790–870 nm, the excitation wavelength 494 nm, and the optical splitter is a hot mirror, 83, with an edge at 700 nm, or a notch filter, 82, tuned on the OCT wavelength and the CE splitter 226 is a cold mirror with the edge at 506 nm and the confocal optical receiver, 20, may be equipped with a notch filter 205 on the excitation wavelength 494 nm and with a pass-band filter, 204, on 518 nm to supplementary eliminate the excitation band and OCT band. The optional interface optics splitter could be a band-pass filter on red, 630 nm, with high reflectivity at both the OCT wavelength and the CE band, 460–550 nm. By using combinations of spectral beam-splitters 226 and 227, such as cold or hot mirrors, edge filters or band-pass or notch filters, different excitation sources, shown in dashed line, can be simultaneously put together in the output beam 11 and different confocal receivers, 20, shown in dashed line, can be tuned on the different fluorescence or Raman bands emanated form the object under the excitation of different internal excitation sources 120. In this way, the apparatus according to the invention operates with: (i) an OCT channel and one or more confocal channels tuned on different bands, such as (ii) fluorescence or Raman emanated from the object under the excitation of the different sources 120 or/and (iii) tuned on the fluorescence or Raman emanated from the object under the excitation of the source 50 (500). Alternatively, one of the confocal optical receiver 20 could be tuned on the wavelength of the OCT, 20. In this case, the optical splitter, 227, could be as before, either a large bandwidth beams-splitter, a band-pass filter on the band around the wavelength emitted by the source 50 or 500, or a notch filter centered on the fluorescence or Raman radiation emitted by the object, a cold mirror, a hot mirror or an edge filter. It is obvious obvious for those skilled in the art and in the light of the previous embodiments that the choice depends on how the two confocal optical receivers share the optical splitter 227, i.e. which one uses the reflected beam and which one uses the transmitted beam and on the relative spectral position of the two bands, of the two sources, 50 (500) and 126.

For such a configuration, the display device 19 requires simultaneous presentation on the PC screen of more than 2 images.

For instance, in the example above when using fluorescein angiography in the eye in connection with FIG. 8*e*, the splitter 227 could be a cold mirror with the edge at 650 nm, far away from the fluorescence band and the OCT band. For the OCT band, the optical splitter when implemented using a hot mirror 83 or a notch filter 82 allows a residual transmission of 5–10%, which then subsequently passes through the CE splitter 226 and the splitter 227, implemented using cold mirrors. Such a magnitude of the signal is sufficient for the implementation of a confocal channel at the OCT wavelength, as demonstrated in the paper "Noise Analysis of a Combined Optical Coherence Tomograph and a Coniocal Scanning Ophthalmoscope", published in Appl. Optics, Vol. 38, (1999), No. 10, pp. 2116–2127, authored by A. Gh. Podoleanu, D. A. Jackson, where 4.6–21% was demonstrated to be suitable for a signal to noise ratio as obtained in conventional SLOs. For such a configuration, the display device 19 requires simultaneous presentation on the PC screen of at least 3 images, OCT and confocal due to the source 50 (500) and at least one confocal on the fluorescence or Raman signal emanated from the object due to the internal excitation source 120.

Figure 8F:
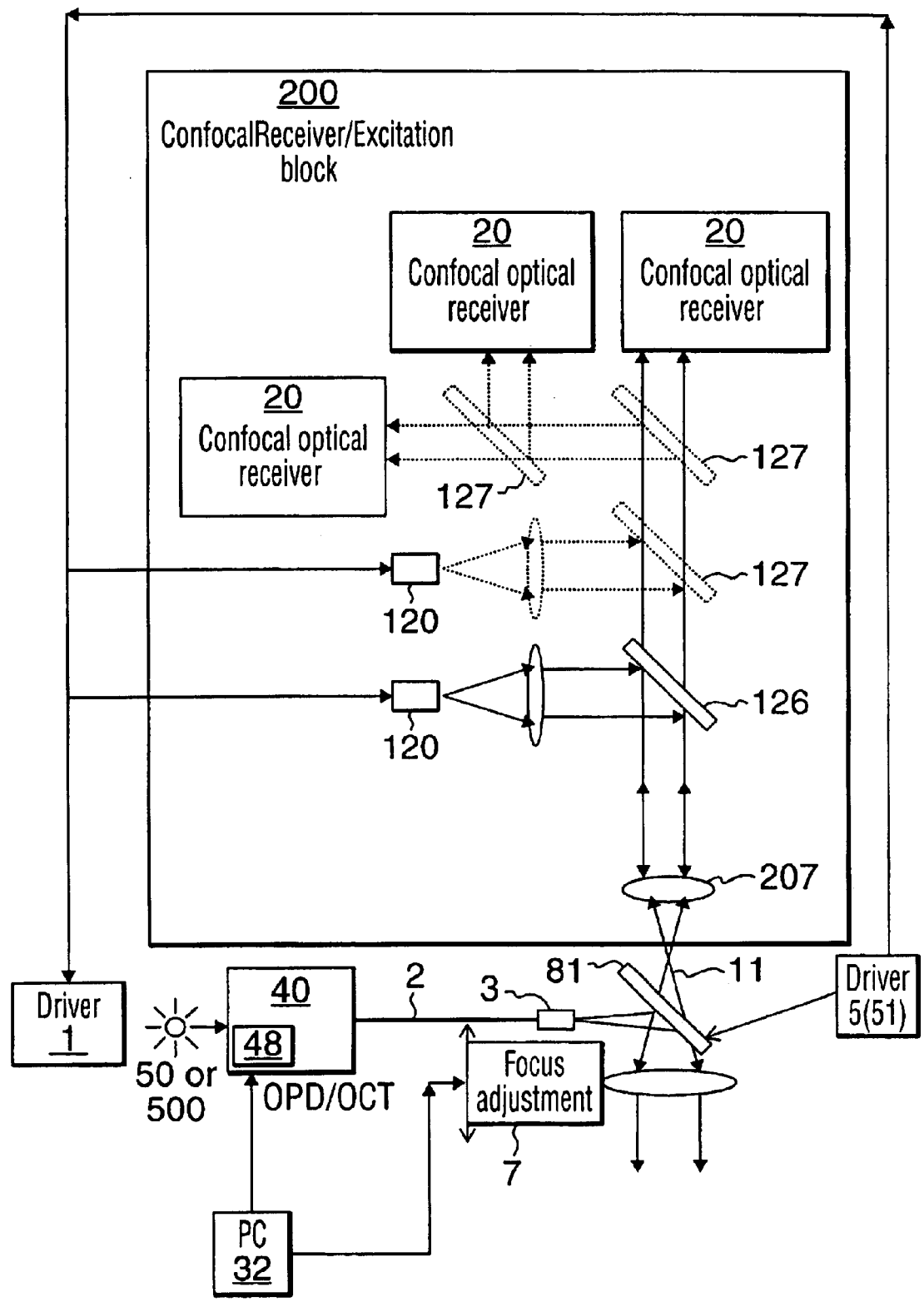
FIG. 8f is a replica of the embodiment in FIG. 8e, wherein the percentages of light returned from the tissue towards the OCT and the CE block can be adjusted.

FIG. 8f is a replica of the embodiment in FIG. 8e, wherein the percentages of light returned from the tissue towards the OCT and the CE block can be adjusted. In order to balance the amount of light diverted to the CE block, 200 the optical-splitter, 81, may have a gradual or a step deposition with height, which allows the reflectivity, η and transmission 1-η to vary With height, or with a lateral coordinate, allowing the returned irradiance to the block 200 to be varied from very low to very high values, as an example, from η=1% to 98% of $P_{object}$ O, where $P_{object}$ is the power delivered to the object and O is the reflectivity of the object. A driver 5, shifts the beam-splitter 81 vertically, or laterally, generally along the gradient of the deposition axis to adjust the percentage of light reflected and transmitted. When doing so, the driver may also act on the driver, 1, of the optical source, 50 or 500 and on the sources 120 in the block CE, to maintain the same power to the object. For those skilled in the art, it is evident that the mount of the beam-splitter 81 can be equipped with a micro-motor when the optical-splitter 81 is gradually deposited or can have two or more stable positions when the optical-splitter has step depositions. The driver 5 can be implemented by means known in the art, such as an electromechanical circuit to control a micro-motor for fine displacement along the gradient of the deposition axis, or a manual knob on the front panel of the instrument which is mechanically tied up to the mount of the beam-splitter.

As another alternative, the optical-splitter 81 may be a splitter with transmission and reflectivity controllable by an external field, for instance such as an electro-optic or a magneto-optic or a liquid crystal plate, which under the control of an electric field, or of a magnetic field or both, can have the reflectivity and transmission altered according to computer control, 32. In this case, the driver 51 applies suitable electric fields or magnetic fields or both to the beam-splitter element 81, by means known in the art.

It should also be evident for those skilled in the art that the same configuration of control, using the same optical-splitter, 81, with graded deposition or under external field control, and driver 5 or driver 51, respectively, can be applied to the version of focusing diagram in FIG. 3, in which case the confocal optical receiver as shown in FIG. 4f should be used instead of configurations 4d or 4e.

Another embodiment of the invention is shown in FIG. 9a, where two low coherence sources with different coherence lengths are used, emitting on the same central wavelength, 52 and 50 (or a source with adjustable coherence length, 500). The drivers of the two sources, 72 and respectively 70, are sequentially switched off and on for the duration of each ramp signal 39, applied by generator 35 to the line scanner, for instance for the positive slope, the source 52 is on and source 50 (or 500) is off and for the next slope, negative, the source 52 is switched off while the source 50 (or 500) is on. In this way, two mirrored OCT images of different depth resolution, for the same depth, are displayed by the dual channel imaging means, 19, under the control of the PC, 32. Different ways to synchronize the switching are possible, one is illustrated in FIG. 9a, where an inverter, 71, of the line sync signal, 38, is used to insure that one source is off and the other is on. To compensate for the signal delay in the scanners and circuits, a delay block, 73, is used. For instance, if a 1 kHz triangle is used, the line in the raster lasts 1 ms with 0.5 ms under one source illumination and the next 0.5 ms under the illumination of the other source. If as for example, the two sources have 20 and 300 μm coherence length, then two OCT images with 20 and 300 μm depth resolution will quasi-simultaneously be displayed side by side, along with a confocal image, i.e. a pair of OCT and confocal image for each source is displayed for each ramp of the triangle signal.

Due to the high coherence length of one of the source, the image may look very similar to the image generated by the confocal channel, in which case a confocal channel may not be needed for guidance and be removed, in which case 8 is a simple mirror in FIG. 9a and in practice can be removed and better quality OCT images can be obtained. In this case, the apparatus has only two quasi-simultaneous OCT channels.

Alternatively, the block CE of excitation sources and confocal optical receivers, 20 in the CE block 200 may be used instead of a single confocal optical receiver. In this case, pairs of OCT confocal images are switched on and off, and they may be simultaneous with other confocal images, delivered by the confocal optical receivers in the CE block, as described in connection to FIG. 8e. For instance, a confocal optical receiver in the CE block may be tuned on the fluorescence or Raman radiation emitted from the object due to the corresponding internal excitation source in the CE block or/and tuned on the fluorescence or Raman radiation emitted from the object due to one or both of the sources which make the radiation source, in which case such image will toggle at the same rate with switching the sources.

The different regimes of operation are shown in the inset at the bottom of the diagram in FIG. 9a.

It is obvious for those skilled in the art that the embodiment in FIG. 9a can equally be implemented in configuration T-OCT/R-C and T-OCT/R-CE when using the CE block 200.

The same set-up in FIG. 9a can be implemented with two optical sources, 50 (500) and 52 of different wavelengths and similar or dissimilar coherence lengths. As illustrated, the configuration in FIG. 9a leads to the production of two pairs of images of different coherence length. When the OCT interferometer 40, the optical-splitter 8 and all the other following elements such as lenses 60, 61, and 62, the transverse scanner mirrors, 10 and the interface optics 12 are of large bandwidth to accommodate two different wavelengths, from two sources 50 (500) and 52, then the same configuration in FIG. 9a can serve to produce two pairs of images, OCT and confocal at two different wavelengths.

Figure 9B:
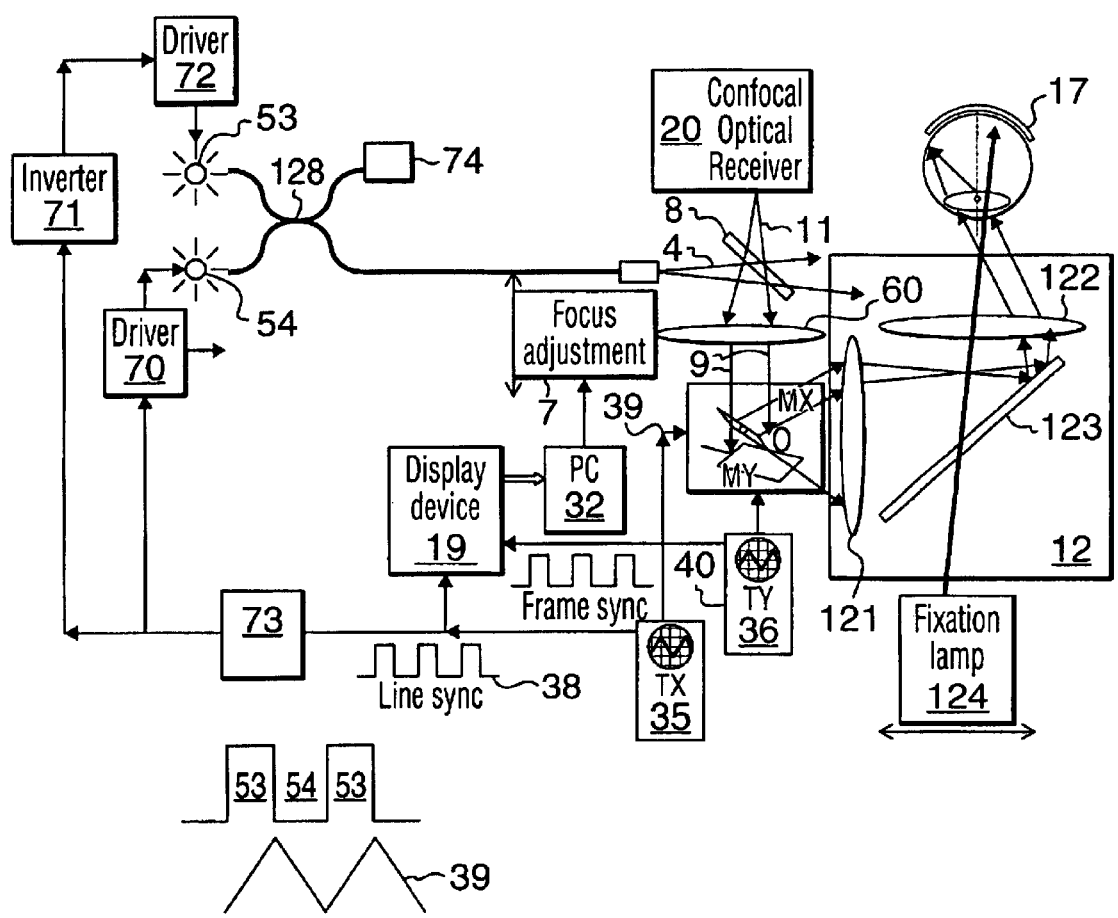
FIG. 9b shows in diagrammatic form, a different embodiment of the optical mapping apparatus with adjustable depth resolution according to the invention with quasi-simultaneous display of two confocal images only, and using two sources of different wavelengths.

FIG. 9b shows in diagrammatic form, a different embodiment of the optical mapping apparatus with adjustable depth resolution according to the invention with quasi-simultaneous display of two confocal images only, using two sources of different wavelengths, 53 and 54. The drivers of the two sources, 72 and respectively 70, are sequentially switched off and on for the duration of each ramp signal, 39, applied to the line scanners for instance for the positive slope, the source 53 is on and source 54 is off and for the next slope, negative, the source 53 is switched off while the source 54 is on. In this way, two mirrored confocal images, for the same depth, are displayed by the imaging means, 19, under the control of the PC, 32. Different ways to synchronize the switching are possible, one is illustrated in FIG. 9b, where an inverter, 71, of the line sync signal, 38, is used to insure that one source is off and the other is on. To compensate for the signal delay in the transverse scanners and circuits, a delay block, 73, is used. For instance, if a 1 kHz triangle is used, the line in the raster lasts 1 ms with 0.5 ms under one source illumination and the next 0.5 ms under the illumination of the other source. If as for example, the two sources have 670 nm and 820 nm, then two confocal images will quasi-simultaneously be displayed side by side, a confocal image for each source. The optical splitter 8 and the elements after the optical splitter have to be large band for both wavelengths used.

Figure 9C:
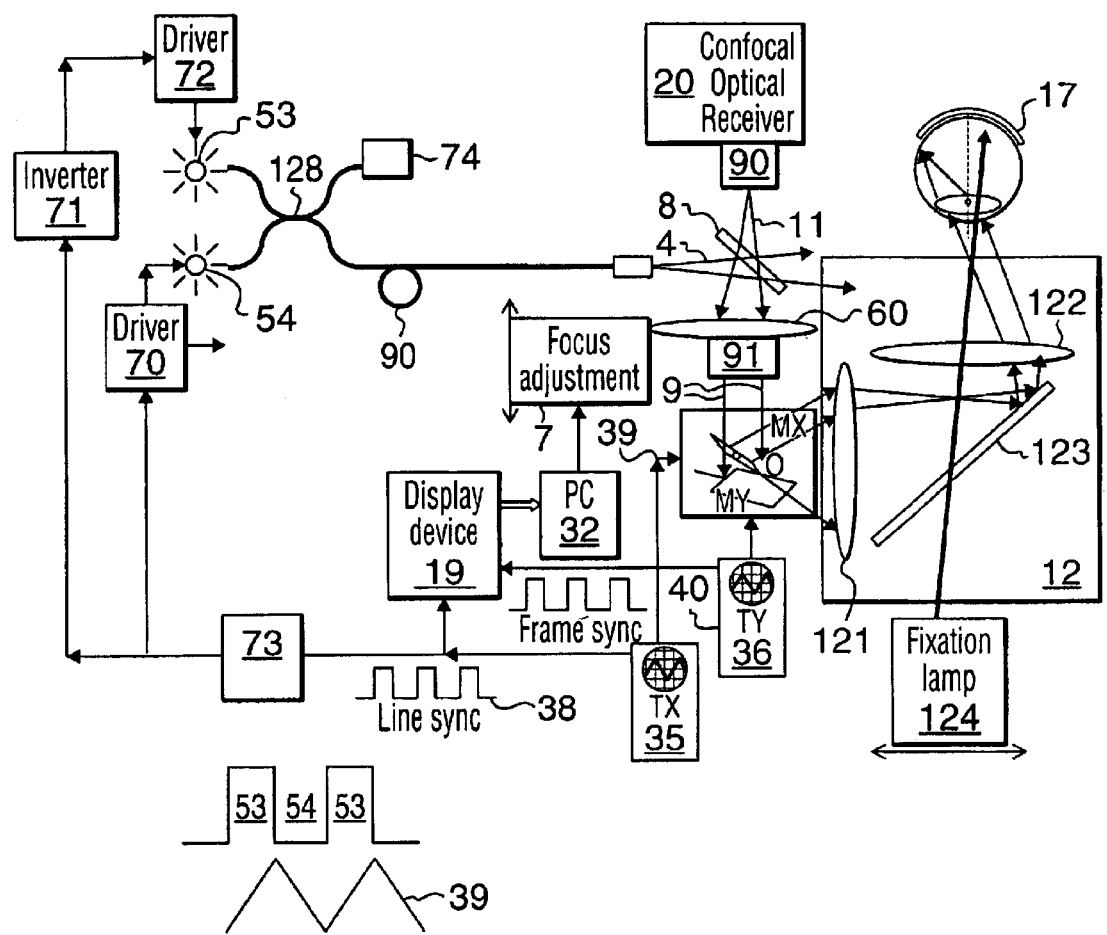
FIG. 9c shows the embodiment of the optical mapping apparatus in FIG. 9b using a polarisation sensitive optical-splitter.

To reduce the attenuation in the optical-splitter, a polarisation sensitive beam-splitters, 85 can be used, as shown in FIG. 9c. In this case, the two sources, 53 and 54 are polarised linearly in the same direction, using a polariser, 90, which could be a fibre polariser or a bulk element when the two sources are superposed using bulk optical elements, direction of polarisation which is allowed through the beam-splitter 85, followed by a quarter wave plate, 91, which could be placed before or after the lens 60, or after the scanner head 10, shown after the lens 60 in FIG. 9c, oriented at 45° and the returned reflected signal will then pass through the polarisation sensitive beam-splitter 85 towards the confocal optical receiver, 20, which supplementary may have a polariser element, 90.

FIG. 10 shows images collected from the finger skin with the embodiment in FIG. 9a, where two pairs of images are displayed, each pair generated by a low coherence source where the two sources have different coherence lengths. The images on the left column are collected with a three electrode laser, of coherence length larger than 200 μm. Such a source and the value of adjustable coherence length for en-face OCT imaging were described in the paper "OCT En-face Images from the Retina with Adjustable Depth Resolution in Real Time", by A. Gh. Podolean, J. A. Rogers, D. A. Jackson, published in the IEEE Journal of Selected Topics in Quantum Electron., 1999, 5, No.4, 1176–1284. The images in the right column in FIG. 10 are obtained with a superluminiscent diode with a coherence length smaller than 20 μm. Due to the larger coherence length, the images in the left column look less fragmented The confocal and OCT images in FIG. 10 allow the user to make quantitative assessments. The two confocal images will have the same depth resolution, determined by the optical elements in the apparatus which transfer the optical signal of the con focal channel, despite the fact that the two sources have different coherence lengths. The ratio of their brightness evaluated on each pixel depends on the ratio of the powers of the two sources used. The two OCT images will have different depth resolution and their brightness will depend on the depth resolution versus tissue thickness as we tell as on the optical source power. Using the brightness registered in the two confocal images, normalisation of the brightness in the two OCT images can be performed.

The display of the two images in the embodiment of the invention described in FIGS. 9a and 9b has the disadvantage of each of the two images being the mirror of the other. The images on the left mirror the images on the right due to the specific way the image is generated by the display scanning means, 19. Two possibilities exist to correct for this problem. After the acquisition, the images on the right can be flipped horizontally to gain the aspect of images in the left. This requires extra processing of the image after the acquisition. A different possibility is described in the embodiment in FIG. 11a, where the display of the image is performed in a different way.

Instead of synchronising with TTL signals from the line generator, the angular positions of the two transverse scanners, line and frame scanners, is translated into the horizontal position in the image displayed. The position of the pixel in the image is determined by the amplitude of the angular scanning, irrespective of the sign of variation.

Figure 11A:
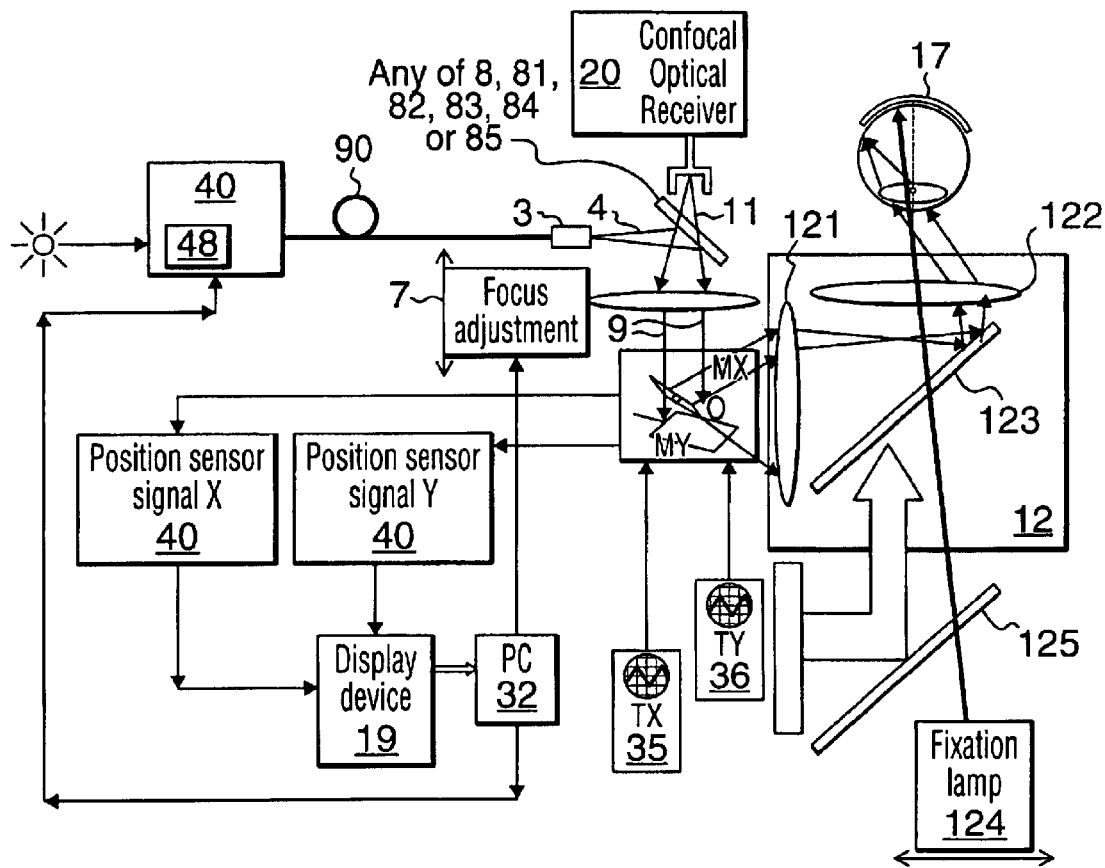
FIG. 11a shows in diagrammatic form, another embodiment of the optical mapping apparatus with adjustable depth resolution wherein the image coordinate is controlled by position sensitive detectors of the angular deviation of the transverse scanners.

Another advantage of the procedures used in FIGS. 9a–c and 11a is that a full temporal utilisation of the transverse scanner is now accomplished. When driving a galvanometer scanner at more than 0.5 kHz, usually, the fly back is larger than 30% and the signal collected during the fly back is discarded. Additionally, the life time of the galvo-scanners is increased by driving the scanners with triangles instead of ramps followed by sudden drops. The procedure in FIG. 11a allows sinusoidal driving signals to be used, which increases the galvo-scanner lifetime supplementary. The embodiment in FIG. 11a is also suitable for resonant scanners.

It is obvious for those skilled in the art that the signal driving the transverse scanner may have other forms different from triangle or sinusoid and the only essential feature for this operation is that the signal is periodic. All previous embodiments, as presented in connection to FIGS. 2, 3, 5, 6, 7, 8, 9 can be implemented using this procedure of generating the images. Therefore, the optical-splitter can be either a large band-beamsplitter, 8, or a graded beam-splitter, 81, or a narrow band filter, 82 or an edge filter, or a cold or hot mirror, 83, or a combination of the above, 84, or a polarisation sensitive beam-splitter, 85, in which case the signal in the OCT channel is linearly polarised and the polarisation state of the output is adjusted using the polariser 90, which could be a fiber polariser or a dycroic sheet or other bulk polariser, in such a direction that all light passes through the polarisation sensitive optical-splitter 85. The light returned from the object has different polarisation orientations and some of the light will go back to the OCT and some will go to the block CE, 200.

The embodiment in FIG. 11b implements the functionality of the embodiment in FIG. 9a using position sensing of the transverse scanners in a similar way to that employed in FIG. 11a, with the difference that instead of one image as in FIG. 11a, pairs of images are generated for each sign variation of the periodic signal applied to the line scanner. During one sign of the variation of the periodic signal applied to the line scanner, a line in a first image is built on the screen of the PC controlled by the displaying means while during the other sign, the line in a second image is built. The horizontal position of the spot on the PC screen is proportional to the scanner position and in this way, two images are produced. The inset in FIG. 11b shows the two frames side by side, where in both frames the left of the object is on the same side of each pair of images, different from the case in FIGS. 9a–c where the two images were mirrors of each other, as exemplified in FIG. 10.

The diagrams in FIGS. 11a and 11b show configurations R-OCT/T-C (R-OCT/T-CE), however it should be obvious for those skilled in the art that the same embodiments as in FIGS. 11a and 11b are applicable for the configuration T-OCT/R-C (T-OCT/R-CE).

As illustrated, the configuration in FIG. 11b leads to the production of two pairs of images of different coherence length. When the OCT interferometer 40, the optical-splitter 8 or graded beam-splitter 81, and all the other following elements such as lenses 60, 61, and 62, the transverse scanner mirrors, 10 and the interface optics 12 are of large bandwidth to accommodate two different wavelengths, from two sources of low coherence 50 or with adjustable coherence length 500, then the same configuration in FIG. 11b can serve to production of two pairs of images, OCT and confocal at two different wavelengths.

Due to the high coherence length of one of the source, the image may look very similar to the image generated by the confocal channel, in which case a confocal channel may not be needed for guidance and may be removed. In this case 8 is a simple mirror in FIG. 11b and in practice can be removed, and the apparatus has only two quasi-simultaneous OCT channels.

Alternatively, the block CE of excitation sources 120 and confocal optical receivers 20 in the CE block 200 may be used instead of a single confocal optical receiver 20. In this case, pairs of OCT/confocal images are switched on and off, and they may be, simultaneous with other confocal images, delivered by the confocal optical receivers in the CE block, as described in connection to FIG. 8e.

Similar to FIG. 9a, the different regimes of operation are shown in the inset at the bottom of the diagram in FIG. 11b.

FIG. 11c shows in diagrammatic form, a different embodiment of the optical mapping apparatus according to the invention where the image coordinate is controlled by position sensitive detectors of the angular deviation of the transverse scanners to quasi-simultaneously display two confocal images, using two sources of different wavelength, 53 and 54. The drivers of the two sources, 72 and respectively 70, are sequentially switched off and on for the duration of each half of the periodic signal applied to the line scanner, for instance for the positive slope, the source 53 is on and source 54 is off and for the next slope, negative, the source 53 is switched off while the source 54 is on. In this way, two confocal images, for different wavelength and the same depth, are displayed by the imaging means, 19, under the control of the PC, 32. Different ways to synchronize the switching are possible, one is illustrated in FIG. 11c, where an inverter, 71, of the line sync signal, 39, is used to insure that one source is off and the other is on. To compensate for the signal delay in the transverse scanners and circuits, a delay block, 73, is used. For instance, if a 1 kHz triangle is used, the line in the raster lasts 1 ms with 0.5 ms under one source illumination and the next 0.5 ms under the illumination of the other source. If as for example, the two sources have 670 nm and 820 nm, then two confocal images will quasi-simultaneously be displayed side by side, a confocal image for each source. The optical splitter 8 and the following components from the optical splitter up to the object, such as focusing elements and the transverse scanners have to be large band for both wavelengths used. The synchronisation signal is collected from the position sensor in FIG. 11b but equally could be obtained from the generator 35 which determines the line in the displayed image.

To reduce the attenuation in the optical-splitter, a polarisation sensitive beam-splitters, 85 can be used, similar to the case shown in FIG. 9c, as illustrated in FIG. 11d. In this case, the two sources, 53 and 54 are polarised linearly in one direction, using a polariser, 90, which could be a fibre polariser or a bulk element when the two sources are superposed using bulk optical elements, direction of polarisation which is allowed through the beam-splitter 85, followed by a quarter wave plate, 91, oriented at 15°, which could be placed before or after the lens 60, or after the scanner head 10, but is shown after the lens 60 in FIG. 9d. The returned reflected signal will then pass through the polarisation sensitive beam-splitter 85 towards the conofocal optical optical receiver 20, which supplementary may have a polariser element, 90.

It is obvious for those skilled in the art that the embodiment in FIGS. 11a and 11b can equally be implemented in configuration T-OCT/R-C as explained in conjunction with the embodiments in FIGS. 8c and 8d.

Figure 12A:
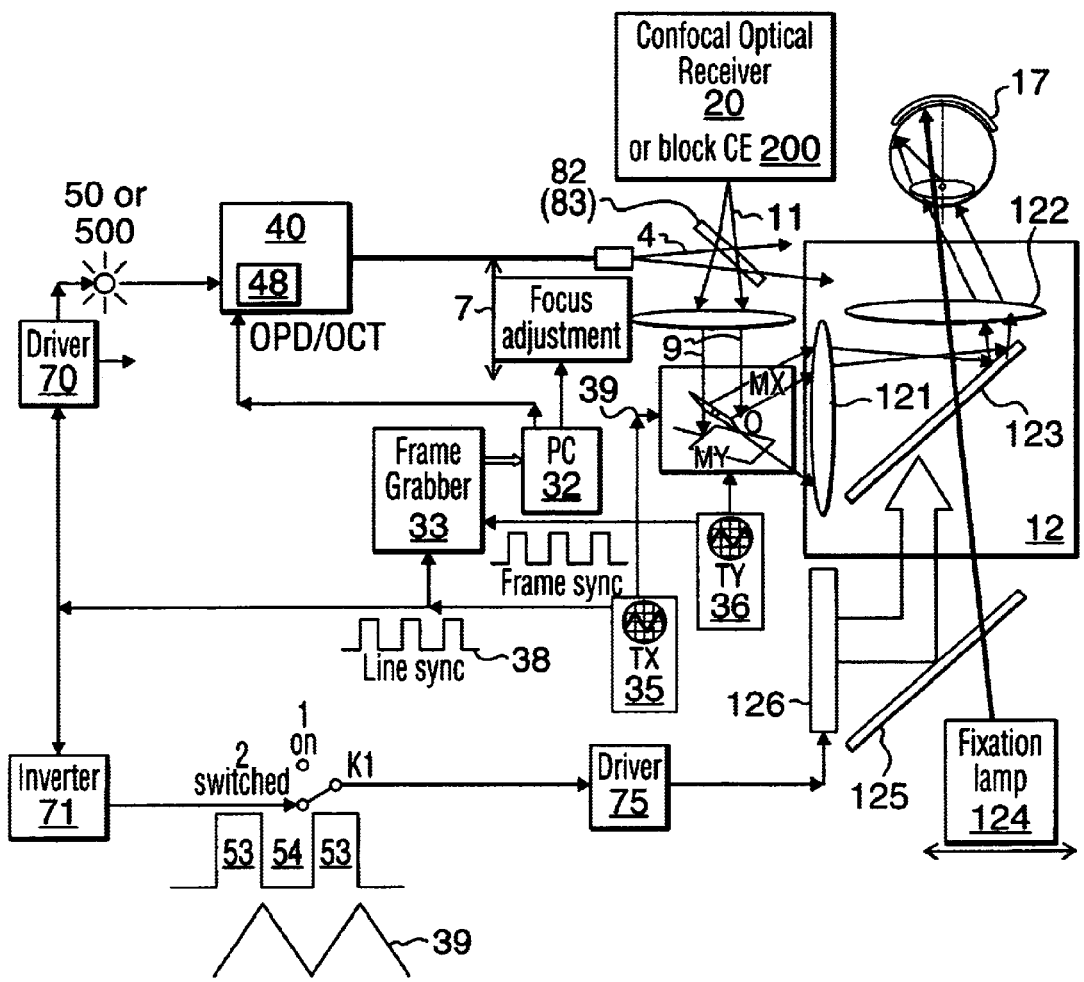
FIG. 12a shows in diagrammatic form, another embodiment of the optical mapping apparatus with adjustable depth resolution according to the invention with quasi-simultaneous display of two images with different depth resolution, one being OCT and the other being confocal, from the fluorescence or Raman emission, wherein the wavelengths of the source used for the OCT channel and the fluorescence band are so closed to each other that they cannot be spectrally separated.

FIG. 12a shows in diagrammatic form, another embodiment of the optical mapping apparatus with adjustable depth resolution according to the invention with quasi-simultaneous display of two images, with different depth resolution, one OCT and the other confocal from the fluorescence. When the OCT wavelength is close to the fluorescence (or auto-fluorescence) wavelength, the fluorescence signal cannot be separated in the confocal channel from the reflected signal on the OCT wavelength. For instance, this is the case when using ICG angiography in the eye, and the OCT wavelength is in the 800 nm band. Therefore, the low coherence source used for the OCT must be switched off when the auto-fluorescence or fluorescence signal is collected. As shown in the $4^{th}$ column of the table in FIG. 12a bottom, in the first part of the ramp signal applied to the transverse scanning means 10, an OCT image and an insignificant confocal image is generated, while in the second part of the ramp, no OCT image is generated but with an auto-fluorescence or fluorescence image in the confocal channel, such as an ICG fluorescence image for instance. If additionally, the excitation beam, emitted by the source 126, deteriorates the S/N ratio in the OCT channel, then the switch K1 is switched to position 2 and the source 126 is switched of during the first part of the ramp 39 and is switched on during the second part of the ramp 39, via the inverter 71 and driver 75, and the images collected are described in the $4^{th}$ column of the table in FIG. 12a top. The optical splitter is similar to that in FIG. 8b, as explained in the inset table.

Figure 12B:
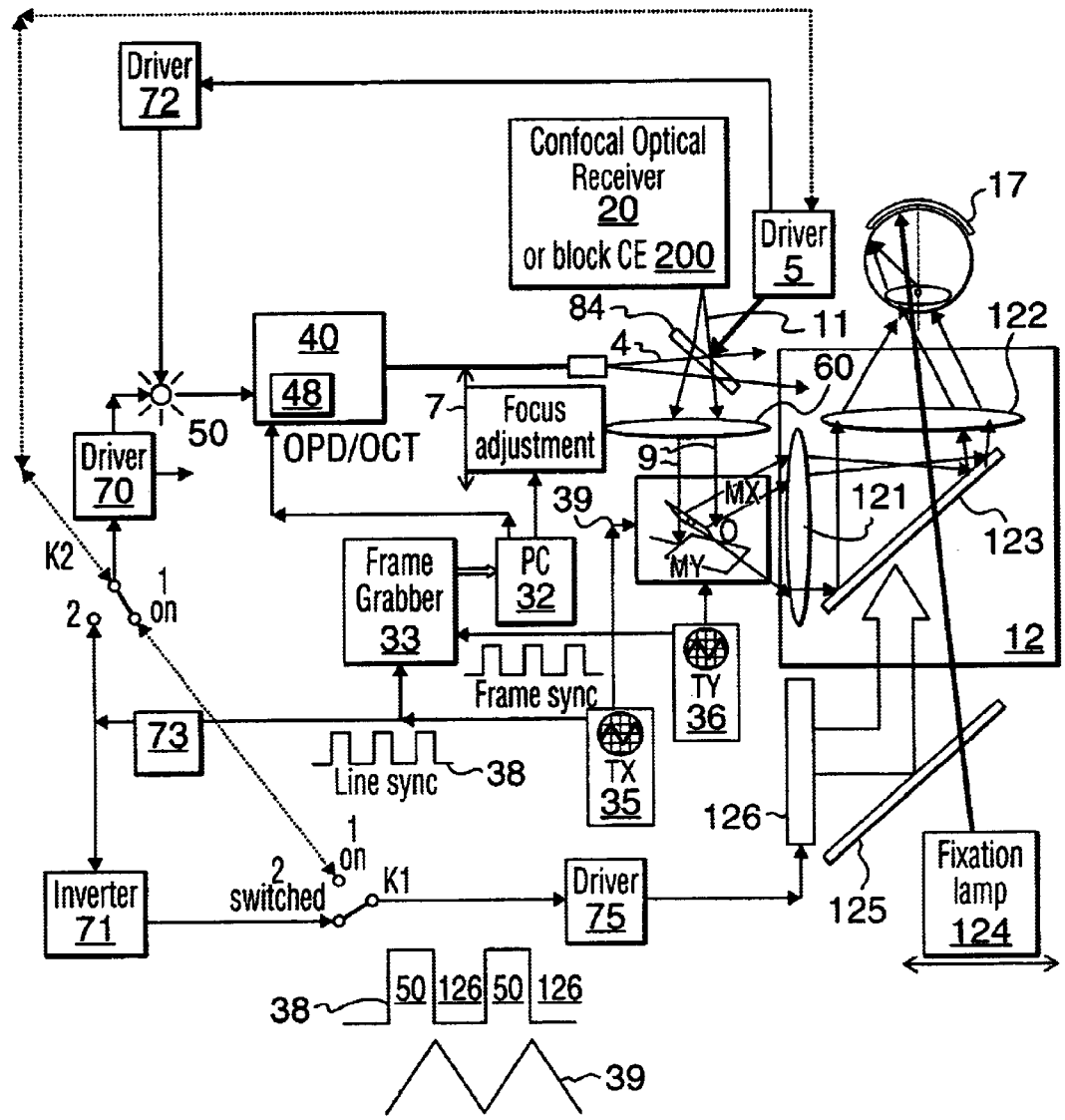
FIG. 12b shows in diagrammatic form, another embodiment according to the invention with enhanced versatility in comparison with the configuration in FIG. 12a., where the functionality of the optical-splitter shared by the confocal and the OCT channels is synchronously changed with the different driving conditions of the OCT source and the external excitation source in order to allow different regimes of operation to be accomplished.

FIG. 12b shows in diagrammatic form, another embodiment according to the invention with enhanced versatility in comparison with the configuration in FIG. 12a. The optical-splitter, 84, is similar to that used in FIG. 7b but is made from two, three or four parts along a reflectivity variation axis, which could be vertical, horizontal or diagonal axis, and could include a conventional large band beam-splitter 8, continuing with a graded deposition, 81, then continuing with one of two spectrally selective elements, a band pass or a notch filter, 82 and then a cold or a hot mirror, or an edge filter, 83. The driver 5 suitably shifts the optical-splitter 84 along the variation axis, to introduce one of the parts into the beam; the driver being similar to the case explained above in connection to FIG. 5a and FIG. 7b. In this case, the instrument is preferably operated in the regimes of operation as described in the inset table in FIG. 12b. The modes of operation can include the following:

(i) Dual channel OCT and confocal on the same wavelength, of the low coherence source, 50 or of the source with adjustable coherence length, 500, with the optical-splitter 84 in that position where the large bandwidth plate beam-splitter, 8 is positioned in the beam, and the source 126 is off and the OCT source is continuously run, similar to the embodiment in FIGS. 2a–d;

(ii) Dual channel OCT and confocal on, the same wavelength with adjustable ratio of the signals in the two channels, with the optical-splitter 84 in that position, where the gradually deposited beam-splitter, 81 intersects the beam 4, and the optical-splitter can be conveniently positioned in the beam to after the percentages of the light in the two channels, using the same driver 5, or it can be implemented with a liquid crystal oil, in which case an extra driver 51 is used to control its transmission and reflection, similar to the embodiment in FIG. 5;

(iii) Dual channel OCT and confocal fluorescence wherein the two wavelengths are far away and can be spectrally separated and the excitation source 126 and the OCT source, 50 or 500 are continuously run in which case the optical-splitter 84 is in that position, where a band-pass filter 82 (configuration R-OCT/T-C) or a notch filter 82 (configuration T-OCT/R-C) is inserted into the beam 4, the center of the band pass or the notch filter being on the fluorescence or Raman wavelength, and where other spectral elements in the confocal optical receiver, as seen in FIG. 4, can be used to eliminate the signal on the OCT wavelength, emitted by source 50 or 500 and emitted by the excitation source, 126, similar to the embodiment in FIG. 8b;

(iv) Triple channel, with simultaneous dual channel OCT and confocal which are quasi-simultaneous with a confocal fluorescence channel, when the two wavelengths, (OCT and fluorescence) are close to each other, in which case the optical-splitter is in a position, to insert the part 83 into beam 4, an edge filter, a cold or a hot mirror, or where the optical-splitter is in a position to insert a band-pass filter 82 (configuration R-OCT/T-C) or a notch filter 82 (configuration T-OCT/R-C) into the beam 4, the centre of the band pass or the notch filter being on the fluorescence or Raman wavelength, and where other spectral elements in the confocal optical receiver, as seen in FIG. 4, can be used to eliminate the signal on the OCT wavelength, emitted by source 50 or 500 and emitted by the excitation source, 126, similar to the embodiment in FIG. 8b, and the OCT source is sequentially switched on and off by the generator of the ramp signal, 35, via line control 38, in the same way as explained in FIG. 9a. The fifth column (bottom) in the table in FIG. 12b shows the pairs of images generated during each ramp of the triangle signal delivered by the generator 35. The source 126 is on all of the time and it is considered that it does not impair the operation or the OCT channel. Useful images are: the pair of (1) the OCT image (left-top) and (2) confocal image (left-bottom) during the ramp when the OCT source is on and the (3) fluorescence confocal image (right-bottom) during the ramp when the OCT source is off. During the ramp while the OCT source is on, the confocal image (left-bottom) is the result of both the fluorescence signal as well as due to the residual signal on the OCT wavelength which passes through the spectral beam-splitter 83 or the band-pass filter or notch filter 82, (v) The same as (iv) above, where additionally, the excitation source 126 is sequentially switched on and off by the generator of the ramp signal, 35, in the same way as explained in FIG. 11a, synchronous with the sequential switch off-and on of the OCT source in such a way that when the OCT source is on the excitation phase, the source is off and respectively, when the OCT source is off the excitation phase, the source is on. As seen in the fifth column (top), useful images are the pair of (1) OCT image (left-top) and the (2) confocal image (left-bottom) during the ramp when the OCT source is on and the excitation source is off and the (3) fluorescence confocal image (right-bottom) during the ramp when the OCT source is off and the excitation source is on. During the ramp when the OCT source is on, the confocal image (left-bottom) is the result of the residual signal on the OCT wavelength which passes through the spectral beam-splitter 83 or the band-pass filter or notch filter 82, sufficient to generate a good quality confocal image. In this regime, the eventual noise in the OCT channel generated in the configuration explained at (iv) above, due to excitation source 126, is eliminated.

Such an optical splitter, 84, can be devised by means known in the art, for instance using different depositions to achieve either large bandwidth splitting, uniform or graded or spectrally selective to achieve behaviour of the cold or hot mirror or edge filter type, or notch filter or band-pass filter.

All the elements following the complex optical splitter 84 in FIG. 12b along the path of the beam 9 containing the wavelengths of both the OCT source 50 (500) and fluorescence signal due to the excitation source 126 are preferably large bandwidth, compatible with the two bands used.

Figure 12C:
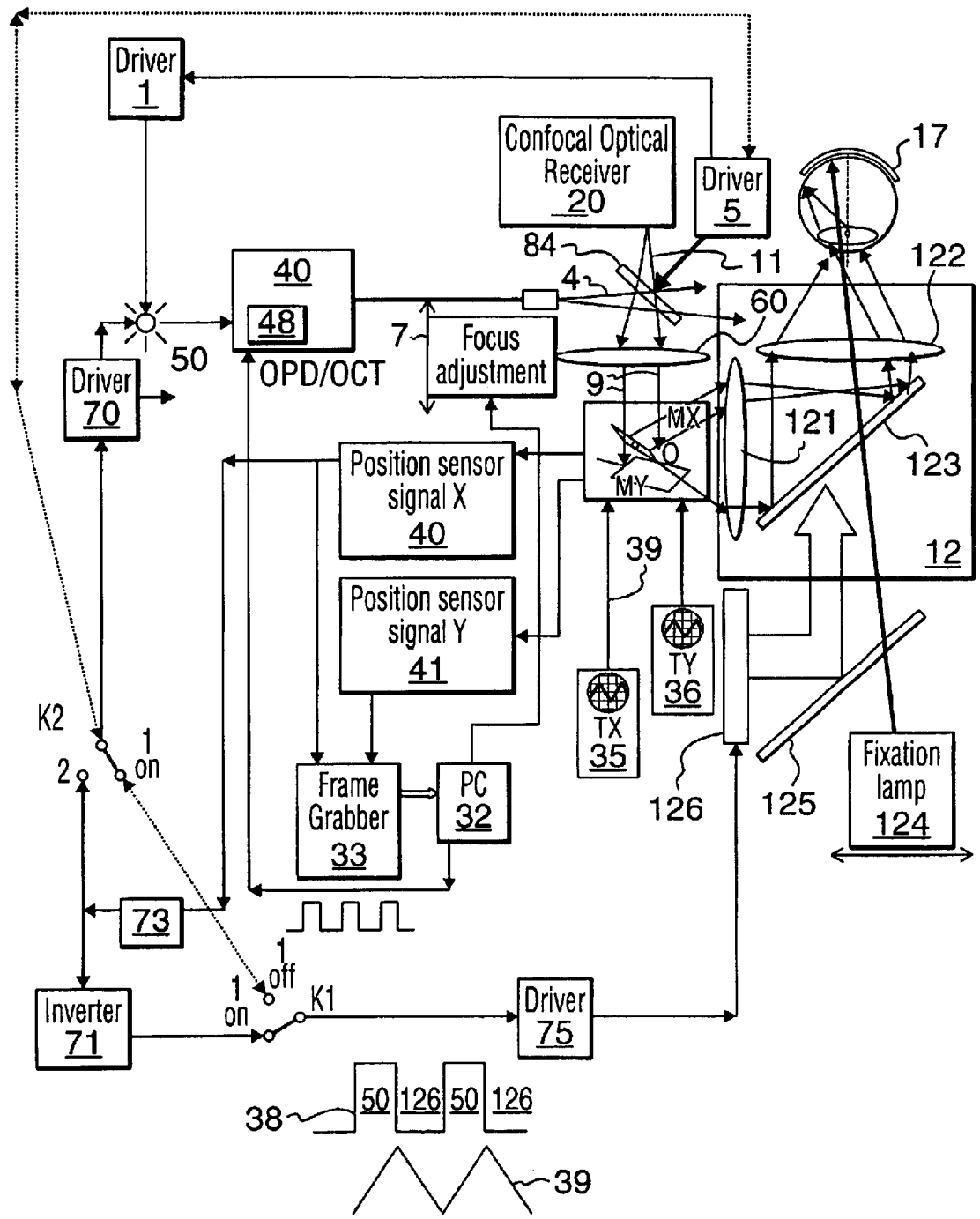
FIG. 12c shows in diagrammatic form, another embodiment according to the invention with enhanced versatility in comparison with the configuration in FIG. 12a., wherein the functionality of the optical-splitter shared by the confocal and the OCT channels is synchronously changed with the different driving conditions of the OCT source and the external excitation source in order to allow different regimes of operation to be accomplished, and wherein the image coordinate is controlled by position sensitive detectors of the angular deviation of the transverse scanners and the switching of the two sources is controlled by the position sensitive detector of the angular deviation of the line scanner.

FIG. 12c shows in diagrammatic form, another embodiment according to the invention with enhanced versatility in comparison with the configuration in FIG. 12a., where the functionality of the optical-splitter shared by the confocal and the OCT channel is synchronously changed with different driving conditions of the OCT source and external excitation source to allow different regimes of operation to be accomplished, with the same hardware, as described in the table inset, and where the image coordinate is controlled by position sensitive detectors of the angular deviation of the transverse scanners. The same regimes of operation as described in connection to the embodiment illustrated in FIG. 12b are achievable. However in comparison with FIG. 12b, the switching of the two sources is now controlled by the position sensitive detector of the angular deviation of the transverse scanner which determines the line in the raster.

It should be obvious for those skilled in the art that similar focusing configuration as that described in FIG. 3 can equally be used in the embodiments in FIGS. 5a, 5b, 6a, 6b, 7a–d, 8a–d, 9a–c, 11a–d, 12a–c.

It is also obvious for those skilled in the art that the embodiment in FIGS. 12a–c can equally be implemented in configuration T-OCT/R-C, as explained in conjunction with the embodiments in FIGS. 8c and 8d.

It should also be obvious for those skilled in the art that when using polygon mirrors in the embodiment in FIGS. 9a, 9b, 9c, 11b–d, 12a–d that the same regimes of operation can be implemented applying the switching of the sources at every new facet of the polygon mirror and separating the pair of images generated using the odd facets from the images generated on the even facets.

When using the block CE in FIGS. 12a–c, additional to the images produced in different regimes of operations as described above, one or more confocal images are displayed, on the fluorescence or Raman emanated from the object due to one or more respective excitation sources in the block CE and/or on the wavelength of the source 50 (500).

Figure 13:
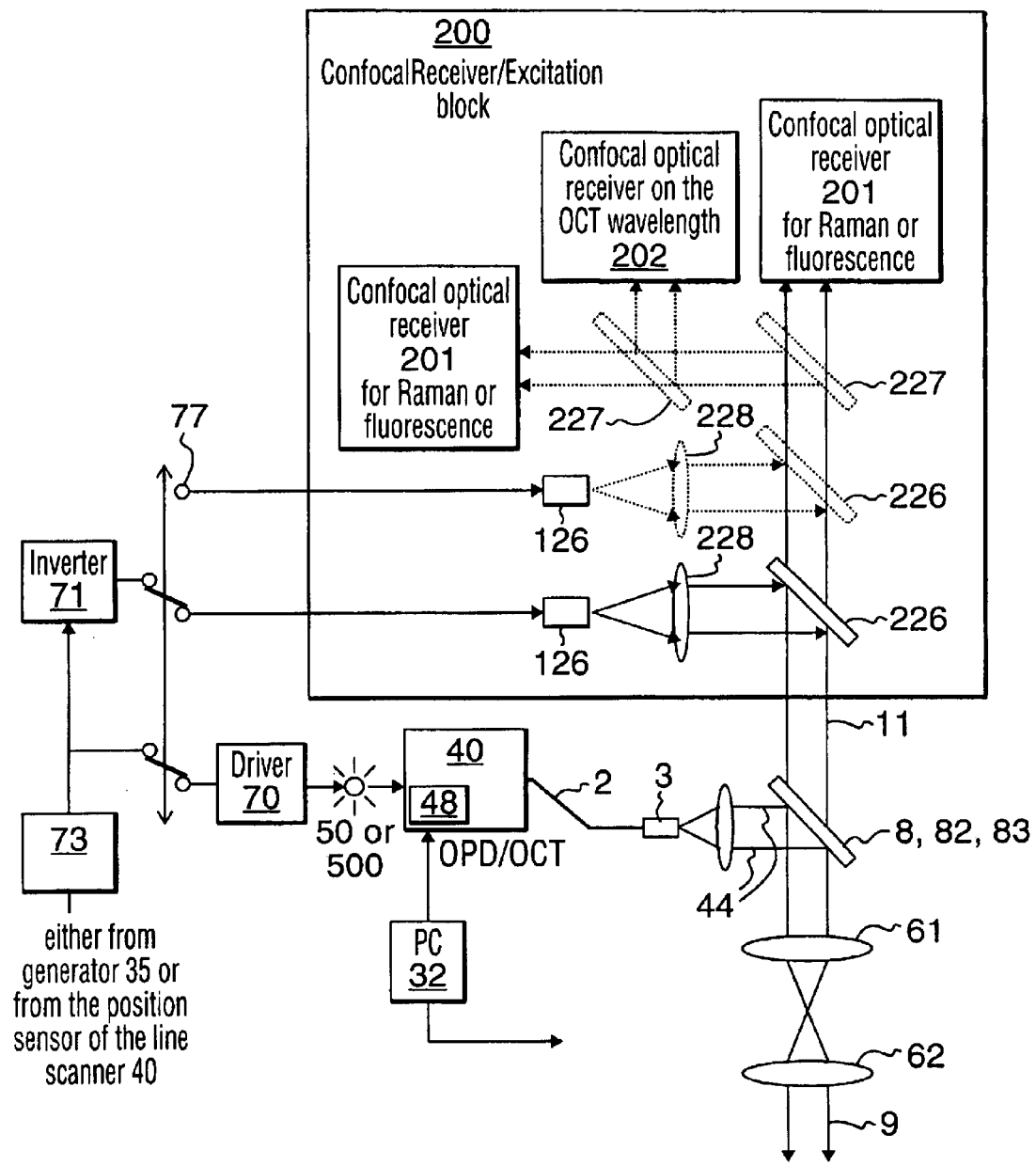
FIG. 13 shows different possibilities in toggling the optical sources in the apparatus.

FIG. 13 shows different possibilities in toggling the sources in the apparatus according to the invention, when using the confocal excitation CE block 200. Switching control signal is applied either from the generator 35, as in FIGS. 9a–c or from the position sensor of the line scanner, 40, as in FIG. 11b. A delay circuit 73 insures that the toggling takes place exactly when the line scanner in the block 10 changes the movement direction when using a resonant galvo-scanner, a galvanometer scanner, or a piezo-vibrator, or when a new facet is introduced into the imaging beam by a polygon mirror. Similar to the embodiments in FIGS. 9 and 11, to insure that while one source is on the other is off, an inverter 71 is used. Different possibilities exist for connecting the outputs of the delay circuit 73 and of the inverter 71. FIG. 13 shows the case where the radiation source 50 (500) and one of the sources 126 in the CE block 200 are toggled, when the switch 77 is down. The apparatus works in the quasi-simultaneous imaging regime, where either an OCT image or an image produced by the Raman or fluorescence radiation emanated by the object under the excitation of the source 126 is produced. This regime is especially useful when the wavelength of the source 50 (500) is close or in the band of the fluorescence or Raman radiation emitted by the object, or the excitation source 126 would disturb the OCT channel if it was fired simultaneously with the source 50 (500). At the same time, the apparatus may display simultaneously a third or more images due to the radiation emanated from the object due to other sources 126 in the block 200 which are on all the time.

When the switch 77 is in the up position, two sources 126 in the block CE 200 are toggled instead. For instance, for safety reasons, two sources 126 on different wavelengths are toggled and the apparatus quasi-simultaneously produce two confocal images on the radiation emanated from the object under the excitation of each of the source 126 which is on. Simultaneously with these images, an OCT image is produced using the source 50 (500) which is on all the time. Additionally, the apparatus may display simultaneously more confocal images due to the radiation emanated from the object due to other sources 126 in the block 200 which are on all the time.

Figure 14:
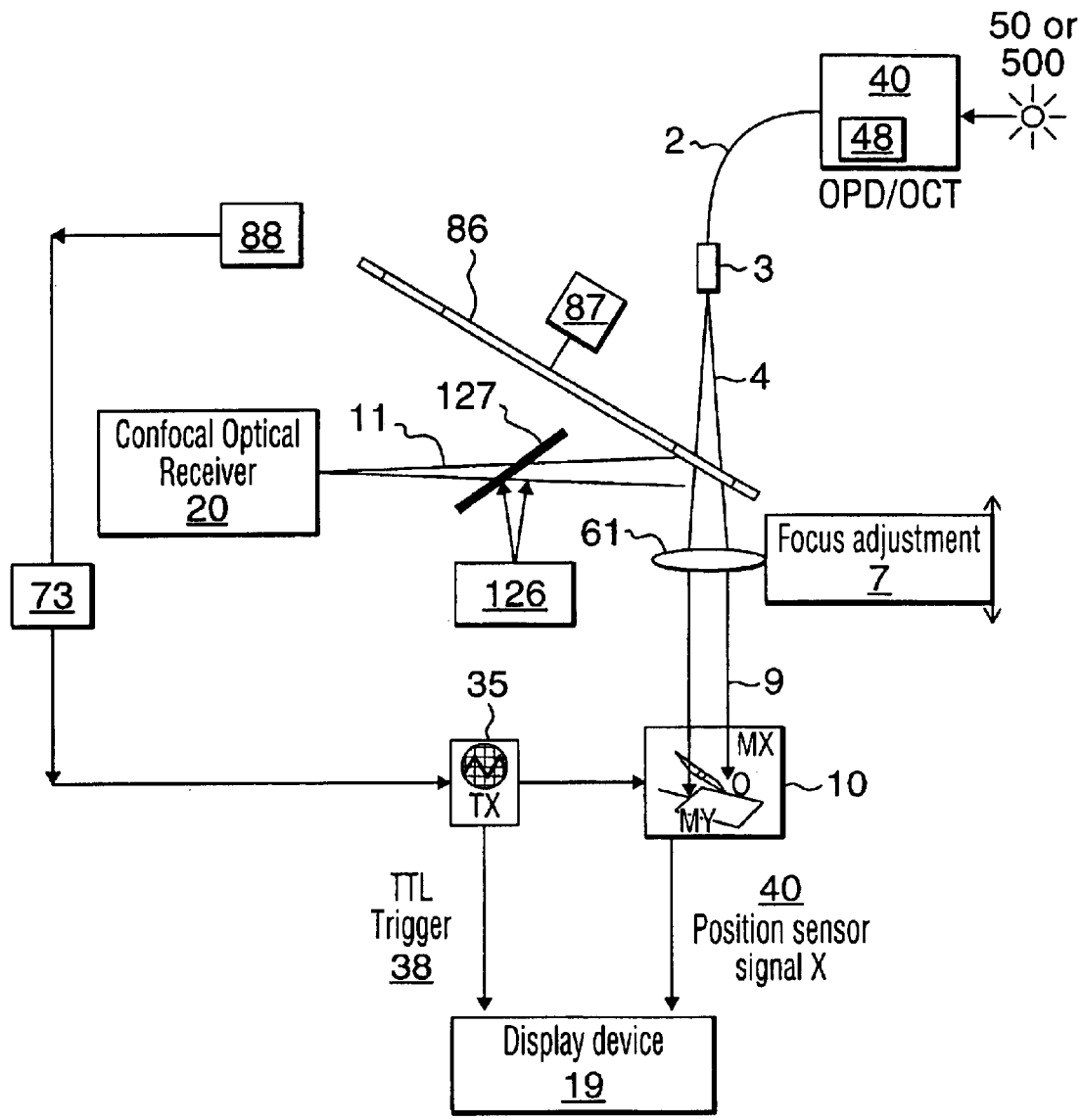
FIG. 14 shows an embodiment of the invention, where internal excitation sources and confocal optical receivers are placed on the same side of the optical splitter, implemented in the form of a rotating holed disk.

FIG. 14 shows an embodiment of the invention, useful for studies of fluorescence or Raman radiation emanated from the object, where the excitation source, 126, and the confocal receiver, 20, are placed on the same side of the optical splitter 8, inside a block, Confocal receiver/excitation, (CE), 200 and where the optical splitter is a rotating holed disk, 86, and where the focus configuration is similar to that in FIG. 2. The disk 86 is equipped with equidistant slits or holes, which by rotation, toggles the beams sent to the object, either the OCT beam when a hole or a slit intersects the beam 4 or otherwise, the beam of the CE block. The mirror of the disk 86 should have good reflectivity for the CE band. This embodiment is especially suitable for those cases where the OCT band is very close to the band of the fluorescence or Raman radiation emanated by the object. A sensor 88 senses the rate of rotation of the disk 86 and synchronises the generator, 35, of the ramps being sent to the line scanner, i.e. successive positive and negative ramps are triggered exactly when the disk 86 interleaves a hole or a mirror into the beam. A delay circuit 73 allows for the eventual skew between the disk 86 and the line scanner. In this way, similar to the embodiment in FIG. 9a, two images are displayed side by side along the line in the raster, the left half corresponding to the OCT image and the right half to the confocal image of the fluorescence or Raman radiation emanated from the object.

Alternatively, the display device 19 can be under the control of position sensor of the line scanner, as explained in connection with the embodiment in FIG. 11b, in which case the generator 35 generates ramps from the signal delivered by the sensor 98 which drives the line scanner and all image is generated for each change of sign of the ramp applied to the line scanner.

It should be obvious for those skilled in the art that the OCT 40 and the block CE 200 could be placed the other way around the disk 86, in configuration R-OCT/T-CE. However, the configuration T-OCT/R-CE as shown in FIG. 13a an 13b is better suited from OCT, which is more sensitive to vibrations than the confocal channel.

Similar functionality can be obtained by replacing the disk 86 with an optical modulator which can operate similarly to the disk, where under the electric or magnetic excitation of a driver 87, the modulator 86 changes the reflectivity/transmission from a low/high value to a high/low value. Liquid crystals are already known which can accomplish such functionality. When the device 86, either disk or optical modulator is slow, the embodiment in FIG. 14 may operate synchronously with the frame scanner, where every second frame will carry a different channel, OCT or confocal instead.

Another aspect of the present invention is dynamic focus. In all FIGS. 2, 3, 5–12, the PC controls both the focusing adjustment mean 7 as well as the optical path difference (OPD) in the OCT channel, by changing the OPD in the OCT, 40, via block 48. This could be optionally used to maintain the focus in synchronism with the coherence matching as explained below. En-face OCT was described for the first time in: "Coherence Imaging by Use of a Newton Rings Sampling Function", by A. Gh. Podoleanu, G. M. Dobre, D. J. Webb, D. A. Jackson and published in Opt. Lett., Vol. 21, pp. 1789–1791, (1996), republished in "Selected Papers on Optical Low-Coherence Reflectometry & Tomography", B. R. Masters and B. J. Thompson eds., SPIE Milestone Series, vol. MS165, SPIE Optical Engineering Press, Washington, 2000, USA, pp. 900–202 and in "Simultaneous En-face Imaging of Two Layers in Human Retina", by A. Gh. Podoleanu, G. M. Dobre, D. J. Webb, D. A. Jackson, published in Opt. Lett., Vol. 22, No. 13, pp. 1039–1041, (1997).

When performing en-face OCT, in the regime of operation as described in the papers above, the dynamic focus needs to operate at a much slower data rate than when performing the longitudinal OCT regime of operation as described in the U.S. Pat. No. 5,321,501. In these circumstances, corrections in the synchronisation law of the two adjusting means 7 and 48 can be more easily applied as the depth is changed in the OCT channel. The two adjusting means are controlled via PC 32, which determines different movement ranges and different advancing speeds. The adjusting means could be moved in steps or at a constant speed, and the ratio of their velocities depends on the optical elements used in the interface optics, 12 and in the focusing adjusting means, lenses 60–62 in the object beam. For instance, if the lenses 60 and the eye lens, 15 have the focal lengths $f_{60}$ and $f_{15}$, a movement of the lens 60 by $\delta z$ results in a $\delta z'$ shift of the focus in the eye, where $\delta z' = -(f_{15}/f_{60})^2 \delta z$. Usually, the optic nerve requires all exploration $\delta z$ of 2 mm in air. With $f_{15}$ fixed, different eyes will obviously have different shifts of focus. Therefore, in the same time, the two adjusting means, 48 and 7 have to cover different distances: $\delta z_{48} = n \delta_{48} z'$ and $\delta z_7 = \delta z' (f_{60}/f_{15})^2$. The simplest implementation is using two PC controlled translation stages. The adjusting procedure uses the mapping apparatus according to the invention in longitudinal OCT regime. The two adjusting means, 48 and 7 are run over a distance slightly larger than the required range, to avoid the nonlinearity in the distance versus time due to the acceleration and deceleration, with the useful image centred. After each scan, the two adjusting means are preferably brought back with much larger speed, although the procedure can be adapted to operate continuously on either sense of OPD variation. After the optimum parameters for the synchronisation of the two adjusting means are found, the mapping apparatus can operate in either longitudinal imaging regime or transverse imaging regime. In this way, a stack of pairs of images are collected for different depths in the object, images delivered by the two channels, OCT and confocal and both images in the stack are depth resolved. When the dynamic focus is not implemented or not used, the focus adjustment is set by the user in the middle of the focusing adjusting range, $\delta z_7$, in which case all the confocal images look the same and only the stack of OCT en-face images is depth resolved.

The optical mapping apparatus may be equipped with two different procedures to find the parameters of the synchronisation between the two adjustments to implement dynamic focus. In both cases, the OPD change in the OCT channel is the leading step and the procedures have to find the parameters of the focus adjusting means, 7, to match the OPD adjusting mean 48. A manual procedure for the focusing adjusting means 7 is based on the manual adjustment of the following parameters: range, initial position and velocity. The parameters of the OPD change in the OCT interferometer to control the depth scanning means, 48 are given: the depth range, the initial position and the velocity. The manual procedure allows the user to act on the range of the focus scanning means 7. When changing the range of the scanning means 7, its velocity is automatically adjusted according to a prefixed factor between velocity and range. Initially, the range of the focusing adjusting means 7 is initially put on zero. The user repeats several longitudinal OCT scans, i.e. the system generates images in the plane (X,Z) for a Y fixed, (Y,Z) for X fixed or circular (θ, Z) for a fixed ρ. While watching the OCT images on the screen of the PC, 32, generated by the display device 19, the user adjusts first the initial position $\{_7$ of the focus adjusting means, until the central part of the longitudinal OCT image becomes sharp. Then, continuing to watch the OCT images on the screen of the PC, 32, generated by the display device 19, the user increases the range, $\delta z_7$ of the focus adjusting means 7, until almost all lines in the longitudinal OCT image corresponding to different depths, exhibit maximum brightness and maximum sharpness. The range of focus adjustment is modified by changing the speed of the focus adjusting mean 7, as both the OPD adjusting mean 48 and the focus adjusting mean 7, operate with the same start and stop controls from the PC 32.

Figure 15:
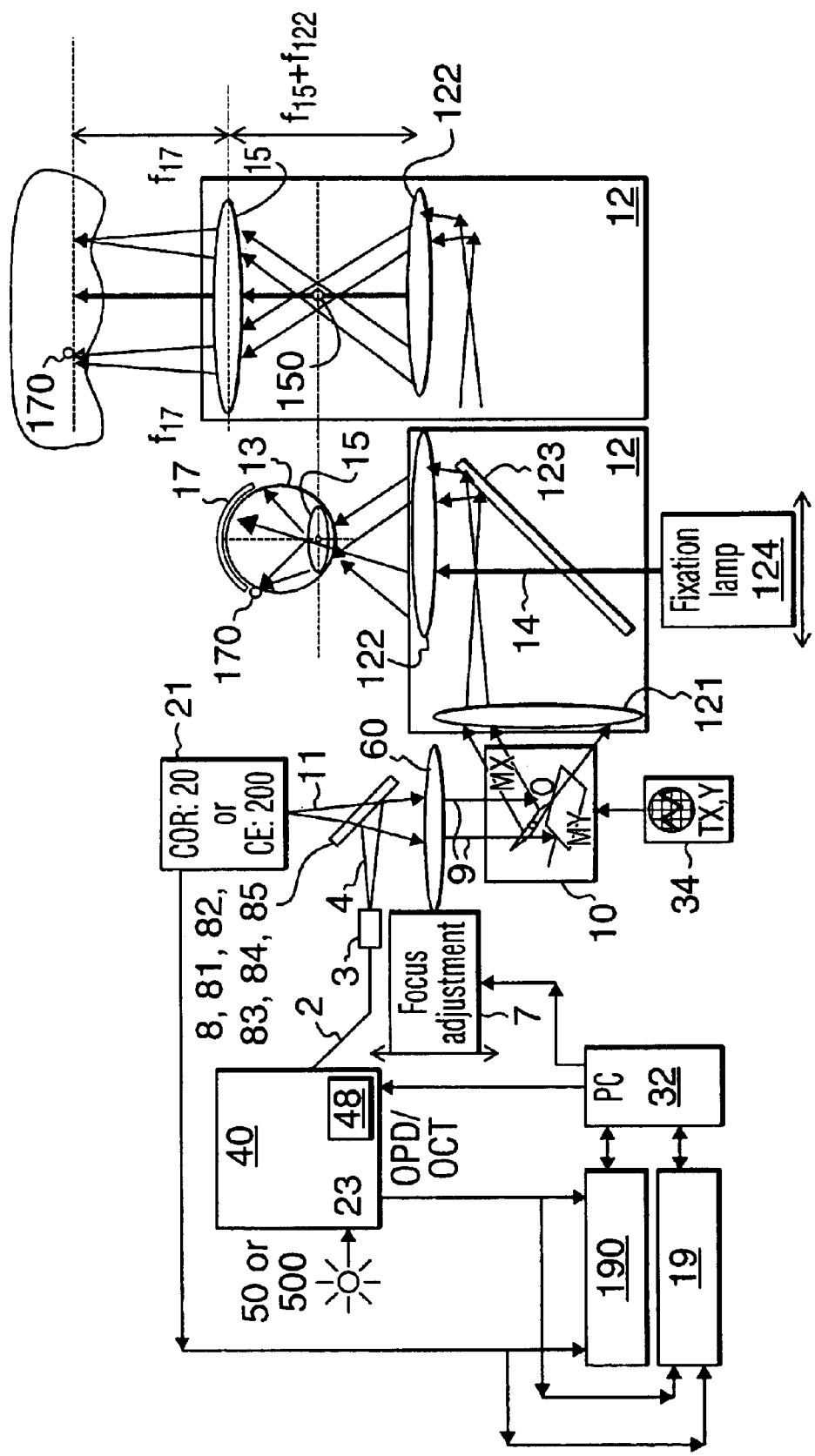
FIG. 15 shows in diagrammatic form, another embodiment according to the invention wherein the dynamic focus provides self-adjustment while the optical mapping apparatus is in the longitudinal OCT regime, until the parameters of the tracking are found.
Figure 16:
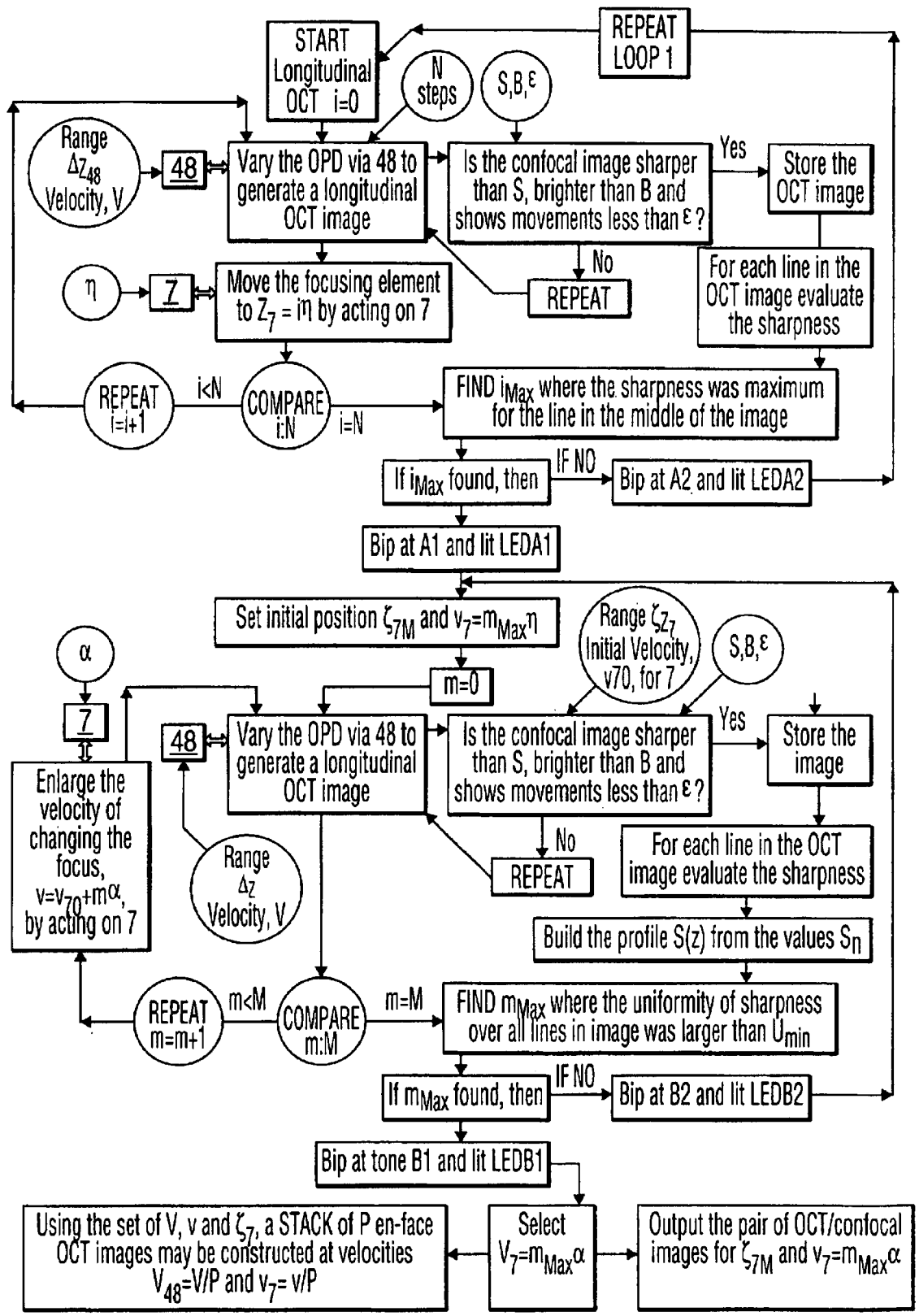
FIG. 16 shows the flow chart of the self-adjusting procedure of the dynamic focus.
Figure 17:
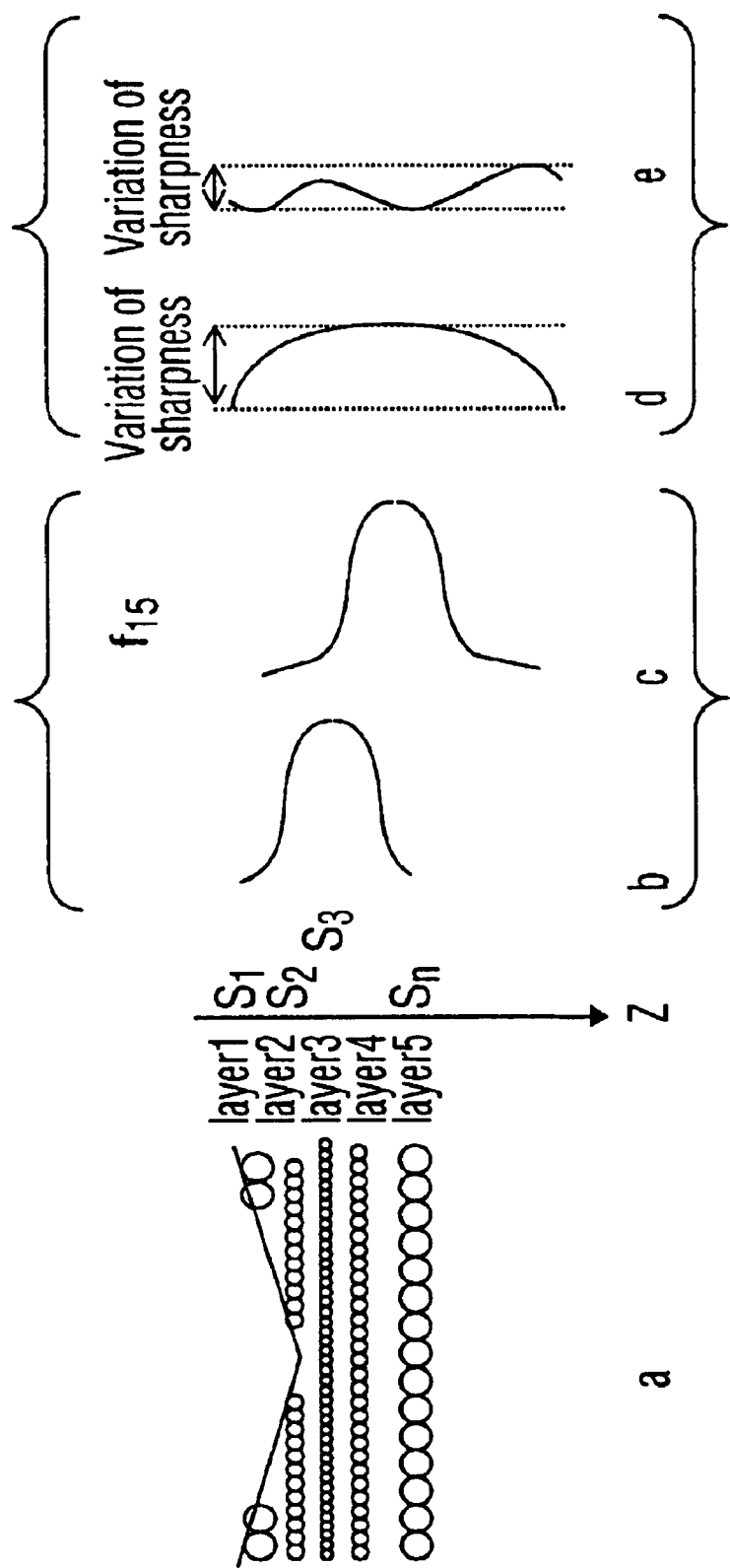
FIG. 17 illustrates the operation of the self-adjusting procedure of the dynamic focus.

Alternatively, the procedure could work in a self adjusting mode, using the embodiment shown in FIG. 15, where a closed loop electronic block, 190, instructs the PC 32 to drive the two axial adjusting means, 7 and 48, modifying the parameters: initial position, $\{_7$ and the range $\delta z_7$ of the focus adjusting means 7. The self-adjusting procedure operates in two loops, according to the steps of the flow chart in FIG. 16, wherein the mapping apparatus acquires images in the plane (X,Z) for a Y fixed, or in the plane (Y,Z) for X fixed or in the surface (θ, Z) for a fixed radius ρ. In the $1^{st}$ loop, the procedure automatically finds the initial position $\{_7$ of the focus scanning means, where for a given depth range, initial position and velocity of the OCT depth scanning means 48, and a given step in the incremental increase of the initial position of the focusing means, η, OCT longitudinal images are repeated for different initial positions of the focusing adjusting means. The images are automatically collected by the procedure for different focus points incremented in steps η, until the middle of the longitudinal OCT image exhibits clarity and sharpness, evaluated by an imaging processing method. Different imaging processing methods are known, one such method may evaluate the size of the pixels in the image, as shown in the inset "a" in FIG. 17. Inset "b" of FIG. 17 shows an intermediate position of the depth profile of the OCT aperture receiver, position which is on the layer 3, to which the pixelation is maximum in inset "a". Inset "c" of FIG. 17 shows the depth profile of the confocal aperture of the OCT moved deeper during the scanning of the interval of initial positions in the $1^{st}$ loop. "i" is the current index step of the loop and η the magnitude of each step in adjusting the initial position $\{_7$ of the focusing adjusting means 7. Once the initial position, $\{_7$, is found, then the procedure automatically starts the $2^{nd}$ loop wherein the range of the focusing adjusting means is incrementally increased in steps of magnitude α until most of the lines in the longitudinal OCT image exhibit sufficient sharpness. Inset "d" shows the uniformity of sharpness in the OCT image at the beginning of the $2^{nd}$ loop and inset "e" shows the uniformity variation of sharpness across the depth by the end of the procedure, where sufficient uniformity of sharpness has been achieved. The clarity and sharpness is determined by the same imaging processing method used in the $1^{st}$ loop. In both loops, each OCT image is validated by the brightness and regularity of the confocal image, when using only one confocal receiver 20, or, one of the confocal images of the confocal optical receivers 20, when using the CE block, 200. The line 21 in FIG. 15 carries one or more confocal signals from CE block, 200, towards the display device 19, and one of these signals is led into the closed loop electronic block, 190. Sound bips of different tonality and luminous indicators keep the user informed about the self adjusting process. The user can recognise from the tonality of the bips and colour of the luminous signals if the procedure takes too long in either loop and can intervene accordingly to adjust the trade-off between the pixel size and the time required to find the initial position of the focusing adjusting means in the $1^{st}$ loop and to adjust the trade-off between the uniformity of the pixelation across the lines in the OCT longitudinal image and the time required to find the range of the focusing adjusting means in the $2^{nd}$ loop.

Both loops use the confocal channel to validate the OCT longitudinal images by checking the quality of the confocal image for sharpness greater than S, brightness larger than B and movements along the line in the raster less than a threshold ε.

Once the optimum adjusting parameters are found, longitudinal images can be collected under dynamic focus closed loop, or stacks of en-face OCT images at different depths, by proportionately reducing the velocites of the two adjusting means, 48 and 7 by the number of slices to be collected from the same depth range.

It should be obvious that the manual or self-adjusting procedure of dynamic focus could be applied to any of the embodiments in FIGS. 2a–d, 3, 5a, 5b, 6a, 6b, 7a–d, 8a–d, 9a–c, 11a–d, 12a–c, 13a,b and the description of the self-adjusting procedure described in connection to FIG. 15, where a focusing configuration of the type described in FIGS. 2a–d was used, can equally be applied to a focusing configuration as that described in FIG. 3.

It should also be obvious that although the transverse scanning means 10 have been presented here as a separate block from the interface optics 12, the embodiments presented in FIGS. 2–9, 11–15 could equally be implemented using transverse scanners, one for each transverse coordinate, separated by lenses or mirrors to convey the beam from one transverse scanner to the other transverse scanner and here from to the object by means known for those skilled in the art of SLO and confocal microscopy, in which case the two blocks 10 and 12 are interrelated.

Thus, it is apparent that there has been provided, in accordance with the present invention, an optical mapping apparatus which fully satisfies the means, objects, and advantages set forth hereinbefore. Therefore, having described specific embodiments of the present invention, it will be understood that alternatives, modifications and variations thereof may be suggested to those skilled in the art, and that it is intended that the present specification embrace all such alternatives, modifications and variations as fall within the scope of the appended claims.

Additionally, for clarity and unless otherwise stated, the word "comprise" and variations of the word such as "comprising" and "comprises", when used in the description and claims of the present specification, is not intended to exclude other additives, components, integers or steps.

We claim:

1. An optical mapping apparatus which comprises:
   an optical coherence tomography (OCT) system built around an in-fiber or a bulk interferometer excited by an optical radiation source;
   a confocal optical receiver with or without adjustable depth resolution;
   an optical splitter, shared by both the interferometer of the OCT and the confocal optical receiver, to direct some of the light returned from an object situated at all object location adjacent to the optical mapping apparatus, wherein, the OCT channel uses the optical-splitter in reflection and the confocal channel in transmission (R-OCT/T-C), or wherein the OCT channel uses the optical-splitter in transmission and the confocal channel uses the optical splitter in reflection (R-OCT/R-C);
   transverse scanning means to effect transverse scanning of the object using an optical output from the optical splitter (as an imaging beam), over a line or a predetermined area in the object;
   interface optics for transferring an optical beam from the transverse scanning means to the object, and for transferring an optical output beam reflected and scattered from the object back to the optical-splitter through the transverse scanning means, and, from the optical-splitter to the interferometer of the OCT channel and/or the optical confocal optical receiver of the confocal channel in a ratio determined by the optical splitter used and wavelength of the radiation backscattered or emitted by the object;
   optionally a fixation lamp for sending light from an external source towards the object;
   optionally, an interface optics-splitter shared by the optional fixation lamp beam and the imaging beam, wherein the interface optics-splitter can be used either in reflection or transmission by the imaging beam, while the fixation lamp beam is transmitted or reflected, respectively;
   focusing adjustment means placed between the optical-splitter and the transverse scanning means, to simultaneously maintain the input aperture of the interferometer and the aperture of the confocal optical receiver in focus, while focusing the scanned beam on the object;
   optionally means to introduce intensity or phase modulation or intensity modulation and phase modulation in the OCT interferometer;
   analysing means for demodulating the photodetected signals of the photodetectors in the interferometer and confocal optical receiver;
   optionally depth adjustment means for altering the optical path difference in sand OCT interferometer over a predetermined amount for at least one point in the transverse scanning means in either steps or continuously at a pace synchronised with the focusing adjustment means, according to a synchronising procedure;
   displaying means for processing and generating an image created by the interferometer and an image created by the confocal optical receiver for the simultaneous display of the said respective images created by the interferometer and the confocal optical receiver; and
   optionally timing means which control two main operation regimes, namely (i) en-face imaging when the mapping apparatus acquires transverse images at constant depth in a perpendicular plane to the optic axis and (ii) longitudinal imaging when the mapping apparatus acquires longitudinal images in a parallel plane to the optic axis, where the optic axis is all imaginary axis from the scanning means through the interface optics to the object.

2. An optical mapping apparatus as claimed in claim 1 wherein said confocal optical receiver is part of a block CE, which consists of at least one confocal optical receiver with or without adjustable depth resolution and optionally, at least one excitation source to excite fluorescence or Raman radiation from the object, where the aperture of the block CE is optically conjugate to the apertures of the confocal optical receiver(s) and of the excitation source(s); and wherein:
   said optical splitter, shared by both the interferometer of the OCT and the block CE, directs some of the light returned from an object situated at an object location adjacent to the optical mapping apparatus, wherein, the OCT channel uses the optical-splitter in reflection and the block CE in transmission (R-OCT/T-CE), or wherein the OCT channel uses the optical-splitter in transmission and the CE block uses the optical splitter in reflection (R-OCT/R-CE);
   said optical-splitter transfers an optical output beam reflected and scattered from the object to the interferometer of the OCT channel and to the block CE in a selected ratio, which ratio is determined by the optical splitter used and the wavelength of the radiation backscattered or emitted by the object; and
   said focusing adjustment means is placed between the optical-splitter and the transverse scanning means, to simultaneously maintain the input aperture of the interferometer and the aperture of the CE block in focus, while focusing the scanned beam on the object.

3. An optical mapping apparatus which comprises an optical radiation source made out of two optical sources of different wavelengths which are combined by a fiber directional single mode coupler or a bulk beam-splitter; a confocal optical receiver with or without adjustable depth resolution; an optical splitter, shared by the optical source and the confocal optical receiver, to direct some of the light returned from an object situated at the object location to the optical confocal optical receiver, where the optical-splitter is used by the source in reflection and by the confocal channel in transmission, regime called R-S/T-C and it is equally possible for the optical-splitter to be used in transmission by the source and in reflection by the confocal channel, regime called TS-S/R-C; transverse scanning means consisting of a line scanner and a frame scanner, to effect transverse scanning of an optical output from the optical splitter over a line or a predetermined area in the object; interface optics for transferring an optical beam from the transverse scanning means to the object and for transferring an optical output beam reflected and scattered from the object back to the optical-splitter through the transverse scanning means, and from the optical-splitter to the confocal optical receiver of the confocal channel in a ratio determined by the optical splitter and the wavelength backscattered or emitted by the object; optionally, a fixation lamp for sending light from an external source towards the object; optionally, an interface optics-splitter shared by the light of the fixation lamp beam and the imaging beam; focusing adjustment means placed between the optical-splitter and the transverse scanning means, to vary the position of the focused beam in the object; analysing means, for demodulating the photodetected signals of the photodetectors in the confocal optical receiver;

depth adjustment means for altering the focus, over a predetermined amount for at least one point in a raster in either steps or continuously at a pace synchronised with the focusing adjustment, according to a synchronising procedure;

displaying means for generating and processing the images created by the confocal optical receivers, and;

timing means which controls the 3D scanning operation regime, when the mapping apparatus acquires en-face images in a plane perpendicular on the optic axis (or in the patient face) at different focusing depths, where the optic axis is an imaginary axis from the scanning means through the interface optics to the object.

4. An optical mapping apparatus which comprises:

an optical coherence tomography (OCT) system built around an in-fiber or a bulk interferometer excited by an optical radiation source;

transverse scanning means to effect transverse scanning of the object using an optical output from the optical splitter (as an imaging beam), over a line or a predetermined area in the object;

interface optics for transferring an optical beam from the transverse scanning means to the object, and for transferring an optical output beam reflected and scattered from the object back to the OCT system;

optionally a fixation lamp for sending light from an external source towards the object;

optionally, an interface optics-splitter shared by the optional fixation lamp beam and the imaging beam, wherein the interface optics-splitter can be used either in reflection or transmission by the imaging beam, while the fixation lamp beam is transmitted or reflected, respectively;

focusing adjustment means placed between the output of the OCT system and the transverse scanning means, to maintain the input aperture of the interferometer in focus, while focusing the scanned beam on the object;

optionally means to introduce intensity or phase modulation or intensity modulation and phase modulation in the OCT interferometer;

analysing means, coupled to the transverse scanning means, for demodulating the photodetected signals of the photodetectors in the interferometer;

depth adjustment means for altering the optical path difference in said OCT interferometer over a predetermined amount for at least one point in the transverse scanning means in either steps or continuously at a pace synchronised with the focusing adjustment means, according to a synchronising procedure;

displaying means for generating and processing the image created by the interferometer;

optionally timing means which control two main operation regimes, namely (i) en-face imaging when the mapping apparatus acquires transverse images at constant depth in a perpendicular plane to the optic axis and (ii) longitudinal imaging when the mapping apparatus acquires longitudinal images, in a parallel plane to the optic axis, where the optic axis is an imaginary axis from the scanning means through the interface optics to the object.

5. An optical mapping apparatus as claimed in any one of claims 1 to 4 wherein said transverse scanning means comprises a line scanner and a frame scanner.

6. An optical mapping, apparatus as claimed in claim 5 wherein a line in object corresponds to the line scanner movement and the advance of the line to the completion of the area scanned corresponds to the movement of the frame scanner.

7. An optical mapping apparatus as claimed in any one of claims 1 to 4 wherein said analysing means is coupled to the transverse scanning means.

8. An optical mapping apparatus as claimed in claim 1 or claim 2, wherein the said optical radiation source is a low coherence source, or a source with adjustable coherence length.

9. An optical mapping apparatus as claimed in claim 1 or claim 2, wherein the said depth adjustment means and the focusing adjustment means use synchronised PC controlling means, with independent initial position, velocity and acceleration and deceleration, which can be controlled continuously or in a stepwise manner.

10. An optical mapping apparatus as claimed in claims 1 or claim 2, wherein the focusing, adjustment means transforms a divergent beam from the optical splitter into a collimated beam or a beam with an adjustable curvature to be sent to the transverse scanning means in order to project a sharp spot on the object, and maintains both the OCT and the confocal channel in focus for all adjusting conditions.

11. An optical mapping apparatus as claimed in claims 1 or claim 2, wherein the focusing, adjustment means transforms a collimated beam from the optical splitter into another collimated beam or a beam with an adjustable curvature to be sent to the transverse scanning means in order to project a sharp spot on the object and maintain in focus both the OCT and the confocal channel, for all adjusting conditions.

12. An optical mapping apparatus as claimed in claim 1 or claim 2, wherein the said focusing adjustment means transforms a collimated beam from the said optical splitter into a convergent beam or a beam with an adjustable curvature to be sent to the transverse scanning means in order to project a sharp spot on the object, and maintains in focus both the OCT and the confocal channel, for all adjusting conditions.

13. An optical mapping apparatus as claimed in any one of claims 1 or 2 wherein the OCT interferometer sends light to the said optical-splitter via a bulk spatial filter or a fibre end.

14. An optical mapping apparatus as claimed in claim 1 or claim 2 wherein the interface optics is equipped with at least one lens or mirror and, when the object is the eye, transforms the fan of rays from the said transverse scanning means into a convergent fan of rays on the eye pupil, with the beam entering the eye collimated for a normal eye, or with an adjustable convergence to accommodate different eye focusing power.

15. An optical mapping apparatus as claimed in claim 1 or claim 2 wherein the interface optics is equipped with at least one lens or mirror and transforms the fan of rays from the said transverse scanning means into a parallel fan of rays converging on the object, with the beam entering the last lens or mirror before the object, collimated or with an adjustable convergence to accommodate different distances between the last lens or last mirror up to the object.

16. An optical mapping apparatus as claimed in any one of claims 1 to 4, wherein said interface optics splitter is a hot mirror, or a cold mirror, or a pass-band filter or a notch filter to allow a beam of a fixation lamp to be directed to a desired part of the object with minimum reduction of the intensity of the imaging beam and of the intensity of the radiation backscattered or emitted by the object.

17. An optical mapping apparatus as claimed in any one of claims 1 to 4 wherein the line scanner and the frame scanner comprise at least two different or similar principle scanners selected from polygon mirrors, galvanometer scanners, acousto-optic modulators, piezo-vibrators, which are placed closed together or spaced apart and interleaved by mirrors or/and lenses, or wherein the line scanner and frame scanner may be one component performing scanning of the object beam in orthogonal directions, and which deliver triggering control signals to control the displaying means.

18. An optical mapping apparatus as claimed in any one of claims 1 to 4, where the displaying mean generates two lines in two images, one image for each successive facet when the line scanner is a polygon mirror, or when rising a galvanometer scanner, acousto-optic modulator or piezo-vibrator, one line for each sign of variation of the driving waveform applied, which waveform may be a sinusoid or a triangle, or when using a resonant scanner, one line for each sign of variation of the sinusoid waveform applied; and wherein a line trigger signal to control the displaying means is derived from the driving waveform, at every change in the variation of the signal applied to the galvanometer scanner, resonant scanner, acousto-optic modulator or piezo-vibrator, or at the beginning of each facet when using a polygon mirror, and wherein the vertical position of the two lines is determined by the amplitude of the driving waveform applied to the frame scanner where the frame scanner is a galvanometer scanner, acousto-optic modulator or piezo-vibrator, wherein said image can comprise as many frames as input signals are applied to the display imaging means to be simultaneously displayed.

19. An optical mapping apparatus as claimed in any one of claims 1 to 4, where the displaying mean uses position sensing signals delivered by the said transverse scanning means, wherein, two lines in two side by side images are generated, such that when using a polygon mirror, one line is generated for each successive facet, whilst when using a galvanometer scanner, resonant scanner, acousto-optic modulator or piezo-vibrator, one line is generated for each sign of variation of the waveform applied, which waveform may be a sinusoid, a triangle, or a nonlinear symmetric periodic signal, and a line trigger signal to control the displaying means is derived from the position sensing signal at every change in the direction of movement of the galvanometer scanner, resonant scanner, acousto-optic modulator or piezo-vibrator, or at the beginning of each facet when using a polygon mirror, and where the vertical position of the two lines is determined by the amplitude of the position sensing signal of the frame scanner, a galvanometer scanner, acousto-optic modulator or piezo-vibrator and where the two side by side images can consists of as many frames as input signals are applied to the display imaging mean to be simultaneously displayed.

20. An optical mapping apparatus as claimed in any one of claims 1 to 4, where the displaying mean uses position sensing signals delivered by said transverse scanning means, wherein, the lateral pixel position in the line in the image generated is determined by the amplitude of the position of the line scanner and wherein the vertical position of the line in the image generated is determined by the amplitude of the position sensing signal of the frame scanner, which image can consists of as many frames as input signals are applied to the display imaging mean to be simultaneously displayed.

21. An optical mapping apparatus as claimed in any one of claim 1, 2 or 4, which operates in the longitudinal imaging regime, and wherein the focusing adjustment means operates synchronously and at a rate determined by the alteration of the optical path in the OCT interferometer.

22. An optical mapping apparatus as claimed in claim 1 or claim 2, wherein the optical splitter consists of a beam-splitter with a gradual or step deposition which results in a reflectivity variation along a variation axis which could be oriented vertically, horizontally or diagonally, and which is mounted on a translatable mount which can be manually or automatically shifted along the variation axis of the reflectivity to adjust the amount of light diverted to the confocal optical receiver.

23. An optical mapping apparatus as claimed in claim 1 or claim 2, wherein the optical-splitter is an electro-optic device or a magneto-optic device or a liquid crystal device with reflectivity and transmission under the control of an electric driver or magnetic driver or both.

24. An optical mapping apparatus as claimed in claim 1 or claim 2, wherein the optical splitter consists of a beam-splitter with a gradual or step deposition which results in a reflectivity and transmission variation along a variation axis which could be oriented vertically, horizontally or diagonally, and which is mounted on a translatable mount which can be manually or automatically shifted continuously or in steps along the variation axis of the reflectivity to adjust the amount of light diverted to the confocal optical receiver or said block CE and wherein the optical power of the said optical source and of the said excitation sources in the block CE are adjusted synchronously with the reflectivity-transmission change of the optical-splitter in such a way to maintain the same optical power sent to the object.

25. An optical mapping apparatus as claimed in claim 1 or claim 2, wherein the optical splitter is an electro-optic device or a magneto-optic device or a liquid crystal device with reflectivity and transmission under the control of an electric driver or magnetic driver, or both, and wherein the optical power of the said optical source or of the said excitation sources in the block CE are adjusted synchronously with the reflectivity-transmission change of the optical-splitter in such a way to maintain the same optical power sent to the object.

26. An optical mapping apparatus as claimed in claim 1, wherein the optical radiation source is made up of two optical sources of different wavelengths having at least one source of low coherence, and wherein the reflectivity and transmission of the optical-splitter is similar for both wavelengths, but wherein the photodetector in the confocal channel is disproportionately more sensitive to the other wavelength than to the wavelength of the low coherence source used in the OCT channel.

27. An optical mapping apparatus as claimed in claim 1, wherein the optical radiation source is made up of two optical sources of different wavelengths, having at least one source of low coherence, and wherein the optical-splitter consists of a beam-splitter with a gradual or step deposition which results in a reflectivity variation along a variation axis which could be oriented vertically, horizontally or diagonally, and which is attached to a translatable mount which can be manually or automatically shifted continuously, or in steps, along the variation axis of the reflectivity to adjust the amount of light diverted to the confocal optical receiver, where in any position of the optical splitter, its reflectivity and transmission are similar for both wavelengths, and wherein the photodetector in the confocal channel is disproportionately more sensitive to the other wavelength than that of the lower coherence source used in the OCT channel.

28. An optical mapping apparatus as claimed in claim 1, wherein the optical radiation source is made up of two optical sources of different wavelengths, at least one source having a lower coherence, and wherein the optical splitter consists of an electro-optic device or a magneto-optic device or a liquid crystal device with reflectivity and transmission under the control of an electric driver or magnetic driver or both, and wherein reflectivity and transmission, which are similar for both wavelengths, is used to adjust the amount of light diverted to the confocal optical receiver, and wherein the photodetector in the confocal channel is disproportionately more sensitive to the other wavelength than to that of the lower coherence source used in the OCT channel.

29. An optical mapping apparatus as claimed in claim 1, wherein the optical radiation source is made up of two optical sources of different wavelengths, at least one source of low coherence, wherein the optical splitter consists of a beam-splitter with a gradual or step deposition which results in reflectivity and transmission similar for both wavelengths but with variation along a variation axis of the reflectivity and transmission which could be oriented vertically, horizontally or diagonally and which optical splitter is mounted on a translatable mount which can be manually or automatically shifted continuously or in steps along the variation axis to adjust the amount of light diverted to the confocal optical receiver, and wherein the photodetector in the confocal channel is disproportionately more sensitive to the other wavelength than that of the low coherence source used in the OCT channel, and wherein the optical power of the said optical sources is adjusted synchronously with the reflectivity-transmission change of the optical-splitter in such a way to maintain the same optical power sent to the object.

30. An optical mapping apparatus as claimed in claim 1, wherein the optical radiation source is made up of two optical sources of different wavelengths, at least one source of a lower coherence, wherein the optical splitter consists of an electro-optic device or a magneto-optic device or a liquid crystal device, with reflectivity and transmission under the control of an electric driver or magnetic driver or both, and wherein reflectivity and transmission are similar for both wavelengths and are used to adjust the amount of light diverted to the confocal optical receiver, and wherein the photodetector in the confocal channel is disproportionately more sensitive to the other wavelength than that of the lower coherence source used in the OCT channel, and wherein the optical power of the said optical source is adjusted synchronously with the reflectivity-transmission change of the optical-splitter in such a way to maintain the same optical power sent to the object.

31. An optical mapping apparatus as claimed in claim 1, wherein the said optical source is made up of two optical sources of different wavelengths, a first source of lower coherence destined for the OCT channel and a second source destined to the confocal channel, and when the configuration R-OCT/T-C is used, the optical splitter is a pass-band filter centered on the wavelength of the second source and which splitter has a relatively large reflectivity for the wavelength of the first source and when the configuration T-OCT/R-C is used, the optical-splitter is a notch filter centred on the wavelength of the second source with a large transmission for the wavelength of the first source.

32. An optical mapping apparatus as claimed in claim 1, wherein the said optical radiation source is made up of two optical sources of different wavelengths, a first source of lower coherence destined for the OCT channel and a second source capable of generating fluorescence or Raman emission in the object under investigation, and wherein when the configuration R-OCT/T-C is used, the optical splitter is a pass-band filter centered on the wavelength of the fluorescence or Raman emission and which has a relatively large reflectivity for the wavelength of the first source, and when the configuration T-OCT/R-C is used, the optical-splitter is a notch filter centred on the wavelength of the fluorescence or Raman emission with a large transmission for the wavelength of the first source.

33. An optical mapping apparatus as claimed in claim 1, wherein the said optical radiation source is made up of two optical sources of different wavelengths, a first source of lower coherence destined for the OCT channel and a second source destined to the confocal channel, wherein the optical splitter consists of a spectral selective beam-splitter selected from a hot mirror, a cold mirror or an edge filter, with the wavelengths of the two sources being on either side of the cut-off wavelength of the spectral reflectivity of the spectral beam-splitter.

34. An optical mapping apparatus as claimed in claim 1, wherein the said optical radiation source is made up of two optical sources of different wavelengths, a first source of lower coherence destined for the OCT channel and a second source capable of generating fluorescence or Raman emission in the object under investigation and wherein the optical splitter consists of a spectral selective beam-splitter selected from a hot mirror, a cold mirror or an edge filter, with the spectral edge being between the wavelength of the first source and the wavelength of the fluorescence or Raman emission.

35. An optical mapping apparatus as claimed in claim 1, wherein the said optical radiation source is made up of two optical sources of different wavelengths, a first source of lower coherence and a second source capable of generating fluorescence or Raman emission in the object under investigation and wherein the optical-splitter comprises two parts, namely: (i) a conventional large band beam-splitter with a reflectivity and transmission similar for both wavelengths used and (ii) a second part which for the configuration R-OCT/T-C is a narrow band spectrally selective element, tuned on the auto-fluorescence or Raman emission of the object, resulting from exposure to the second source, having a relatively high reflectivity for both wavelengths of the first and the second source and which for the configuration T-OCT/R-C is a notch filter centred on the wavelength of the second source with a large transmission for the wavelength of the first source, with the optical-splitter being mounted on a translatable mount which can be manually or automatically shifted along the direction of the variable reflectivity and transmission to position one of the two parts of the optical-splitter into the imaging beam, and wherein the optical power of the said optical sources may be adjusted synchronously with the position of the optical-splitter in such a way to maintain the same optical power sent to the object, or to avoid directing power towards the object which exceeds a pre-set safety limit, and when the optical splitter is positioned on the large band beam-splitter, the second source may be switched off to allow (i) operation of the mapping apparatus with OCT and confocal channel on the wavelength of the first source and (ii) when switched on, the mapping apparatus operates with OCT and confocal channel on different wavelengths, with the OCT channel on the wavelength of the first source and the confocal channel on the wavelength of the second source and when the optical splitter is positioned on the said second part: (iii) the OCT channel operates on the wavelength of the first source and the confocal channel on the wavelength of the second source or (iv) the OCT channel operates on the wavelength of the first source and the confocal channel operates on the fluorescence or Raman radiation which emanates from the object.

36. An optical mapping apparatus as claimed in claim 1, wherein the said optical radiation source is made up of two optical sources of different wavelengths, a first source of lower coherence and a second source capable of generating fluorescence or Raman emission in the object under investigation and wherein the optical-splitter is made out of two parts, (i) one part a conventional large band beam-splitter with a reflectivity and transmission similar for both of the wavelengths used and (ii) a second part which is a hot mirror, or cold mirror, or edge filter with the edge between the wavelength of the first source and of the fluorescence or Raman band emitted from the object under the excitation of the second source, and which is mounted on a translatable mount which can be manually or automatically shifted along the direction of the variable reflectivity and transmission in order to position one of the two parts of the optical-splitter into the imaging beam, and wherein the optical power of the said optical sources may be adjusted synchronously with the position of the optical-splitter in such a way to maintain the same optical power sent to the object, or to avoid directing power towards the object in an amount which exceeds a pre-set safety limit, and when the optical splitter is positioned on the large band beam-splitter, the second source may be switched off to allow (i) operation of the mapping apparatus with OCT and confocal channel on the wavelength of the first source and (ii) when switched on, the mapping apparatus operates with OCT and confocal channel on different wavelengths, with the OCT channel on the wavelength of the first source and the confocal channel on the wavelength of the second source, and when the optical splitter is positioned on the said second part: (iii) the OCT channel operates on the wavelength of the first source and the confocal channel on the wavelength of the second source, or (iv) the OCT channel operates on the wavelength of the first source and the confocal channel operates on the wavelength of the fluorescence or Raman radiation which emanates from the object.

37. An optical mapping apparatus as claimed in claim 1, wherein the optical radiation source is a low coherence source and is capable of generating fluorescence or Raman emission in the object under investigation, and wherein when the configuration R-OCT/T-C is used, the optical-splitter is a narrow band spectrally selective element, tuned on the auto-fluorescence or Raman radiation generated and which exhibits a relatively large reflectivity for the wavelength of the optical source used, and wherein when the configuration T-OCT/R-C is used, the optical-splitter is a notch filter tuned on the auto-fluorescence or Raman radiation generated and which exhibits a relatively large, such as greater than 80%, transmission for the wavelength of the optical source used.

38. An optical mapping apparatus as claimed in claim 1, wherein the said optical radiation source is of low coherence and capable of generating fluorescence or Raman emission in the object under investigation and wherein the optical-splitter is a spectrally selective element selected from a cold mirror, a hot mirror or an edge filter having a cut-off wavelength between the central wavelength of the auto-fluorescence or Raman radiation emitted and the wavelength of the low coherence source.

39. An optical mapping apparatus as claimed in claim 1, wherein the said optical radiation source is of low coherence at wavelength $\lambda_{OCT}$ and when an external excitation source of central wavelength $\lambda_{exc}$ is applied via the interface optics splitter onto the object to excite fluorescence or Raman radiation of wavelength $\lambda_C$, and when $\lambda_{exc} > \lambda_C > \lambda_{OCT}$ and wherein when the configuration R-OCT/T-C is used, the optical-splitter is a band-pass filter tuned on $\lambda_C$ and at the same time, the band-pass filter exhibits a relatively large reflectivity for the wavelength $\lambda_{OCT,}$ and wherein when the configuration T-OCT/R-C is used, the optical-splitter is a notch filter tuned on the wavelength of the auto-fluorescence or Raman radiation generated and which exhibits a relatively large transmission for the wavelength of the optical source used, and the interface optics splitter is a hot mirror or edge filter of the hot mirror type with the cut-off between $\lambda_{exc}$ and $\lambda_C$ when employed in reflection by the imaging beam, and the interface optics splitter is a cold mirror or edge filter of the cold mirror type with the cut-off between $\lambda_{exc}$ and $\lambda_C$ when employed in transmission by the imaging beam.

40. An optical mapping apparatus as claimed in claim 1, wherein the said optical radiation source is of low coherence at wavelength $\lambda_{OCT}$ and when an external excitation source of central wavelength $\lambda_{exc}$ is applied via the interface optics splitter onto the object to excite fluorescence or Raman radiation of wavelength $\lambda_C$, and when $\lambda_{exc} > \lambda_C > \lambda_{OCT}$ and when the configuration R-OCT/T-C is used, the optical-splitter is a hot mirror or edge filter of the hot mirror type, and when the configuration T-OCT/R-C is used, the optical-splitter is a cold mirror or edge filter of the cold mirror type with a cut-off wavelength of between $\lambda_C$ and $\lambda_{OCT}$ and the interface optics splitter is a hot mirror or edge filter of the hot mirror type with a cut-off wavelength between $\lambda_{exc}$ and $\lambda_C$ when employed in reflection by the imaging beam, and the interface optics splitter is a cold mirror or edge filter of the cold mirror type with a cut-off wavelength between $\lambda_{exc}$ and $\lambda_C$ when employed in transmission by the imaging beam.

41. An optical mapping apparatus as claimed in claim 1, wherein the said optical radiation source is of low coherence at wavelength $\lambda_{OCT}$ and when an external excitation source of central wavelength $\lambda_{exc}$ is applied via the interface optics splitter onto the object to excite fluorescence or Raman radiation of wavelength $\lambda_C$, and when $\lambda_{OCT} > \lambda_{exc} > \lambda_C$, and the configuration R-OCT/T-C is used, the optical-splitter is a cold mirror or edge filter of the cold mirror type with a cut-off wavelength between $\lambda_{OCT}$ and $\lambda_{exc,}$ and when the configuration T-OCT/R-C is used, the optical-splitter is a hot mirror or an edge filter of the hot mirror type, and the interface optics splitter, when employed by the imaging beam in reflection, is a band-pass filter tuned on the excitation wavelength, $\lambda_{exc}$ which at the same time, exhibits a relatively large reflectivity for the wavelengths $\lambda_{OCT}$ and $\lambda_C$ and when employed in transmission by the imaging beam, is a notch filter on the excitation wavelength, $\lambda_{exc}$ which at the same time, exhibits a relatively large transmission for the wavelengths $\lambda_{OCT}$ and $\lambda_C$.

42. An optical mapping apparatus as claimed in claim 1, wherein the said optical radiation source is of low coherence at wavelength $\lambda_{OCT}$ and when an external excitation source of central wavelength $\lambda_{exc}$ is applied via the interface optics splitter onto the object to excite fluorescence or Raman radiation of wavelength $\lambda_C$, and when $\lambda_C > \lambda_{exc} > \lambda_{OCT}$ and the configuration R-OCT/T-C is used, the optical-splitter is a hot mirror or edge filter of the hot mirror type with a cut-off wavelength between $\lambda_C$ and $\lambda_{exc,}$ and when the configuration T-OCT/R-C is used, the optical-splitter is a cold mirror or all edge filter of the cold mirror type, and wherein the interface optics splitter, when employed by the imaging beam in reflection, is a narrow band filter tuned on the excitation wavelengths $\lambda_{exc}$ which at the same time, exhibits a relatively large reflectivity for the wavelengths $\lambda_{OCT}$ and $\lambda_C$, and when employed in transmission by the imaging beam, is a notch filter on the excitation wavelength, $\lambda_{exc}$ which at the same time, exhibits a relatively large transmission for the wavelengths $\lambda_{OCT}$ and $\lambda_C$.

43. An optical mapping apparatus as claimed in claim 1, wherein the said optical radiation source is a low coherence optical source at wavelength $\lambda_{OCT}$ and when an external excitation source of central wavelength $\lambda_{exc}$ is applied via the interface optics splitter onto the object to excite fluorescence or Raman radiation of wavelength $\lambda_C$, and when $\lambda_C > \lambda_{exc} > \lambda_{OCT}$ and the configuration R-OCT/T-C is used, the optical-splitter is a spectrally selective element such as a band-pass filter tuned on $\lambda_C$ and at the same time, the pass-band filter exhibits a relatively large reflectivity for the wavelength $\lambda_{OCT,}$ and when the configuration T-OCT/R-C is used, the optical-splitter is a notch filter on the auto-fluorescence or Raman radiation generated by the object and which filter exhibits a relatively large transmission for the wavelength of the optical source used and wherein the interface optics splitter, when employed by the imaging beam in reflection, is a narrow band filter tuned on the excitation wavelength, $\lambda_{exc}$ which at the same time, exhibits a relatively large reflectivity for the wavelengths $\lambda_{OCT}$ and $\lambda_C$, and when employed in transmission by the imaging beam, is a notch filter on the excitation wavelength, $\lambda_{exc}$ which at the same time, exhibits a relatively large transmission for the wavelengths $\lambda_{OCT}$ and $\lambda_C$.

44. An optical mapping apparatus as claimed in claim 1, wherein said optical radiation source is of low coherence at wavelength $\lambda_{OCT}$ and when an external excitation source of central wavelength $\lambda_{exc}$ is applied via the interface optics splitter onto the object to excite fluorescence or Raman radiation of wavelength $\lambda_C$, and when $\lambda_{OCT} > \lambda_C > \lambda_{exc}$ and the configuration R-OCT/T-C is used, the optical-splitter is a cold mirror or edge filter of the cold mirror type, and when the configuration T-OCT/R-C is used, the optical-splitter is a hot mirror or an edge filter of the hot mirror type with a cut-off wavelength between $\lambda_{OCT}$ and $\lambda_{C,}$ and wherein the interface optics splitter, when employed by the imaging beam in reflection, is a cold mirror or edge filter of the cold mirror type with a cut-off wavelength between $\lambda_{exc}$ and $\lambda_C$, and when employed in transmission by the imaging beam, is a hot mirror or edge filter of the hot mirror type with a cut-off wavelength between $\lambda_{exc}$ and $\lambda_C$.

45. An optical mapping apparatus as claimed in claim 2, wherein the optical radiation source is a low coherence source which is capable of generating fluorescence or Raman emission in the object under investigation, and wherein when the configuration R-OCT/T-CE is used, the optical-splitter is a narrow band spectrally selective element, tuned on the auto-fluorescence or Raman radiation generated and which exhibits a relatively large reflectivity for the wavelength of the optical source used, and wherein when the configuration T-OCT/R-CE is used, the optical-splitter is a notch filter tuned on the auto-fluorescence or Raman radiation generated and which exhibits a relatively large transmission for the wavelength of the optical radiation source used.

46. An optical mapping apparatus as claimed in claim 2, wherein the said optical radiation source is of low coherence and capable of generating fluorescence or Raman emission in the object under investigation and wherein the optical-splitter may be a large band beam-splitter or a spectrally selective element selected from a cold mirror, a hot mirror or an edge filter having a cut-off wavelength between the central wavelength of the auto-fluorescence or Raman radiation emitted and the wavelength of the low coherence source.

47. An optical mapping apparatus as claimed in claim 2, wherein the said optical radiation source is of low coherence at wavelength $\lambda_{OCT}$ and wherein when an external excitation source of central wavelength $\lambda_{exc}$ is applied via the interface optics splitter onto the object to excite fluorescence or Raman radiation of wavelength $\lambda_C$, and when $\lambda_{exc} > \lambda_C > \lambda_{OCT}$ and wherein when the configuration R-OCT/T-CE is used, the optical-splitter is a band-pass filter tuned on $\lambda_C$ and at the same time, the band-pass filter exhibits a relatively large reflectivity for the wavelength $\lambda_{OCT,}$ and wherein when the configuration T-OCT/R-CE is used, the optical-splitter is a notch filter tuned on the wavelength of the auto-fluorescence or Raman radiation generated and which exhibits a relatively large transmission for the wavelength of the optical source used, and the interface optics splitter is a hot mirror or edge filter of the hot mirror type with the cut-off between $\lambda_{exc}$ and $\lambda_C$ when employed in reflection by the imaging beam, and the interface optics splitter is a cold mirror or edge filter of the cold mirror type with the cut-off between $\lambda_{exc}$ and $\lambda_C$ when employed in transmission by the imaging beam.

48. An optical mapping apparatus as claimed in claim 2, wherein the said optical radiation source is a low coherence optical source at wavelength $\lambda_{OCT}$ and wherein when an external excitation source of central wavelength $\lambda_{exc}$ is applied via the interface optics splitter onto the object to excite fluorescence or Raman radiation of wavelength $\lambda_C$, and when $\lambda_C > \lambda_{exc} > \lambda_{OCT}$ and the configuration R-OCT/T-CE is used, the optical-splitter is a spectrally selective element such as a band-pass filter tuned on $\lambda_C$ and at the same time, the pass-band filter exhibits a relatively large reflectivity for the wavelength $\lambda_{OCT,}$ and when the configuration T-OCT/R-CE is used, the optical-splitter is a notch filter on the auto-fluorescence or Raman radiation generated by the object and which filter exhibits a relatively large transmission for the wavelength of the optical source used and wherein the interface optics splitter, when employed by the imaging beam in reflection, is a narrow band filter tuned on the excitation wavelength $\lambda_{exc}$ which at the same time, exhibits a relatively large reflectivity for the wavelengths $\lambda_{OCT}$ and $\lambda_C$, and when employed in transmission by the imaging beam, is a notch filter on the excitation wavelength, $\lambda_{exc}$ which at the same time, exhibits a relatively large transmission for the wavelengths $\lambda_{OCT}$ and $\lambda_C$.

49. An optical mapping apparatus as claimed in claim 2, wherein the said optical radiation source is of low coherence at wavelength $\lambda_{OCT}$ and wherein when an external excitation source of central wavelength $\lambda_{exc}$ is applied via the interface optics splitter onto the object to excite fluorescence or Raman radiation of wavelength $\lambda_C$, and when $\lambda_{exc} > \lambda_C > \lambda_{OCT}$ and when the configuration R-OCT/T-CE is used, the optical-splitter is a hot mirror or edge filter of the hot mirror type, and when the configuration T-OCT/R-CE is used, the optical-splitter is a cold mirror or edge filter of the cold mirror type with a cut-off wavelength of between $\lambda_C$ and $\lambda_{OCT}$ and the interface optics splitter is a hot mirror or edge filter of the hot mirror type with a cut-off wavelength between $\lambda_{exc}$ and $\lambda_C$ when employed in reflection by the imaging beam, and the interface optics splitter is a cold mirror or edge filter of the cold mirror type with a cut-off wavelength between $\lambda_{exc}$ and $\lambda_C$ when employed in transmission by the imaging beam.

50. An optical mapping apparatus as claimed in claim 2, wherein the said optical radiation source is of low coherence at wavelength $\lambda_{OCT}$ and wherein when an external excitation source of central wavelength $\lambda_{exc}$ is applied via the interface optics splitter onto the object to excite fluorescence or Raman radiation of wavelength $\lambda_C$, and when $\lambda_{OCT} > \lambda_{exc} > \lambda_C$, and the configuration R-OCT/T-CE is used, the optical-splitter is a cold mirror or edge filter of the cold mirror type with a cut-off wavelength between $\lambda_{OCT}$ and $\lambda_{exc}$, and when the configuration T-OCT/R-CE is used, the optical-splitter is a hot mirror or an edge filter of the hot mirror type, and the interface optics splitter, when employed by the imaging beam in reflection, is a band-pass filter tuned on the excitation wavelength, $\lambda_{exc}$ which at the same time, exhibits a relatively large reflectivity for the wavelengths $\lambda_{OCT}$ and $\lambda_C$ and when employed in transmission by the imaging beam, is a notch filter on the excitation wavelength, $\lambda_{exc}$ which at the same time, exhibits a relatively large transmission for the wavelengths $\lambda_{OCT}$ and $\lambda_C$.

51. An optical mapping apparatus as claimed in claim 2, wherein the said optical radiation source is of low coherence at wavelength $\lambda_{OCT}$ and wherein when an external excitation source of central wavelength $\lambda_{exc}$ is applied via the interface optics splitter onto the object to excite fluorescence or Raman radiation of wavelength $\lambda_C$, and when $\lambda_C > \lambda_{exc} \lambda_{OCT}$ and the configuration R-OCT/F-CE is used, the optical-splitter is a hot mirror or edge filter of the hot mirror type with a cut-off wavelength between $\lambda_C$ and $\lambda_{exc}$, and when the configuration T-OCT/R-CE is used, the optical-splitter is a cold minor or an edge filter of the cold mirror type, and wherein the interface optics splitter, when employed by the imaging beam in reflection, is a narrow band filter tuned on the excitation wavelength, $\lambda_{exc}$ which at the same time, exhibits a relatively large reflectivity for the wavelengths $\lambda_{OCT}$ and $\lambda_C$, and when employed in transmission by the imaging beam, is a notch filter on the excitation wavelength, $\lambda_{exc}$ which at the same time, exhibits a relatively large transmission for the wavelengths $\lambda_{OCT}$ and $\lambda_C$.

52. An optical mapping apparatus as claimed in claim 2, wherein said optical radiation source is of low coherence at wavelength $\lambda_{OCT}$ and wherein when an external excitation source of central wavelength $\lambda_{exc}$ is applied via the interface optics splitter onto the object to excite fluorescence or Raman radiation of wavelength $\lambda_C$, and when $\lambda_{OCT} > \lambda_C > \lambda_{exc}$ and the configuration R-OCT/T-CE is used, the optical-splitter is a cold mirror or edge filter of the cold mirror type, and when the configuration T-OCT/R-CE is used, the optical-splitter is a hot mirror or an edge filter of the hot mirror type with a cut-off wavelength between $\lambda_{OCT}$ and $\lambda_C$, and wherein the interface optics splitter, when employed by the imaging beam in reflection, is a cold mirror or edge filter of the cold mirror type with a cut-off wavelength between $\lambda_{exc}$ and $\lambda_C$, and when employed in transmission by the imaging beam, is a hot mirror or edge filter of the hot mirror type with a cut-off wavelength between $\lambda_{exc}$ and $\lambda_C$.

53. An optical mapping apparatus as claimed in claim 1, wherein the said optical radiation source may consist of two optical sources of either (i) essentially the same wavelength but of different coherence length or (ii) of different wavelength with at least one source of low coherence which are sequentially switched off and on, with one source on and the other off, wherein the displaying mean generates two lines in two images, one image for each successive facet when the line scanner is a polygon mirror, or when using a galvanometer scanner, acousto-optic modulator or piezo-vibrator, one line for each sign of variation of the driving waveform applied, which waveform may be a sinusoid or a triangle, or when using a resonant scanner, one line for each sign of variation of the sinusoid waveform applied; and wherein a line trigger signal to control the displaying means is derived from the driving waveform, at every change in the variation of the signal applied to the galvanometer scanner, resonant scanner, acousto-optic modulator or piezo-vibrator, or at the beginning of each facet when using a polygon mirror, and wherein the vertical position of the two lines is determined by the amplitude of the driving waveform applied to the frame scanner where the frame scanner is a galvanometer scanner, acousto-optic modulator or piezo-vibrator, wherein said image can comprise as many frames as input signals are applied to the display imaging means to be simultaneously displayed; or wherein the displaying mean uses position sensing signals delivered by the said transverse scanning means, wherein, two lines in two side by side images are generated, such that when using a polygon mirror, one line is generated for each successive facet, whilst when using a galvanometer scanner, resonant scanner, acousto-optic modulator or piezo-vibrator, one line is generated for each sign of variation of the waveform applied, which waveform may be a sinusoid, a triangle, or a nonlinear symmetric periodic signal, and a line trigger signal to control the displaying means is derived from the position sensing signal at every change in the direction of movement of the galvanometer scanner, resonant scanner, acousto-optic modulator or piezo-vibrator, or at the beginning of each facet when using a polygon mirror, and where the vertical position of the two lines is determined by the amplitude of the position sensing signal of the frame scanner, a galvanometer scanner, acousto-optic modulator or piezo-vibrator and where the two side by side images can consists of as many frames as input signals are applied to the display imaging mean to be simultaneously displayed, in order to display side by side pairs of OCT and confocal images, with a pair of such images corresponding to each of the two optical sources.

54. An optical mapping apparatus as claimed in claim 2, wherein the said optical radiation source may consist of two optical sources of either (i) essentially the same wavelength but of different coherence length or (ii) of different wavelength with at least one source of low coherence which are sequentially switched off and on, with one source on and the other off, wherein the displaying mean generates two lines in two images, one image for each successive facet when the line scanner is a polygon mirror, or when using a galvanometer scanner, acousto-optic modulator or piezo-vibrator, one line for each sign of variation of the driving waveform applied, which waveform may be a sinusoid or a triangle, or when using a resonant scanner, one line for each sign of variation of the sinusoid waveform applied; and wherein a line trigger signal to control the displaying means is derived from the driving waveform, at every change in the variation of the signal applied to the galvanometer scanner, resonant scanner, acousto-optic modulator or piezo-vibrator, or at the beginning of each facet when using a polygon mirror, and wherein the vertical position of the two lines is determined by the amplitude of the driving waveform applied to the frame scanner where the frame scanner is a galvanometer scanner, acousto-optic modulator or piezo-vibrator, wherein said image can comprise as many frames as input signals are applied to the display imaging means to be simultaneously displayed; or wherein the displaying mean uses position sensing signals delivered by the said transverse scanning means, wherein, two lines in two side by side images are generated, such that when using a polygon mirror, one line is generated for each successive facet, whilst when using a galvanometer scanner, resonant scanner, acousto-optic modulator or piezo-vibrator, one line is generated for each sign of variation of the waveform applied, which waveform may be a sinusoid, a triangle, or a nonlinear symmetric periodic signal, and a line trigger signal to control the displaying means is derived from the position sensing signal at every change in the direction of movement of the galvanometer scanner, resonant scanner, acousto-optic modulator or piezo-vibrator, or at the beginning of each facet when using a polygon mirror, and where the vertical position of the two lines is determined by the amplitude of the position sensing signal of the frame scanner, a galvanometer scanner, acousto-optic modulator or piezo-vibrator and where the two side by side images can consists of as many frames as input signals are applied to the display imaging mean to be simultaneously displayed, in order to display side by side pairs of OCT and confocal images, with a pair of such images corresponding to each of the two optical sources and additionally, other images may be simultaneously displayed, delivered by one of the confocal optical receiver in the CE block tuned on the fluorescence or Raman radiation emitted from the object due to the corresponding internal excitation source in the CE block or/and tuned on the fluorescence or Raman radiation emitted from the object due to one or both of the sources which make the radiation source.

55. An optical mapping apparatus as claimed in any one of claims 39 to 44, wherein the said optical radiation source may be switched off and on, and wherein the displaying mean generates two lines in two images, one image for each successive facet when the line scanner is a polygon mirror, or when using a galvanometer scanner, acousto-optic modulator or piezo-vibrator, one line for each sign of variation of the driving waveform applied, which waveform may be a sinusoid or a triangle, or when using a resonant scanner, one line for each sign of variation of the sinusoid waveform applied; and wherein a line trigger signal to control the displaying means is derived from the driving waveform, at every change in the variation of the signal applied to the galvanometer scanner, resonant scanner, acousto-optic modulator or piezo-vibrator, or at the beginning of each facet when using a polygon mirror, and wherein the vertical position of the two lines is determined by the amplitude of the driving waveform applied to the frame scanner where the frame scanner is a galvanometer scanner, acousto-optic modulator or piezo-vibrator, wherein said image can comprise as many frames as input signals are applied to the display imaging means to be simultaneously displayed; or wherein the displaying mean uses position sensing signals delivered by the said transverse scanning means, wherein, two lines in two side by side images are generated, such that when using a polygon mirror, one line is generated for each successive facet, whilst when using a galvanometer scanner, resonant scanner, acousto-optic modulator or piezo-vibrator, one line is generated for each sign of variation of the waveform applied, which waveform may be a sinusoid, a triangle, or a nonlinear symmetric periodic signal, and a line trigger signal to control the displaying means is derived from the position sensing signal at every change in the direction of movement of the galvanometer scanner, resonant scanner, acousto-optic modulator or piezo-vibrator, or at the beginning of each facet when using a polygon mirror, and where the vertical position of the two lines is determined by the amplitude of the position sensing signal of the flame scanner, a galvanometer scanner, acousto-optic modulator or piezo-vibrator and where the two side by side images can consists of as many flames as input signals are applied to the display imaging mean to be simultaneously displayed, in order to display side by side pairs of OCT and confocal images delivered by the confocal optical receiver tuned on the fluorescence or Raman emanated from the object due to the external source excitation, with a pair of such images corresponding to the time interval when the optical radiation source is off, and the other pair corresponding, to the time interval when the optical radiation source is on.

56. An optical mapping apparatus as claimed in any one of claims 47 to 52; wherein the said radiation source may be switched off and on, and wherein the displaying mean generates two lines in two images, one image for each successive facet when the line scanner is a polygon mirror, or when using a galvanometer scanner, acousto-optic modulator or piezo-vibrator, one line for each sign of variation of the driving waveform applied, which waveform may be a sinusoid or a triangle, or when using a resonant scanner, one line for each sign of variation of the sinusoid waveform applied; and wherein a line trigger signal to control the displaying means is derived from the driving waveform, at every change in the variation of the signal applied to the galvanometer scanner, resonant scanner, acousto-optic modulator or piezo-vibrator, or at the beginning of each facet when using a polygon mirror, and wherein the vertical position of the two lines is determined by the amplitude of the driving waveform applied to the frame scanner where the frame scanner is a galvanometer scanner, acousto-optic modulator or piezo-vibrator, wherein said image can comprise as many frames as input signals are applied to the display imaging means to be simultaneously displayed; or wherein the displaying mean uses position sensing signals delivered by the said transverse scanning means, wherein, two lines in two side by side images are generated, such that when using a polygon mirror, one line is generated for each successive facet, whilst when using a galvanometer scanner, resonant scanner, acousto-optic modulator or piezo-vibrator, one line is generated for each sign of variation of the waveform applied, which waveform may be a sinusoid, a triangle, or a nonlinear symmetric periodic signal, and a line trigger signal to control the displaying means is derived from the position sensing signal at every change in the direction of movement of the galvanometer scanner, resonant scanner, acousto-optic modulator or piezo-vibrator, or at the beginning of each facet when using a polygon mirror, and where the vertical position of the two lines is determined by the amplitude of the position sensing signal of the frame scanner, a galvanometer scanner, acousto-optic modulator or piezo-vibrator and where the two side by side images can consists of as many frames is input signals are applied to the display imaging mean to be simultaneously displayed, in order to display side by side pairs of OCT and confocal images delivered by the confocal optical receiver tuned on the fluorescence or Raman emanated from the object due to the external excitation source, with a pair of such images corresponding to the time interval when the source is off, and the other pair corresponding to the time interval when the source is on, each such pair which may be simultaneously displayed with an additional confocal image generated by the confocal optical receiver in the CE block tuned on the wavelength of the low coherence source.

57. An optical mapping apparatus as claimed in any one of claims 47 to 52, wherein the said radiation source may be switched off, and wherein the displaying mean generates two lines in two images, one image for each successive facet when the line scanner is a polygon mirror, or when using a galvanometer scanner, acousto-optic modulator or piezo-vibrator, one line for each sign of variation of the driving waveform applied, which waveform may be a sinusoid or a triangle, or when using a resonant scanner, one line for each sign of variation of the sinusoid waveform applied; and wherein a line trigger signal to control the displaying means is derived from the driving waveform, at every change in the variation of the signal applied to the galvanometer scanner, resonant scanner, acousto-optic modulator or piezo-vibrator, or at the beginning of each facet wherein using a polygon mirror, and wherein the vertical position of the two lines is determined by the amplitude of the driving waveform applied to the frame scanner where the frame scanner is a galvanometer scanner, acousto-optic modulator or piezo-vibrator, wherein said image can comprise as many frames as input signals are applied to the display imaging means to be simultaneously displayed; or wherein the displaying mean uses position sensing signals delivered by the said transverse scanning means, wherein, two lines in two side by side images are generated, such that when using a polygon mirror, one line is generated for each successive facet, whilst when using a galvanometer scanner, resonant scanner, acousto-optic modulator or piezo-vibrator, one line is generated for each sign of variation of the waveform applied, which waveform may be a sinusoid, a triangle, or a nonlinear symmetric periodic signal, and a line trigger signal to control the displaying means is derived from the position sensing signal at every change in the direction of movement of the galvanometer scanner, resonant scanner, acousto-optic modulator or piezo-vibrator, or at the beginning of each facet when using a polygon mirror, and where the vertical position of the two lines is determined by the amplitude of the position sensing signal of the frame scanner, a galvanometer scanner, acousto-optic modulator or piezo-vibrator and where the two side by side images can consists of as many frames as input signals are applied to the display imaging mean to be simultaneously displayed, in order to display side by side pairs of OCT and confocal images delivered by the confocal optical receiver tuned on the fluorescence or Raman emanated from the object due to the external excitation source, with a pair of such images corresponding to the time interval when the source is off, and the other pair corresponding to the time interval when the source is on, each such pair which may be simultaneously displayed with an additional confocal image or images generated by the confocal optical receiver(s) in the CE block tuned on the band of the (i) low coherence source or/and on the fluorescence or Raman radiation due to respective internal excitation source(s) in the CE block.

58. An optical mapping apparatus as claimed in any one of claims 39 to 42, wherein the said optical radiation source is switched off and on sequentially with the said external excitation source, with one source on and the other off, and wherein the displaying mean generates two lines in two images, one image for each successive facet when the line scanner is a polygon mirror, or when using a galvanometer scanner, acousto-optic modulator or piezo-vibrator, one line for each sign of variation of the driving waveform applied, which waveform may be a sinusoid or a triangle, or when using a resonant scanner, one line for each sign of variation of the sinusoid waveform applied; and wherein a line trigger signal to control the displaying means is derived from the driving waveform, at every change in the variation of the signal applied to the galvanometer scanner, resonant scanner, acousto-optic modulator or piezo-vibrator, or at the beginning of each facet when using a polygon mirror, and wherein the vertical position of the two lines is determined by the amplitude of the driving waveform applied to the frame scanner where the frame scanner is a galvanometer scanner, acousto-optic modulator or piezo-vibrator, wherein said image can comprise as many frames as input signals are applied to the display imaging means to be simultaneously displayed; or wherein the displaying mean uses position sensing signals delivered by the said transverse scanning means, wherein, two lines in two side by side images are generated, such that when using a polygon mirror, one line is generated for each successive facet, whilst when using a galvanometer scanner, resonant scanner, acousto-optic modulator or piezo-vibrator, one line is generated for each sign of variation of the waveform applied, which waveform may be a sinusoid, a triangle, or a nonlinear symmetric periodic signal, and a line trigger signal to control the displaying means is derived from the position sensing signal at every change in the direction of movement of the galvanometer scanner, resonant scanner, acousto-optic modulator or piezo-vibrator, or at the beginning of each facet when using a polygon mirror, and where the vertical position of the two lines is determined by the amplitude of the position sensing signal of the frame scanner, a galvanometer scanner, acousto-optic modulator or piezo-vibrator and where the two side by side images can consists of as many flames as input signals are applied to the display imaging mean to be simultaneously displayed, in order to display side by side pairs of OCT and confocal images delivered by the confocal optical receiver tuned on the fluorescence or Raman emanated from the object due to the external source excitation, with a pair of such images corresponding to the time interval when the optical radiation source is off, and the other pair corresponding to the time interval when the optical radiation source is on.

59. An optical mapping apparatus as claimed in any one of claims 47 to 52, wherein the said and optical radiation source is switched off and on sequentially with the said external excitation source, with one source on and the other off, and wherein the displaying mean generates two lines in two images, one image for each successive facet when the line scanner is a polygon mirror, or when using a galvanometer scanner, acousto-optic modulator or piezo-vibrator, one line for each sign of variation of the driving waveform applied, which waveform may be a sinusoid or a triangle, or when using a resonant scanner, one line for each sign of variation of the sinusoid waveform applied; and wherein a line trigger signal to control the displaying means is derived from the driving waveform, at every change in the variation of the signal applied to the galvanometer scanner, resonant scanner, acousto-optic modulator or piezo-vibrator, or at the beginning of each facet when using a polygon mirror, and wherein the vertical position of the two lines is determined by the amplitude of the driving waveform applied to the frame scanner where the frame scanner is a galvanometer scanner, acousto-optic modulator or piezo-vibrator, wherein said image can comprise as many flames as input signals are applied to the display imaging means to be simultaneously displayed; or wherein the displaying mean uses position sensing signals delivered by the said transverse scanning means, wherein, two lines in two side by side images are generated, such that when using a polygon mirror, one line is generated for each successive facet, whilst when using a galvanometer scanner, resonant scanner, acousto-optic modulator or piezo-vibrator, one line is generated for each sign of variation of the waveform applied, which waveform may be a sinusoid, a triangle, or a nonlinear symmetric periodic signal, and a line trigger signal to control the displaying means is derived from the position sensing signal at every change in the direction of movement of the galvanometer scanner, resonant scanner, acousto-optic modulator or piezo-vibrator, or at the beginning of each facet when using a polygon mirror, and where the vertical position of the two lines is determined by the amplitude of the position sensing signal of the frame scanner, a galvanometer scanner, acousto-optic modulator or piezo-vibrator and where the two side by side images can consists of as many frames as input signals are applied to the display imaging mean to be simultaneously displayed, in order to display side by side pairs of OCT and confocal images delivered by the confocal optical receiver tuned on the fluorescence or Raman emanated from the object due to the external excitation source, with a pair of such images corresponding to the time interval when the optical radiation source is off, and the other pair corresponding to the time interval when the optical radiation source is on, each such pair which may be simultaneously displayed with an additional confocal image generated by the confocal optical receiver in the CE block tuned on the wavelength of the low coherence source.

60. An optical mapping apparatus as claimed in any one of claims 47 to 52, wherein the said optical radiation source is switched off and on sequentially with the said external excitation source, with one source on and the other off, and wherein the displaying mean generates two lines in two images, one image for each successive facet when the line scanner is a polygon mirror, or when using a galvanometer scanner, acousto-optic modulator or piezo-vibrator, one line for each sign of variation of the driving waveform applied, which waveform may be a sinusoid or a triangle, or when using a resonant scanner, one line for each sign of variation of the sinusoid waveform applied; and wherein a line trigger signal to control the displaying means is derived from the driving waveform, at every change in the variation of the signal applied to the galvanometer scanner, resonant scanner, acousto-optic modulator or piezo-vibrator, or at the beginning of each facet when using a polygon mirror, and wherein the vertical position of the two lines is determined by the amplitude of the driving waveform-applied to the frame scanner where the frame scanner is a galvanometer scanner, acousto-optic modulator or piezo-vibrator, wherein said image can comprise as many frames as input signals are applied to the display imaging means to be simultaneously displayed; or wherein the displaying mean uses position sensing signals delivered by the said transverse scanning means, wherein, two lines in two side by side images are generated, such that when using a polygon mirror, one line is generated for each successive facet, whilst when using a galvanometer scanner, resonant scanner, acousto-optic modulator or piezo-vibrator, one line is generated for each sign of variation of the waveform applied, which waveform may be a sinusoid, a triangle, or a nonlinear symmetric periodic signal, and a line trigger signal to control the displaying means is derived from the position sensing signal at every change in the direction of movement of the galvanometer scanner, resonant scanner, acousto-optic modulator or piezo-vibrator, or at the beginning of each facet when using a polygon mirror, and where the vertical position of the two lines is determined by the amplitude of the position sensing signal of the frame scanner, a galvanometer scanner, acousto-optic modulator or piezo-vibrator and where the two side by side images can consists of as many frames as input signals are applied to the display imaging mean to be simultaneously displayed, in order to display side by side pairs of OCT and confocal images delivered by the confocal optical receiver tuned on the fluorescence or Raman emanated from the object due to the external excitation source, with a pair of such images corresponding to the time interval when the optical radiation source is off, and the other pair corresponding to the time interval when the optical radiation source is on, each such pair which may be simultaneously displayed with an additional confocal image or images generated by the confocal optical receiver(s) in the CE block tuned on the band of the (i) low coherence source or/and on the fluorescence or Raman radiation due to respective internal excitation source(s) in the CE block.

61. An optical mapping apparatus as claimed in claim 1, wherein an external excitation source of central wavelength $\lambda_{exc}$ is applied via the interface optics splitter onto the object to excite fluorescence or Raman radiation of wavelength $\lambda_C$ in the object and wherein the optical splitter consists of two to four different parts selected from: (i) a large band beam-splitter, (ii) a gradual deposited large band beam-splitter, (iii) a band-pass or a notch filter and (iv) an edge filter deposition, or a cold or hot mirror, wherein the optical splitter could be manually positioned or is mounted on a servo controlled mount which can be controllably positioned to select one of the parts above of the optical splitter to intersect the said imaging beam, and while doing so the low coherence optical source and the excitation source may be switched on or off to give further versatility to the optical mapping apparatus, and the display mean operates by generating two lines in two images, one image for each successive facet when the line scanner is a polygon mirror, or when using a galvanometer scanner, acousto-optic modulator or piezo-vibrator, one line for each sign of variation of the driving waveform applied, which waveform may be a sinusoid or a triangle, or when using a resonant scanner, one line for each sign of variation of the sinusoid waveform applied; and wherein a line trigger signal to control the displaying means is derived from the driving waveform, at every change in the variation of the signal applied to the galvanometer scanner, resonant scanner, acousto-optic modulator or piezo-vibrator, or at the beginning of each facet when using a polygon mirror, and wherein the vertical position of the two lines is determined by the amplitude of the driving waveform applied to the frame scanner where the frame scanner is a galvanometer scanner, acousto-optic modulator or piezo-vibrator, wherein said image can comprise as many frames as input signals are applied to the display imaging means to be simultaneously displayed; or wherein the displaying mean uses position sensing signals delivered by the said transverse scanning means, wherein, two lines in two side by side images are generated, such that when using a polygon mirror, one line is generated from each successive facet, whilst when using a galvanometer scanner, resonant scanner, acousto-optic modulator or piezo-vibrator, one line is generated for each sign of variation of the waveform applied, which waveform may be a sinusoid, a triangle, or a nonlinear symmetric periodic signal, and a line trigger signal to control the displaying means is derived from the position sensing signal at every change in the direction of movement of the galvanometer scanner, resonant scanner, acousto-optic modulator or piezo-vibrator, or at the beginning of each facet when using a polygon mirror, and where the vertical position of the two lines is determined by the amplitude of the position sensing signal of the frame scanner, a galvanometer scanner, acousto-optic modulator or piezo-vibrator and where the two side by side images can consists of as many frames as input signals are applied to the display imaging mean to be simultaneously displayed, in order to display pairs of OCT and confocal images delivered by the confocal optical receiver tuned on the fluorescence or Raman emanated from the object due to the external source excitation, and when one or both sources are switched on and off, to display pair of such images corresponding to the time interval when the switched source is off and the other pair corresponding to the time interval when the switched source is on, and wherein the switching is controlled by the line trigger, and wherein said regimes comprise:

(i) two channel operation on OCT and con focal on the same wavelength when the optical-splitter is positioned on the large band beam-splitter, the low coherence source is on and the external excitation source is off;

(ii) OCT and confocal on the same wavelength with adjustable ratio of the signals in the two channels when the optical-splitter is positioned on the graded large band beam-splitter, the low coherence source is on and the external excitation source is off;

(iii) OCT and fluorescence or Raman on sufficiently distinct wavelengths when the optical-splitter is positioned on the band-pass filter when employing R-OCT/T-C configuration or on the notch filter when employing T-OCT/R-C configuration, and the filter tuned on the central wavelength of the fluorescence or Raman radiation emitted from the object, and (a) only the low coherence source is on and the external excitation source is off and the Raman or fluorescence radiation is due to the low coherence source, and (b) both the low coherence source and the external excitation source are on, when the Raman or fluorescence radiation is due to the external excitation source; Switched regimes;

(iv) Triple imaging regime, where a pair of OCT and confocal images is quasi-simultaneous with a fluorescence or Raman image, when the OCT channel is not disturbed by the excitation source of the fluorescence or Raman and when the optical-splitter is positioned on either (a) the edge filter, or cold or hot mirror or (b) on the band-pass filter when employing R-OCT/T-C configuration or on the notch filter when employing T-OCT/R-C configuration, filter tuned on the central wavelength of the fluorescence or Raman radiation emitted from the object, the low coherence source being switched on and off and the external excitation source is on; and (v) Triple imaging regime, where a pair of OCT and confocal images is quasi-simultaneous with a fluorescence or Raman image and when the OCT channel would be disturbed by the excitation source of the fluorescence or Raman, and when the optical-splitter is positioned on either (a) the edge filter, or a cold or hot mirror, or (b) on the band-pass filter when employing R-OCT/T-C configuration or on the notch filter when employing T-OCT/R-C configuration, wherein the filter is tuned on the central wavelength of the fluorescence or Raman radiation emitted from the object, and the low coherence source and the external excitation source are switched on and off with one source on and the other off.

62. An optical mapping apparatus as claimed in claim 2, wherein an external excitation source of central wavelength $\lambda_{exc}$ is applied via the interface optics splitter onto the object to excite fluorescence or Raman radiation of wavelength $\lambda_C$ in the object and wherein the optical splitter consists of two to four different parts selected from: (i) a large band beam-splitter, (ii) a gradual deposited large band beam-splitter, (iii) a band-pass or a notch filter and (iv) an edge filter deposition, or a cold or hot mirror, wherein the optical splitter could be manually positioned or is mounted on a servo controlled mount which can be controllably positioned to select one of the parts above of the optical splitter to intersect the said imaging beam, and while doing so the low coherence optical source and the excitation source may be switched on or off to give further versatility to the optical mapping apparatus, and the display mean operates by generating two lines in two images, one image for each successive facet when the line scanner is a polygon mirror, or when using a galvanometer scanner, acousto-optic modulator or piezo-vibrator, one line for each sign of variation of the driving waveform applied, which waveform may be a sinusoid or a triangle, or when using a resonant scanner, one line for each sign of variation of the sinusoid waveform applied; and wherein a line trigger signal to control the displaying means is derived from the driving waveform, at every change in the variation of the signal applied to the galvanometer scanner, resonant scanner, acousto-optic modulator or piezo-vibrator, or at the beginning of each facet when using a polygon mirror, and wherein the vertical position of the two lines is determined by the amplitude of the driving waveform applied to the frame scanner where the frame scanner is a galvanometer scanner, acousto-optic modulator or piezo-vibrator, wherein said image can comprise as many frames as input signals are applied to the display imaging means to be simultaneously displayed; or wherein the displaying mean uses position sensing signals delivered by the said transverse scanning means, wherein, two lines in two side by side images are generated, such that when using a polygon mirror, one line is generated for each successive facet, whilst when using a galvanometer scanner, resonant scanner, acousto-optic modulator or piezo-vibrator, one line is generated for each sign of variation of the waveform applied, which waveform may be a sinusoid, a triangle, or a nonlinear symmetric periodic signal, and a line trigger signal to control the displaying means is derived from the position sensing signal at every change in the direction of movement of the galvanometer scanner, resonant scanner, acousto-optic modulator or piezo-vibrator, or at the beginning of each facet when using a polygon mirror, and where the vertical position of the two lines is determined by the amplitude of the position sensing signal of the frame scanner, a galvanometer scanner, acousto-optic modulator or piezo-vibrator and where the two side by side images can consists of as many frames as input signals are applied to the display imaging mean to be simultaneously displayed, in order to display pairs of OCT and confocal images delivered by one of the confocal optical receiver in block CE tuned on the fluorescence or Raman emanated from the object due to the external source excitation, and when one or both sources are switched on and off, to display pair of such images corresponding to the time interval when the switched source(s) is (are) off, and the other pair corresponding to the time interval when the switched source(s) is (are) on, and wherein the switching is controlled by the line trigger signal, and wherein said regimes comprise:

(i) Multiple channel operation when the optical-splitter is positioned on the large band beam-splitter, the low coherence source is on and the external excitation source is off, where a pair of OCT and confocal images on the same wavelength may simultaneously be displayed with an additional confocal image or images generated by the confocal optical receiver(s) in the CE block tuned on the band of the fluorescence or Raman radiation due to respective internal excitation source(s) in the CE block;

(ii) Multiple channel operation when the optical-splitter is positioned on the graded large band beam-splitter, the low coherence source is on and the external excitation source is off, where the pair of OCT and confocal images on the same wavelength may simultaneously be displayed with an additional confocal image or images generated by the confocal optical receiver(s) in the CE block tuned on the band of the fluorescence or Raman radiation due to respective internal excitation source(s) in the CE block, with adjustable ratio of the OCT signal on one hand and of all the other signals on the other hand;

(iii) Triple channel operation, when the optical-splitter is positioned on the band-pass filter when employing R-OCT/T-CE configuration or on the notch filter when employing T-OCT/R-CE configuration, and (a) only the low coherence source is on and the external excitation source is off and the filter is tuned on the central wavelength of the fluorescence or Raman radiation emitted from the object due to the low coherence source, and (b) both the low coherence source and the external excitation source are on, when the filter is tuned on the central wavelength of the fluorescence or Raman radiation emitted from the object due to the external excitation source, where such OCT and fluorescence or Raman on sufficiently distinct wavelengths may be simultaneously displayed with an additional confocal image generated by a confocal optical receiver in the CE block tuned on the band of the low coherence source;

(iv) Multiple imaging regime, when the OCT channel is not disturbed by the external excitation source of the fluorescence or Raman but the fluorescence/Raman confocal optical receiver is disturbed by the low coherence source, in which case the low coherence source is switched on and off and the external excitation source is on, and the optical-splitter is positioned on the edge filter, or cold or hot mirror wherein the pair of OCT and confocal image due to the external excitation source is simultaneous with a fluorescence or Raman image generated by the confocal optical receiver(s) in the CE block tuned on the band of the fluorescence or Raman radiation due to respective internal excitation source(s) in the CE block;

(v) Triple imaging regime, when the OCT channel is not disturbed by the external excitation source of the fluorescence or Raman but the fluorescence/Raman confocal optical receiver is disturbed by the low coherence source, in which case the low coherence source is switched on and off and the external excitation source is on, and the optical-splitter is positioned on the band-pass filter when employing R-OCT/T-CE configuration or on the notch filter when employing T-OCT/R-CE configuration, filter tuned on the central wavelength of the fluorescence or Raman radiation emitted from the object under the excitation of the external source, wherein the pair of OCT and confocal image due to the external excitation source may be simultaneous with an additional confocal image generated by a confocal optical receiver in the CE block tuned on the band of the low coherence source;

(vi) Multiple imaging regime, when the OCT channel is disturbed by the external excitation source of the fluorescence or Raman and the fluorescence/Raman confocal optical receiver is disturbed by the low coherence source, in which case both the low coherence source and the external excitation source are switched on and off, with one source on and the other off, and the optical-splitter is positioned on the edge filter, or a cold or hot mirror, wherein the pair of OCT and confocal image due to the external excitation source is simultaneous with a fluorescence or Raman image generated by the confocal optical receiver(s) in the CE block tuned on the band of the fluorescence or Raman radiation due to respective internal excitation source(s) in the CE block;

(vii) Triple imaging regime, when the OCT channel is disturbed by the external excitation source of the fluorescence or Raman and the fluorescence/Raman confocal optical receiver is disturbed by the low coherence source, in which case both the low coherence source and the external excitation source are switched on and off, with one source on and the other off, and the optical-splitter is positioned on the band-pass filter when employing R-OCT/T-CE configuration or on the notch filter when employing T-OCT/R-CE configuration, filter tuned on the central wavelength of the fluorescence or Raman radiation emitted from the object under the excitation of the external source, wherein the pair of OCT and confocal image due to the external excitation source may be simultaneous with an additional confocal image generated by a confocal optical receiver in the CE block tuned on the band of the low coherence source.

63. An optical mapping apparatus as claimed in claim 2, suitable for those cases where the OCT band is close to the band of the fluorescence or Raman radiation emanated by the object, where the optical splitter is a rotating high reflective disk equipped with equidistant slits or holes, which by rotation, toggles the beams sent to the object, either the OCT beam or the beam of the CE block, the disk being equipped with a sensor to sense the rate of rotation of the disk and synchronise the line scanner to deliver a ramp of a certain slope for each time the beam is reflected and to deliver a ramp of opposite slope for each time the beam is transmitted through the disk, the same sensor synchronising the image display, with a further delay circuit to allow for the eventual skew between the disk and the line scanner, with the frame scanner under the excitation of a separate ramp or saw-tooth generator, and wherein two images are displayed side by the side along the line in the raster, the left half corresponding to the OCT image and the right half to the confocal image of the fluorescence or Raman radiation emanated from the object under the excitation of an internal excitation source.

64. An optical mapping apparatus as claimed in claim 2, suitable for those cases where the OCT band is close to the band of the fluorescence or Raman radiation emanated by the object, where the optical splitter is a rotating high reflective disk equipped with equidistant slits or holes, which by rotation, toggles the beams sent to the object, either the OCT beam or the beam of the CE block, the disk being equipped with a sensor to sense the rate of rotation of the disk and synchronise the frame scanner to deliver a ramp of a certain slope for each time the beam is reflected and to deliver a ramp of opposite slope for each time the beam is transmitted through the disk, the same sensor synchronising the image display, with a further delay circuit to allow for the eventual skew between the disk and the frame scanner, with the line scanner under the excitation of a separate ramp or saw-tooth generator, and wherein two images are displayed successively side by the side, one corresponding to the OCT image and the next to the confocal image of the fluorescence or Raman radiation emanated from the object under the excitation of an internal excitation source.

65. An optical mapping apparatus as claimed in claim 2, suitable for those cases where the OCT band is close to the band of the fluorescence or Raman radiation emanated by the object, where the optical splitter is a fast optical modulator, whose transmission/reflection can be switched high and low, which under electric or magnetic field, toggles the beams sent to the object, either the OCT beam or the beam of the CE block, the modulator is equipped with a sensor to sense the transmission/reflectivity change and synchronise the line scanner to deliver a ramp of a certain slope for each time the beam is reflected and to deliver a ramp of opposite slope for each time the beam is transmitted through the modulator, the same sensor synchronising the image display, with a further delay circuit to allow for the eventual skew between the modulator and the line scanner, with the frame scanner under the excitation of a separate ramp or saw-tooth generator, and wherein two images are displayed side by the side along the line in the raster, the left half corresponding to the OCT image and the right half to the confocal image of the fluorescence or Raman radiation emanated from the object under the excitation of an internal excitation source.

66. An optical mapping apparatus as claimed in claim 2, suitable for those cases where the OCT band is close to the band of the fluorescence or Raman radiation emanated by the object, where the optical splitter is a fast optical modulator, whose transmission/reflection can be switched high and low, which under electric or magnetic field, toggles the beams sent to the object, either the OCT beam or the beam of the CE block, the modulator is equipped with a sensor to sense the transmission/reflectivity change and synchronise the frame scanner to deliver a ramp of a certain slope for each time the beam is reflected and to deliver a ramp of opposite slope for each time the beam is transmitted through the modulator, the same sensor synchronising the image display, with a further delay circuit to allow for the eventual skew between the modulator and the frame scanner, with the line scanner under the excitation of a separate ramp or saw-tooth generator, and wherein two images are displayed successively in time side by the side, one corresponding to the OCT image and the next to the confocal image of the fluorescence or Raman radiation emanated from the object under the excitation of an internal excitation source.

67. An optical mapping apparatus as claimed in claim 2, where different imaging regimes can be implemented by toggling synchronous with the line scanner either
   (i) the optical radiation source with the external excitation source while one or more internal excitation sources is (are) all the time either off or on, or some on and some off;
   (ii) the optical radiation source with one of the internal excitation source, while other internal excitation sources or/and external excitation source is (are) all the time either off or on, or some on and some others off;
   (iii) one of the internal excitation source with the external excitation source while other internal excitation source (s) is (are) all the time either off or on, or some on and some others off;
   (iv) two internal excitation sources, while other internal excitation sources or/and the external excitation source is (are) all the time either off or on, or some on and some others off;
   (v) the optical radiation source along with one or more internal excitation sources with the external excitation source while other internal excitation source(s) is (are) all the time either off or on, or some on and some off;
   (vi) the optical radiation source along with the external excitation source with one of the internal excitation source, while (the) other internal excitation source(s) is (are) all the time either off or on, or some on and some others off;
   (ii) one or more internal excitation sources with the external excitation source while other internal excitation sources is (are) all the time either off or on, or some on and some others off where the sources to be toggled are those which are disturbing each other if they worked at the same time.

68. An optical mapping apparatus as claimed in any one of claims 26 to 36 or 53 or 54 wherein the two optical sources are combined by a fiber directional single mode coupler, a bulk beam-splitter or a WDM (wavelength demultiplexing) coupler.

69. An optical mapping apparatus as claimed in claim 1 or claim 2, wherein that part of the object where a 3D stack of OCT images is to be collected, with the view to produce a 3D reproduction, is selected on the basis of information collected by the confocal channel in claim 1 or one of the confocal channels in claim 2, tuned on either the wavelength of the OCT channel or on a wavelength different from the OCT channel, including a wavelength resulting from the fluorescence or Raman emission from the object.

70. An optical mapping apparatus as claimed in claim 1 or claim 2, wherein that part of the object where fluorescence or Raman image is to be collected by the confocal channel or one of the confocal channels, is selected based on the information provided by the OCT channel in either one longitudinal or en-face image, or based on a stack of 3D OCT en-face images at different depths.

71. An optical mapping apparatus as claimed in any one of claims 26 to 36 or 53 to 54 where the ratio of the average brightness in the confocal images in the pair of images obtained with the two said sources is used to correct the brightness in the OCT images in the pair of images generated by the same said two sources.

72. A method of preparing a dual channel image of an object, which method utilizes an optical mapping apparatus as claimed in claim 1 or claim 2, where the parameters of the said synchronising procedure of the OCT depth adjusting means and focusing adjusting means, which parameters include range, initial position and velocity of the focus adjusting means for a given initial position, depth range and velocity of the OCT depth scanning means, are found using a manual procedure performed by the user with the following steps: (i) with the range of the focusing adjusting means on zero, the user repetitively changes the initial position of the focusing adjusting means while acquiring longitudinal OCT images in the plane (X,Z) for a Y fixed, or in the plane (Y,Z) for X fixed or in the surface (θ, Z) for a fixed radius ρ, with such images repeated until the central part of the longitudinal OCT image becomes sharp; (ii) continuing to watch the OCT images generated by the display device, the riser increases the range of the focus adjusting means until most of the lines in the longitudinal OCT image become sharper, and wherein in doing so in both steps, the user validates each OCT image by the brightness and regularity of the confocal image according to claim 1 or one of the confocal images according to claim 2 and once the initial position and range of the focusing adjustment corresponding to a given set of range and speed of the optical path adjustment in the OCT channel are found, they are stored for subsequent measurements.

73. A method of preparing a dual channel image of an object, which method utilizes an optical mapping apparatus as claimed in claim 1 or claim 2, where the parameters of the said synchronising procedure of the OCT depth adjusting means and focusing adjusting means, parameters which are the range, initial position and velocity of the focus adjusting means for a given depth range and velocity of the OCT depth scanning means, are found using a self-adjusting procedure operating in two loops, wherein the mapping apparatus according to the invention operates in a longitudinal OCT regime and acquires images in the plane (X,Z) for a Y fixed, or in the plane (Y,Z) for X fixed or in the surface (θ, Z) for a fixed radius ρ, wherein in a first loop, the procedure automatically finds the initial position of the focus scanning means, where for a given depth range, initial position and velocity of the OCT depth scanning means, OCT longitudinal images are repeated for different initial positions of the focusing adjusting means, which are automatically selected by the procedure until the middle of the longitudinal OCT image exhibits clarity and sharpness, evaluated by an imaging processing method, which one possibility of operation of the imaging processing method based on the evaluation of the size of the pixels in the image, and once the initial position is found, then the procedure automatically starts a second loop wherein the range of the focusing adjusting means is incrementally increased until most of the lines in the longitudinal OCT image exhibit sharpness, as determined by the same imaging processing method, and wherein each OCT image in either loop is validated by the brightness and regularity of the confocal image or one of the confocal images, and wherein sounds of different tonality, and/or luminous indicators of different colour keep the user informed about the self adjusting process and wherein the user can recognise from the tonality of the sounds and/or colour of the luminous signals, that the procedure is taking too long in either loop and can intervene accordingly to adjust the trade-off between the pixel size and the time required to find the initial position of the focusing adjusting means in the first loop and to adjust the trade-off between the uniformity of the pixelation across the lines in the OCT longitudinal image and the time required to find the range of the focusing adjusting means in the second loop, and when the optimum parameters are found they are stored and the self-adjusting procedure stops and the user is informed.

74. A method of preparing a dual channel image of an object, as claimed in claim 72 wherein after the parameters of the said synchronising procedure of the OCT depth adjusting means and focusing adjusting means are found, stacks of N en-face OCT images are collected by mowing the depth adjusting means at a velocity obtained by dividing the velocity of advancing the focusing means, as well as the velocity of advancing the optical path difference in the OCT interferometer, by N.

75. A method of preparing a dual channel image of an object, as claimed in claim 73, wherein after the parameters of the said synchronising procedure of the OCT depth adjusting means and focusing adjusting means are found, stacks of N en-face OCT images arc collected by mowing the depth adjusting means at a velocity obtained by dividing the velocity of advancing the focusing means, as well as the velocity of advancing the optical path difference in the OCT interferometer, by N.

76. An optical mapping apparatus as claimed in any one of claims 39 to 44 or 47 to 52 wherein an optical combiner is used to mix the beam of the fixation lamp with the beam of the excitation beam from the excitation source, and the combined beam is sent to the object, where the optical combiner could be a large bandwidth beam-splitter, or a cold or a hot mirror or a band-pass or notch filter or edge filter to accommodate the spectral properties of the fixation lamp and excitation source.

77. An optical mapping apparatus as claimed in claim 3, wherein the said two optical sources are sequentially switched off and on, with one source on and the other off, and wherein the displaying mean generates two lines in two images, one image for each successive facet when the line scanner is a polygon mirror, or when using a galvanometer scanner, acousto-optic modulator or piezo-vibrator, one line for each sign of variation of the driving waveform applied, which waveform may be a sinusoid or a triangle, or when using a resonant scanner, one line for each sign of variation of the sinusoid waveform applied; and wherein a line trigger signal to control the displaying means is derived from the driving waveform, at every change in the variation of the signal applied to the galvanometer scanner, resonant scanner, acousto-optic modulator or piezo-vibrator, or at the beginning of each facet when using a polygon mirror, and wherein the vertical position of the two lines is determined by the amplitude of the driving waveform applied to the frame scanner where the frame scanner is a galvanometer scanner, acousto-optic modulator or piezo-vibrator, wherein said image can comprise as many frames as input signals are applied to the display imaging means to be simultaneously displayed; or wherein the displaying mean uses position sensing signals delivered by the said transverse scanning means, wherein, two lines in two side by side images are generated, such that when using a polygon mirror, one line is generated for each successive facet, whilst when using a galvanometer scanner, resonant scanner, acousto-optic modulator or piezo-vibrator, one line is generated for each sign of variation of the waveform applied, which waveform may be a sinusoid, a triangle, or a nonlinear symmetric periodic signal, and a line trigger signal to control the displaying means is derived from the position sensing signal at every change in the direction of movement of the galvanometer scanner, resonant scanner, acousto-optic modulator or piezo-vibrator, or at the beginning of each facet when using a polygon mirror, and where the vertical position of the two lines is determined by the amplitude of the position sensing signal of the frame scanner, a galvanometer scanner, acousto-optic modulator or piezo-vibrator and where the two side by side images can consists of as many frames as input signals are applied to the display imaging mean to be simultaneously displayed, and wherein the optical-splitter is a large bandwidth beam-splitter, with similar reflectivity and transmission for both wavelengths used.

78. An optical mapping apparatus as claimed in claim 3, wherein the said optical sources are polarised linearly in the same direction by polarising means, sources which are sequentially switched off and on, with one source on and the other off, wherein the displaying mean generates two lines in two images, one image for each successive facet when the line scanner is a polygon mirror, or when using a galvanometer scanner, acousto-optic modulator or piezo-vibrator, one line for each sign of variation of the driving waveform applied, which waveform may be a sinusoid or a triangle, or when using a resonant scanner, one line for each sign of variation of the sinusoid waveform applied; and wherein a line trigger signal to control the displaying means is derived from the driving waveform, at every change in the variation of the signal applied to the galvanometer scanner, resonant scanner, acousto-optic modulator or piezo-vibrator, or at the beginning of each facet when using a polygon mirror, and wherein the vertical position of the two lines is determined by the amplitude of the driving waveform applied to the frame scanner where the frame scanner is a galvanometer scanner, acousto-optic modulator or piezo-vibrator, wherein said image can comprise as many frames as input signals are applied to the display imaging means to be simultaneously displayed; or wherein the displaying mean uses position sensing signals delivered by the said transverse scanning means, wherein, two lines in two side by side images are generated, such that when using a polygon mirror, one line is generated for each successive facet, whilst when using a galvanometer scanner, resonant scanner, acousto-optic modulator or piezo-vibrator, one line is generated for each sign of variation of the waveform applied, which waveform may be a sinusoid, a triangle, or a nonlinear symmetric periodic signal, and a line trigger signal to control the displaying means is derived from the position sensing signal at every change in the direction of movement of the galvanometer scanner, resonant scanner, acousto-optic modulator or piezo-vibrator, or at the beginning of each facet when using a polygon mirror, and where the vertical position of the two lines is determined by the amplitude of the position sensing signal of the frame scanner, a galvanometer scanner, acousto-optic modulator or piezo-vibrator and where the two side by side images can consists of as many frames as input signals are applied to the display imaging mean to be simultaneously displayed, and wherein the optical-splitter is a large bandwidth beam-splitter, with similar reflectivity and transmission for both wavelengths used and wherein the optical-splitter is a polarisation sensitive beam-splitter which allows the polarisation field of the sources to pass through to the focusing means and the confocal optical receiver may have supplementary polarisation selecting means in a direction perpendicular to that of the sources and a quarter wave plate at 45° from the direction of polarisation of the sources in used in the imaging beam.

79. An optical mapping apparatus as claimed in claim 1 or claim 2 wherein the output of the OCT interferometer is linearly polarised and wherein the optical-splitter is a polarisation sensitive beam-splitter which allows the polarisation field of the signal coming out of the OCT interferometer to pass through to the focusing means and where the confocal optical receiver operates on a polarisation direction rectangular to that of the OCT interferometer.

80. An optical mapping apparatus as claimed in claim 4, wherein the display mean operates by generating two lines in two images, one image for each successive facet when the line scanner is a polygon mirror, or when using a galvanometer scanner, acousto-optic modulator or piezo-vibrator, one line for each sign of variation of the driving waveform applied, which waveform may be a sinusoid or a triangle, or when using a resonant scanner, one line for each sign of variation of the sinusoid waveform applied; and wherein a line trigger signal to control the displaying means is derived from the driving waveform, at every change in the variation of the signal applied to the galvanometer scanner, resonant scanner, acousto-optic modulator or piezo-vibrator, or at the beginning of each facet when using a polygon mirror, and wherein the vertical position of the two lines is determined by the amplitude of the driving waveform applied to the frame scanner where the frame scanner is a galvanometer scanner, acousto-optic modulator or piezo-vibrator, wherein said image can comprise as many frames as input signals are applied to the display imaging means to be simultaneously displayed; or wherein the displaying mean uses position sensing signals delivered by the said transverse scanning means, wherein, two lines in two side by side images are generated, such that when using a polygon mirror, one line is generated for each successive facet, whilst when using a galvanometer scanner, resonant scanner, acousto-optic modulator or piezo-vibrator, one line is generated for each sign of variation of the waveform applied, which waveform may be a sinusoid, a triangle, or a nonlinear symmetric periodic signal, and a line trigger signal to control the displaying means is derived from the position sensing signal at every change in the direction of movement of the galvanometer scanner, resonant scanner, acousto-optic modulator or piezo-vibrator, or at the beginning of each facet when using a polygon mirror, and where the vertical position of the two lines is determined by the amplitude of the position sensing signal of the frame scanner, a galvanometer scanner, acousto-optic modulator or piezo-vibrator and where the two side by side images can consists of as many frames as input signals are applied to the display imaging mean to be simultaneously displayed, and wherein said optical radiation source consists of two optical sources of essentially the same wavelength but of different coherence length which are sequentially switched off and on, with one source on and the other off, where the switching is controlled by the line trigger signal.

81. An optical mapping apparatus as claimed in claim 1, claim 2 or claim 4, wherein if the OCT interferometer uses optical fiber, the fiber end shining light towards the optical splitter is cleaved at an angle and eventually antireflection coated, and the lenses are anti-reflection coated for the wavelength of the source used in the OCT channel to avoid feedback back into the OCT and optical radiation source as well as to maintain a low level of the excess photon noise.

82. An optical mapping apparatus as claimed in claim 1 or claim 2 where the optical splitters, such as the optical splitter shared by the confocal and the OCT channel and also all surfaces of different elements in the confocal optical receiver(s) including the photodetector(s) facet, the fiber input surface when using optical fiber and the other spectral selective elements are tilted to avoid reflections back into the OCT system and the interface optics splitter is preferably used in reflection by the OCT channel, or if used in transmission, materials of similar thickness are placed in the reference path of the OCT interferometer.

83. An optical mapping apparatus as claimed in claim 1, claim 3 or claim 4 where the said displaying means for processing and generating the images may be synchronised with the said transverse scanning means.

* * * * *